United States Patent
Schaer

(10) Patent No.: US 9,707,034 B2
(45) Date of Patent: Jul. 18, 2017

(54) INTRALUMINAL METHOD AND APPARATUS FOR ABLATING NERVE TISSUE

(75) Inventor: Alan K Schaer, San Jose, CA (US)

(73) Assignee: ReCor Medical, Inc., Palo Alto, CA (US)

(*) Notice: Subject to any disclaimer, the term of this patent is extended or adjusted under 35 U.S.C. 154(b) by 0 days.

(21) Appl. No.: 13/478,825

(22) Filed: May 23, 2012

(65) Prior Publication Data

US 2013/0072928 A1    Mar. 21, 2013

Related U.S. Application Data

(63) Continuation of application No. 10/611,838, filed on Jun. 30, 2003, now abandoned.

(Continued)

(51) Int. Cl.
| | | |
|---|---|---|
| A61B 18/14 | (2006.01) | |
| A61N 7/02 | (2006.01) | |
| A61B 18/18 | (2006.01) | |
| A61B 18/20 | (2006.01) | |
| A61B 8/00 | (2006.01) | |
| A61B 17/00 | (2006.01) | |

(Continued)

(52) U.S. Cl.
CPC ........ *A61B 18/1492* (2013.01); *A61B 8/4281* (2013.01); *A61B 18/18* (2013.01); *A61B 18/1815* (2013.01); *A61B 18/20* (2013.01); *A61N 7/02* (2013.01); *A61N 7/022* (2013.01); *A61B 17/2202* (2013.01); *A61B 2017/0046* (2013.01); *A61N 2007/003* (2013.01); *A61N 2007/0043* (2013.01); *A61N 2007/0065* (2013.01); *A61N 2007/0078* (2013.01); *A61N 2007/0082* (2013.01); *A61N 2007/0091* (2013.01); *A61N 2007/0095* (2013.01)

(58) Field of Classification Search
CPC ............ A61B 18/1492; A61B 17/2202; A61B 18/00285; A61B 2017/22051; A61B 18/04
USPC ........ 600/437, 439, 459, 466, 470; 601/2–4, 601/41
See application file for complete search history.

(56) References Cited

U.S. PATENT DOCUMENTS

| | | |
|---|---|---|
| 3,168,659 A | 2/1965 | Bayre et al. |
| 4,055,190 A | 10/1977 | Tany et al. |

(Continued)

FOREIGN PATENT DOCUMENTS

| | | |
|---|---|---|
| DE | 20 2005 022 060 U1 | 11/2012 |
| EP | 0659387 | 6/1995 |

(Continued)

OTHER PUBLICATIONS

Swain, et al. Gastrointestinal Endoscopy. 1994; 40:AB35.

(Continued)

*Primary Examiner* — Rochelle Turchen
(74) *Attorney, Agent, or Firm* — Foley & Lardner LLP; Christopher C. Bolten; Nicola A. Pisano

(57) ABSTRACT

Methods and apparatus for treating gastroesophageal reflex and other luminal conditions provide for delivering acoustic energy to a body lumen to remodel tissue surrounding the body lumen. In the case of treating GERD, a catheter carrying an ultrasonic or other vibrational transducer is introduced to the lower esophageal sphincter, and acoustic energy is delivered to the sphincter in order to tighten or bulk the sphincter such that reflex is reduced.

13 Claims, 27 Drawing Sheets

Related U.S. Application Data

(60) Provisional application No. 60/419,317, filed on Oct. 16, 2002, provisional application No. 60/393,339, filed on Jul. 1, 2002.

(51) Int. Cl.
  *A61N 7/00* (2006.01)
  *A61B 17/22* (2006.01)

(56) References Cited

U.S. PATENT DOCUMENTS

| | | |
|---|---|---|
| 4,084,582 A | 4/1978 | Nigam |
| 4,185,501 A | 1/1980 | Proudian et al. |
| 4,194,510 A | 3/1980 | Proudian |
| 4,338,942 A | 7/1982 | Fogarty |
| 4,381,007 A | 4/1983 | Doss |
| 4,387,720 A | 6/1983 | Miller |
| 4,391,281 A | 7/1983 | Green |
| 4,402,307 A | 9/1983 | Hanson et al. |
| 4,403,612 A | 9/1983 | Fogarty |
| 4,422,447 A | 12/1983 | Schiff |
| 4,433,692 A | 2/1984 | Baba |
| 4,602,624 A | 7/1986 | Naples et al. |
| 4,643,186 A | 2/1987 | Rosen et al. |
| 4,650,466 A | 3/1987 | Luther |
| 4,672,961 A | 6/1987 | Davies |
| 4,680,499 A | 7/1987 | Umemura et al. |
| 4,685,334 A | 8/1987 | Latimer |
| 4,691,714 A | 9/1987 | Wong et al. |
| 4,722,347 A | 2/1988 | Abrams et al. |
| 4,744,366 A | 5/1988 | Jang |
| 4,785,815 A | 11/1988 | Cohen |
| 4,800,316 A | 1/1989 | Ju-Zhen |
| 4,813,934 A | 3/1989 | Engelson et al. |
| 4,841,977 A | 6/1989 | Griffith et al. |
| 4,869,263 A | 9/1989 | Segal et al. |
| 4,914,510 A | 4/1990 | Brennesholtz et al. |
| 4,945,912 A | 8/1990 | Langberg |
| 4,972,826 A | 11/1990 | Koehler et al. |
| 4,976,711 A | 12/1990 | Parins et al. |
| 4,983,169 A | 1/1991 | Furukawa |
| 5,006,119 A | 4/1991 | Acker et al. |
| 5,019,034 A | 5/1991 | Weaver et al. |
| 5,104,393 A | 4/1992 | Isner |
| 5,105,116 A | 4/1992 | Okamoto et al. |
| 5,114,423 A | 5/1992 | Kasprzyk et al. |
| 5,117,831 A | 6/1992 | Jang et al. |
| 5,125,928 A | 6/1992 | Parins et al. |
| 5,135,001 A | 8/1992 | Sinofsky et al. |
| 5,140,987 A | 8/1992 | Schuger |
| 5,160,336 A | 11/1992 | Favre |
| 5,167,233 A | 12/1992 | Eberle et al. |
| 5,175,711 A | 12/1992 | Fujita et al. |
| 5,203,326 A | 4/1993 | Collins et al. |
| 5,209,299 A | 5/1993 | Ayres |
| 5,213,098 A | 5/1993 | Bennett et al. |
| 5,217,454 A | 6/1993 | Khoury |
| 5,226,421 A | 7/1993 | Frisbie et al. |
| 5,226,430 A | 7/1993 | Spears et al. |
| 5,240,005 A | 8/1993 | Viebach |
| 5,242,438 A | 9/1993 | Saadatmanesh et al. |
| 5,242,441 A | 9/1993 | Avitall |
| 5,246,438 A | 9/1993 | Langberg |
| 5,269,291 A | 12/1993 | Carter |
| 5,281,213 A | 1/1994 | Milder et al. |
| 5,281,218 A | 1/1994 | Imran |
| 5,282,785 A | 2/1994 | Shapland et al. |
| 5,286,254 A | 2/1994 | Shapland et al. |
| 5,293,868 A | 3/1994 | Nardella |
| 5,295,484 A | 3/1994 | Marcus et al. |
| 5,300,068 A | 4/1994 | Rosar et al. |
| 5,304,120 A | 4/1994 | Crandell et al. |
| 5,305,731 A | 4/1994 | Buchholtz |
| 5,305,755 A | 4/1994 | Nakao |
| 5,324,255 A | 6/1994 | Passafaro et al. |
| 5,324,259 A | 6/1994 | Taylor et al. |
| 5,334,193 A | 8/1994 | Nardella |
| 5,338,295 A | 8/1994 | Cornelius et al. |
| 5,342,292 A | 8/1994 | Nita et al. |
| 5,348,010 A | 9/1994 | Schnall et al. |
| 5,364,388 A | 11/1994 | Koziol |
| 5,368,591 A | 11/1994 | Lennox et al. |
| 5,385,148 A | 1/1995 | Lesh et al. |
| 5,391,197 A | 2/1995 | Burdette |
| 5,400,267 A | 3/1995 | Denen et al. |
| 5,415,654 A | 5/1995 | Daikuzono |
| 5,419,335 A | 5/1995 | Hartmann et al. |
| 5,421,338 A | 6/1995 | Crowley et al. |
| 5,423,319 A | 6/1995 | Seyed-Bolorforosh |
| 5,423,744 A | 6/1995 | Gencheff et al. |
| 5,423,755 A | 6/1995 | Kesten |
| 5,423,807 A | 6/1995 | Milder |
| 5,431,663 A | 7/1995 | Carter |
| 5,452,733 A | 9/1995 | Sterman et al. |
| 5,454,782 A | 10/1995 | Perkins |
| 5,456,259 A * | 10/1995 | Barlow .............. A61B 8/12 600/459 |
| 5,458,568 A | 10/1995 | Racchini et al. |
| 5,458,626 A | 10/1995 | Krause |
| 5,468,239 A | 11/1995 | Tanner et al. |
| 5,470,352 A | 11/1995 | Rappaport |
| 5,471,988 A | 12/1995 | Fujio |
| 5,472,406 A | 12/1995 | de la Torre et al. |
| 5,477,736 A | 12/1995 | Lorraine |
| 5,484,400 A | 1/1996 | Edwards et al. |
| 5,488,955 A | 2/1996 | Dias |
| 5,492,532 A | 2/1996 | Ryan et al. |
| 5,498,238 A | 3/1996 | Shapland et al. |
| 5,499,971 A | 3/1996 | Shapland et al. |
| 5,505,700 A | 4/1996 | Leone et al. |
| 5,507,724 A | 4/1996 | Hofmann et al. |
| 5,513,639 A | 5/1996 | Satomi et al. |
| 5,549,644 A | 8/1996 | Lundquist et al. |
| 5,553,611 A | 9/1996 | Budd et al. |
| 5,562,720 A | 10/1996 | Stern et al. |
| 5,569,198 A | 10/1996 | Racchini et al. |
| 5,571,088 A | 11/1996 | Lennox et al. |
| 5,571,147 A | 11/1996 | Sluijter et al. |
| 5,571,215 A | 11/1996 | Sterman et al. |
| 5,575,766 A | 11/1996 | Swartz et al. |
| 5,575,787 A | 11/1996 | Abela et al. |
| 5,582,609 A | 12/1996 | Swanson et al. |
| 5,596,989 A | 1/1997 | Morita |
| 5,599,345 A | 2/1997 | Edwards et al. |
| 5,606,974 A | 3/1997 | Castellano et al. |
| 5,620,479 A | 4/1997 | Diederich |
| 5,626,576 A | 5/1997 | Janssen |
| 5,628,730 A | 5/1997 | Shapland et al. |
| 5,630,837 A | 5/1997 | Crowley |
| 5,634,899 A | 6/1997 | Shapland et al. |
| 5,643,279 A | 7/1997 | Trotta |
| 5,655,539 A | 8/1997 | Wang et al. |
| 5,669,932 A | 9/1997 | Fischell et al. |
| 5,672,174 A | 9/1997 | Gough et al. |
| D384,743 S | 10/1997 | Chia |
| 5,676,662 A | 10/1997 | Fleischhacker et al. |
| 5,676,692 A | 10/1997 | Sanghvi et al. |
| 5,688,266 A | 11/1997 | Edwards et al. |
| 5,690,691 A | 11/1997 | Chen et al. |
| 5,693,043 A | 12/1997 | Kittrell et al. |
| 5,704,361 A | 1/1998 | Seward et al. |
| 5,707,352 A | 1/1998 | Sekins et al. |
| 5,720,287 A | 2/1998 | Chapelon et al. |
| 5,722,397 A | 3/1998 | Eppstein |
| 5,722,401 A | 3/1998 | Pietroski et al. |
| 5,762,066 A | 6/1998 | Law et al. |
| 5,767,692 A | 6/1998 | Antonello et al. |
| 5,772,590 A | 6/1998 | Webster, Jr. |
| 5,776,141 A | 7/1998 | Klein et al. |
| 5,779,715 A | 7/1998 | Tu |
| 5,782,760 A | 7/1998 | Schaer |
| 5,782,828 A | 7/1998 | Chen et al. |
| 5,782,900 A | 7/1998 | de la Rama et al. |
| 5,792,140 A | 8/1998 | Tu et al. |

(56) References Cited

U.S. PATENT DOCUMENTS

| | | |
|---|---|---|
| 5,792,187 A | 8/1998 | Adams |
| 5,797,960 A | 8/1998 | Stevens et al. |
| 5,800,392 A | 9/1998 | Racchini |
| 5,803,083 A * | 9/1998 | Buck et al. .............. 600/439 |
| 5,807,306 A | 9/1998 | Shapland et al. |
| 5,810,802 A | 9/1998 | Panescu et al. |
| 5,817,018 A | 10/1998 | Ohtomo |
| 5,824,087 A | 10/1998 | Aspden et al. |
| 5,840,031 A | 11/1998 | Crowley |
| 5,840,066 A | 11/1998 | Matsuda et al. |
| 5,840,076 A | 11/1998 | Swanson et al. |
| 5,843,020 A | 12/1998 | Tu et al. |
| 5,843,152 A | 12/1998 | Tu et al. |
| 5,848,969 A | 12/1998 | Panescu et al. |
| 5,849,028 A | 12/1998 | Chen |
| 5,853,368 A | 12/1998 | Solomon et al. |
| 5,860,974 A | 1/1999 | Abele |
| 5,861,021 A | 1/1999 | Thome et al. |
| 5,863,291 A | 1/1999 | Schaer |
| 5,865,787 A | 2/1999 | Shapland et al. |
| 5,865,801 A | 2/1999 | Houser |
| 5,868,708 A | 2/1999 | Hart et al. |
| 5,868,741 A | 2/1999 | Chia et al. |
| 5,868,779 A | 2/1999 | Ruiz |
| 5,871,449 A | 2/1999 | Brown |
| 5,876,340 A | 3/1999 | Tu et al. |
| 5,876,399 A | 3/1999 | Chia et al. |
| 5,882,333 A | 3/1999 | Schaer et al. |
| 5,891,027 A | 4/1999 | Tu et al. |
| 5,891,135 A | 4/1999 | Jackson |
| 5,891,137 A | 4/1999 | Chia et al. |
| 5,891,138 A | 4/1999 | Tu et al. |
| 5,893,885 A | 4/1999 | Webster, Jr. |
| 5,895,355 A | 4/1999 | Schaer |
| 5,897,554 A | 4/1999 | Chia et al. |
| 5,906,636 A | 5/1999 | Casscells, III et al. |
| 5,913,856 A | 6/1999 | Chia et al. |
| 5,916,170 A | 6/1999 | Kolz et al. |
| 5,916,213 A | 6/1999 | Haissaguerre et al. |
| 5,919,187 A | 7/1999 | Guglielmi et al. |
| 5,921,982 A | 7/1999 | Lesh et al. |
| 5,924,997 A | 7/1999 | Campbell |
| 5,931,811 A | 8/1999 | Haissaguerre |
| 5,935,063 A | 8/1999 | Nguyen |
| 5,935,075 A | 8/1999 | Casscells et al. |
| 5,938,660 A | 8/1999 | Swartz et al. |
| 5,941,845 A | 8/1999 | Tu et al. |
| 5,944,710 A | 8/1999 | Dev et al. |
| 5,951,471 A | 9/1999 | de la Rama et al. |
| 5,954,649 A | 9/1999 | Chia et al. |
| 5,954,710 A | 9/1999 | Paolini et al. |
| 5,954,719 A | 9/1999 | Chen et al. |
| 5,964,751 A | 10/1999 | Amplatz et al. |
| 5,971,968 A | 10/1999 | Tu et al. |
| 5,971,983 A | 10/1999 | Lesh |
| 5,972,026 A | 10/1999 | Laufer et al. |
| 5,980,515 A | 11/1999 | Tu |
| 6,002,955 A | 12/1999 | Willems et al. |
| 6,002,956 A | 12/1999 | Schaer |
| 6,004,269 A | 12/1999 | Crowley et al. |
| 6,006,123 A | 12/1999 | Nguyen et al. |
| 6,009,877 A | 1/2000 | Edwards |
| 6,011,995 A | 1/2000 | Guglielmi et al. |
| 6,012,457 A | 1/2000 | Lesh |
| 6,013,053 A | 1/2000 | Bower et al. |
| 6,016,437 A | 1/2000 | Tu et al. |
| 6,017,274 A | 1/2000 | Sherman et al. |
| 6,022,319 A | 2/2000 | Willard |
| 6,024,740 A | 2/2000 | Lesh |
| 6,026,326 A | 2/2000 | Bardy |
| 6,029,091 A | 2/2000 | de la Rama et al. |
| 6,033,402 A | 3/2000 | Tu et al. |
| 6,033,403 A | 3/2000 | Tu et al. |
| 6,041,252 A | 3/2000 | Walker et al. |
| 6,055,859 A | 5/2000 | Kozuka et al. |
| 6,056,744 A | 5/2000 | Edwards |
| 6,058,328 A | 5/2000 | Levine et al. |
| 6,059,423 A | 5/2000 | Knopick |
| 6,063,077 A | 5/2000 | Schaer |
| 6,064,902 A | 5/2000 | Haissaguerre |
| 6,066,134 A | 5/2000 | Eggers et al. |
| 6,068,629 A | 5/2000 | Haissaguerre et al. |
| 6,071,279 A | 6/2000 | Whayne et al. |
| 6,073,052 A | 6/2000 | Zelickson et al. |
| 6,080,151 A | 6/2000 | Swartz et al. |
| 6,083,255 A | 7/2000 | Laufer et al. |
| 6,094,988 A | 8/2000 | Aindow |
| 6,096,054 A | 8/2000 | Wyzgala et al. |
| 6,102,908 A | 8/2000 | Tu et al. |
| 6,106,474 A | 8/2000 | Koger et al. |
| 6,112,123 A | 8/2000 | Kelleher et al. |
| 6,117,101 A | 9/2000 | Diederich et al. |
| 6,123,456 A | 9/2000 | Lyons |
| 6,128,522 A | 10/2000 | Acker et al. |
| 6,135,999 A | 10/2000 | Fanton et al. |
| 6,146,379 A | 11/2000 | Fleischman |
| 6,149,620 A | 11/2000 | Baker et al. |
| 6,152,144 A | 11/2000 | Lesh et al. |
| 6,152,920 A | 11/2000 | Thompson |
| 6,161,543 A | 12/2000 | Cox et al. |
| 6,163,716 A | 12/2000 | Edwards |
| 6,164,283 A | 12/2000 | Lesh |
| 6,166,092 A | 12/2000 | Sekins et al. |
| 6,171,306 B1 | 1/2001 | Swanson et al. |
| 6,183,492 B1 | 2/2001 | Hart et al. |
| 6,190,353 B1 | 2/2001 | Makower et al. |
| 6,190,382 B1 | 2/2001 | Ormsby et al. |
| 6,193,713 B1 | 2/2001 | Geistert et al. |
| 6,196,059 B1 | 3/2001 | Kosslinger et al. |
| 6,197,023 B1 | 3/2001 | Muntermann |
| 6,200,269 B1 | 3/2001 | Lin et al. |
| 6,200,315 B1 | 3/2001 | Gaiser et al. |
| 6,200,333 B1 | 3/2001 | Laufer |
| 6,203,525 B1 | 3/2001 | Whayne |
| 6,203,531 B1 | 3/2001 | Ockuly et al. |
| 6,206,831 B1 | 3/2001 | Suorsa et al. |
| 6,208,142 B1 | 3/2001 | Wagshul |
| 6,210,356 B1 | 4/2001 | Anderson et al. |
| 6,212,426 B1 | 4/2001 | Swanson |
| 6,216,704 B1 | 4/2001 | Ingle et al. |
| 6,217,576 B1 | 4/2001 | Tu et al. |
| 6,221,070 B1 | 4/2001 | Tu et al. |
| 6,224,592 B1 | 5/2001 | Eggers et al. |
| 6,231,561 B1 | 5/2001 | Frazier et al. |
| 6,233,477 B1 | 5/2001 | Chia et al. |
| 6,235,025 B1 | 5/2001 | Swartz et al. |
| 6,237,605 B1 | 5/2001 | Vaska et al. |
| 6,238,335 B1 | 5/2001 | Silverman et al. |
| 6,238,390 B1 | 5/2001 | Tu et al. |
| 6,240,307 B1 | 5/2001 | Beatty et al. |
| 6,241,692 B1 | 6/2001 | Tu et al. |
| 6,241,726 B1 | 6/2001 | Chia et al. |
| 6,241,727 B1 | 6/2001 | Tu et al. |
| 6,241,754 B1 | 6/2001 | Swanson et al. |
| 6,245,026 B1 | 6/2001 | Campbell et al. |
| 6,245,064 B1 | 6/2001 | Lesh et al. |
| 6,245,067 B1 | 6/2001 | Tu et al. |
| 6,246,899 B1 | 6/2001 | Chia et al. |
| 6,246,912 B1 | 6/2001 | Sluijter |
| 6,246,914 B1 | 6/2001 | de la Rama et al. |
| 6,251,107 B1 | 6/2001 | Schaer |
| 6,251,109 B1 | 6/2001 | Hassett et al. |
| 6,251,130 B1 | 6/2001 | Dobak, III et al. |
| 6,254,598 B1 | 7/2001 | Edwards et al. |
| 6,254,599 B1 | 7/2001 | Lesh et al. |
| 6,259,941 B1 | 7/2001 | Chia et al. |
| 6,272,377 B1 | 8/2001 | Sweeney et al. |
| 6,273,886 B1 | 8/2001 | Edwards et al. |
| 6,273,907 B1 | 8/2001 | Laufer |
| 6,278,351 B1 | 8/2001 | Wheatley |
| 6,280,402 B1 | 8/2001 | Ishibashi et al. |
| 6,282,949 B1 | 9/2001 | Axelsson |
| 6,283,127 B1 | 9/2001 | Sterman et al. |
| 6,283,988 B1 | 9/2001 | Laufer et al. |

(56) References Cited

U.S. PATENT DOCUMENTS

| | | |
|---|---|---|
| 6,283,989 B1 | 9/2001 | Laufer et al. |
| 6,287,306 B1 | 9/2001 | Kroll et al. |
| 6,290,674 B1 | 9/2001 | Roue et al. |
| 6,290,697 B1 | 9/2001 | Tu et al. |
| 6,292,695 B1 | 9/2001 | Webster, Jr. et al. |
| 6,299,633 B1 | 10/2001 | Laufer |
| 6,302,875 B1 | 10/2001 | Makower et al. |
| 6,302,880 B1 | 10/2001 | Schaer |
| 6,305,378 B1 | 10/2001 | Lesh |
| 6,306,133 B1 | 10/2001 | Tu et al. |
| 6,308,090 B1 | 10/2001 | Tu et al. |
| 6,311,692 B1 | 11/2001 | Vaska et al. |
| 6,314,325 B1 | 11/2001 | Fitz |
| 6,314,962 B1 | 11/2001 | Vaska et al. |
| 6,314,963 B1 | 11/2001 | Vaska et al. |
| 6,315,778 B1 | 11/2001 | Gambale et al. |
| 6,321,121 B1 | 11/2001 | Zelickson et al. |
| 6,322,558 B1 | 11/2001 | Taylor et al. |
| 6,322,559 B1 | 11/2001 | Daulton et al. |
| 6,328,699 B1 | 12/2001 | Eigler et al. |
| 6,330,473 B1 | 12/2001 | Swanson et al. |
| 6,332,880 B1 | 12/2001 | Yang et al. |
| 6,347,247 B1 | 2/2002 | Dev et al. |
| 6,355,030 B1 | 3/2002 | Aldrich et al. |
| 6,355,051 B1 | 3/2002 | Sisskind et al. |
| 6,383,151 B1 | 5/2002 | Diederich et al. |
| 6,398,792 B1 | 6/2002 | O'Connor |
| 6,400,982 B2 | 6/2002 | Sweeney et al. |
| 6,411,852 B1 | 6/2002 | Danek et al. |
| 6,413,255 B1 | 7/2002 | Stem |
| 6,423,026 B1 | 7/2002 | Gesswein et al. |
| 6,427,089 B1 * | 7/2002 | Knowlton ............... 607/101 |
| 6,447,443 B1 | 9/2002 | Keogh et al. |
| 6,461,314 B1 | 10/2002 | Pant et al. |
| 6,466,811 B1 | 10/2002 | Hassett et al. |
| 6,475,146 B1 | 11/2002 | Frelburger et al. |
| 6,485,489 B2 | 11/2002 | Teirstein et al. |
| 6,488,673 B1 | 12/2002 | Laufer et al. |
| 6,488,679 B1 | 12/2002 | Swanson et al. |
| 6,491,710 B2 | 12/2002 | Satake |
| 6,492,762 B1 | 12/2002 | Pant et al. |
| 6,500,174 B1 | 12/2002 | Maguire et al. |
| 6,501,978 B2 | 12/2002 | Wagshul et al. |
| 6,506,189 B1 | 1/2003 | Rittman, III et al. |
| 6,508,774 B1 | 1/2003 | Acker et al. |
| 6,513,385 B1 | 2/2003 | Han et al. |
| 6,514,246 B1 | 2/2003 | Swanson et al. |
| 6,514,249 B1 | 2/2003 | Maguire et al. |
| 6,517,536 B2 | 2/2003 | Hooven et al. |
| 6,517,811 B2 | 2/2003 | John et al. |
| 6,522,930 B1 | 2/2003 | Schaer et al. |
| 6,527,769 B2 | 3/2003 | Langberg et al. |
| 6,536,949 B1 | 3/2003 | Hueser |
| 6,540,744 B2 | 4/2003 | Hassett et al. |
| 6,542,251 B2 | 4/2003 | Mueller-Rentz |
| 6,543,274 B1 | 4/2003 | Herrmann et al. |
| 6,547,788 B1 | 4/2003 | Maguire et al. |
| 6,564,096 B2 | 5/2003 | Mest |
| 6,589,274 B2 | 7/2003 | Stiger et al. |
| 6,595,934 B1 | 7/2003 | Hissong et al. |
| 6,595,989 B1 | 7/2003 | Schaer |
| 6,599,256 B1 | 7/2003 | Acker et al. |
| 6,599,288 B2 | 7/2003 | Maguire et al. |
| 6,601,459 B1 | 8/2003 | Jenni et al. |
| 6,605,084 B2 | 8/2003 | Acker et al. |
| 6,607,476 B1 | 8/2003 | Barnhart |
| 6,607,502 B1 | 8/2003 | Maguire et al. |
| 6,611,720 B2 | 8/2003 | Hata et al. |
| 6,613,045 B1 | 9/2003 | Laufer et al. |
| 6,615,071 B1 | 9/2003 | Casscells, III et al. |
| 6,622,041 B2 | 9/2003 | Terry, Jr. et al. |
| 6,622,731 B2 | 9/2003 | Daniel et al. |
| 6,626,855 B1 | 9/2003 | Weng et al. |
| 6,626,861 B1 | 9/2003 | Hart et al. |
| 6,626,899 B2 | 9/2003 | Houser et al. |
| 6,634,363 B1 | 10/2003 | Danek et al. |
| 6,635,054 B2 | 10/2003 | Fjield et al. |
| 6,641,579 B1 | 11/2003 | Bernardi et al. |
| 6,642,515 B1 | 11/2003 | Yamaguchi |
| 6,645,199 B1 | 11/2003 | Jenkens et al. |
| 6,645,202 B1 | 11/2003 | Pless et al. |
| 6,652,515 B1 | 11/2003 | Maguire et al. |
| 6,652,547 B2 | 11/2003 | Rabiner et al. |
| 6,654,636 B1 | 11/2003 | Dev et al. |
| 6,656,136 B1 | 12/2003 | Weng et al. |
| 6,656,174 B1 | 12/2003 | Hegde et al. |
| 6,658,279 B2 | 12/2003 | Swanson et al. |
| 6,660,013 B2 | 12/2003 | Rabiner et al. |
| 6,669,655 B1 | 12/2003 | Acker et al. |
| 6,669,687 B1 | 12/2003 | Saadat |
| 6,671,533 B2 | 12/2003 | Chen et al. |
| 6,671,556 B2 | 12/2003 | Osorio et al. |
| 6,672,312 B2 | 1/2004 | Acker |
| 6,695,782 B2 | 2/2004 | Ranucci et al. |
| 6,718,208 B2 | 4/2004 | Hill et al. |
| 6,719,694 B2 | 4/2004 | Weng et al. |
| 6,719,755 B2 | 4/2004 | Sliwa, Jr. et al. |
| 6,728,563 B2 | 4/2004 | Rashidi |
| 6,733,451 B2 | 5/2004 | Rabiner et al. |
| 6,735,471 B2 | 5/2004 | Hill et al. |
| 6,740,082 B2 | 5/2004 | Shadduck |
| 6,740,107 B2 | 5/2004 | Loeb et al. |
| 6,743,239 B1 | 6/2004 | Kuehn et al. |
| 6,752,805 B2 | 6/2004 | Maguire et al. |
| 6,758,830 B1 | 7/2004 | Schaer et al. |
| 6,763,722 B2 | 7/2004 | Fjield et al. |
| 6,764,486 B2 | 7/2004 | Natale |
| 6,786,904 B2 | 9/2004 | Doscher et al. |
| 6,787,974 B2 | 9/2004 | Fjield et al. |
| 6,799,064 B1 | 9/2004 | Hassett |
| 6,805,128 B1 | 10/2004 | Pless et al. |
| 6,808,524 B2 | 10/2004 | Lopath et al. |
| 6,837,886 B2 | 1/2005 | Collins et al. |
| 6,840,936 B2 | 1/2005 | Sliwa et al. |
| 6,845,267 B2 | 1/2005 | Harrison et al. |
| 6,850,801 B2 | 2/2005 | Kieval et al. |
| 6,862,479 B1 | 3/2005 | Whitehurst et al. |
| 6,866,760 B2 | 3/2005 | Paolini, Jr. et al. |
| 6,869,431 B2 | 3/2005 | Maguire et al. |
| 6,885,888 B2 | 4/2005 | Rezai |
| 6,929,608 B1 | 8/2005 | Hutchinson et al. |
| 6,936,046 B2 | 8/2005 | Hissong et al. |
| 6,936,047 B2 | 8/2005 | Nasab et al. |
| 6,939,309 B1 | 9/2005 | Beatty et al. |
| 6,939,346 B2 | 9/2005 | Kannenberg et al. |
| 6,947,785 B1 | 9/2005 | Beatty et al. |
| 6,960,207 B2 | 11/2005 | Vanney et al. |
| 6,964,660 B2 | 11/2005 | Maguire et al. |
| 6,966,908 B2 | 11/2005 | Maguire et al. |
| 6,969,388 B2 | 11/2005 | Goldman et al. |
| 6,976,492 B2 | 12/2005 | Ingle et al. |
| 6,978,174 B2 | 12/2005 | Gelfand et al. |
| 6,984,232 B2 | 1/2006 | Vanney et al. |
| 6,990,370 B1 | 1/2006 | Beatty et al. |
| 6,997,925 B2 | 2/2006 | Maguire et al. |
| 7,004,911 B1 | 2/2006 | Tu et al. |
| 7,027,869 B2 | 4/2006 | Danek et al. |
| 7,052,493 B2 | 5/2006 | Vaska et al. |
| 7,054,685 B2 | 5/2006 | Dimmer et al. |
| 7,063,679 B2 | 6/2006 | Maguire et al. |
| 7,081,114 B2 | 7/2006 | Rashidi |
| 7,081,115 B2 | 7/2006 | Taimisto |
| 7,082,336 B2 | 7/2006 | Ransbury et al. |
| 7,083,614 B2 | 8/2006 | Fjield et al. |
| 7,089,063 B2 | 8/2006 | Lesh et al. |
| 7,104,987 B2 | 9/2006 | Biggs et al. |
| 7,122,019 B1 | 10/2006 | Kesten et al. |
| 7,137,963 B2 | 11/2006 | Nita et al. |
| 7,155,284 B1 | 12/2006 | Whitehurst et al. |
| 7,156,816 B2 | 1/2007 | Schwartz et al. |
| 7,158,832 B2 | 1/2007 | Kieval et al. |
| 7,162,303 B2 | 1/2007 | Levin et al. |
| 7,189,203 B2 | 3/2007 | Lau et al. |
| 7,189,229 B2 | 3/2007 | Lopath et al. |

(56) References Cited

U.S. PATENT DOCUMENTS

| | | |
|---|---|---|
| 7,191,015 B2 | 3/2007 | Lamson et al. |
| 7,195,628 B2 | 3/2007 | Falkenberg |
| 7,198,635 B2 | 4/2007 | Danek et al. |
| 7,211,045 B2 | 5/2007 | Dala-Krishna et al. |
| 7,211,055 B2 | 5/2007 | Diederich et al. |
| 7,217,284 B2 | 5/2007 | Houser et al. |
| 7,229,437 B2 | 6/2007 | Johnson et al. |
| 7,229,469 B1 | 6/2007 | Witzel et al. |
| 7,263,397 B2 | 8/2007 | Hauck et al. |
| 7,269,453 B2 | 9/2007 | Mogul |
| 7,311,701 B2 | 12/2007 | Gifford et al. |
| 7,326,201 B2 | 2/2008 | Fjield et al. |
| 7,338,434 B1 | 3/2008 | Haarstad et al. |
| 7,340,307 B2 | 3/2008 | Maguire et al. |
| 7,347,852 B2 | 3/2008 | Hobbs et al. |
| 7,387,126 B2 | 6/2008 | Cox et al. |
| 7,387,629 B2 | 6/2008 | Vanney et al. |
| 7,425,212 B1 | 9/2008 | Danek et al. |
| 7,444,183 B2 | 10/2008 | Knudson et al. |
| 7,503,895 B2 | 3/2009 | Rabiner et al. |
| 7,507,235 B2 | 3/2009 | Keogh et al. |
| 7,529,582 B1 | 5/2009 | DiLorenzo |
| 7,529,589 B2 | 5/2009 | Williams et al. |
| 7,540,846 B2 | 6/2009 | Harhen et al. |
| 7,573,182 B2 | 8/2009 | Savage |
| 7,599,736 B2 | 10/2009 | DiLorenzo |
| 7,616,997 B2 | 11/2009 | Kieval et al. |
| 7,617,005 B2 | 11/2009 | Demarais et al. |
| 7,620,451 B2 | 11/2009 | Demarais et al. |
| 7,621,902 B2 | 11/2009 | Nita et al. |
| 7,625,371 B2 | 12/2009 | Morris et al. |
| 7,647,115 B2 | 1/2010 | Levin et al. |
| 7,653,438 B2 | 1/2010 | Deem et al. |
| 7,670,297 B1 | 3/2010 | Hauck et al. |
| 7,706,882 B2 | 4/2010 | Francischelli et al. |
| RE41,334 E | 5/2010 | Beatty et al. |
| 7,717,948 B2 | 5/2010 | Demarais et al. |
| 7,756,583 B2 | 7/2010 | Demarais et al. |
| 7,819,826 B2 | 10/2010 | Diederich et al. |
| 7,819,866 B2 | 10/2010 | Bednarek |
| 7,824,341 B2 | 11/2010 | Krishnan |
| 7,837,676 B2 | 11/2010 | Sinelnikov et al. |
| 7,873,417 B2 | 1/2011 | Demarais et al. |
| 7,881,809 B2 | 2/2011 | Rashidi |
| 7,955,293 B2 | 6/2011 | Nita et al. |
| 8,116,883 B2 | 2/2012 | Williams et al. |
| 8,131,371 B2 | 3/2012 | Demarals et al. |
| 8,131,372 B2 | 3/2012 | Levin et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,233,221 B2 | 7/2012 | Suijver et al. |
| 8,251,986 B2 | 8/2012 | Chornenky et al. |
| 8,287,472 B2 | 10/2012 | Ostrovsky et al. |
| 8,347,891 B2 | 1/2013 | Demarais et al. |
| 8,475,442 B2 | 7/2013 | Hall et al. |
| 8,485,993 B2 | 7/2013 | Orszulak et al. |
| 8,504,147 B2 | 8/2013 | Deem et al. |
| D697,036 S | 1/2014 | Kay et al. |
| 8,715,209 B2 | 5/2014 | Gertner |
| 8,734,438 B2 | 5/2014 | Behnke |
| D708,810 S | 7/2014 | Lewis, Jr. |
| 8,808,345 B2 | 8/2014 | Clark et al. |
| D712,352 S | 9/2014 | George et al. |
| D712,353 S | 9/2014 | George et al. |
| D712,833 S | 9/2014 | George et al. |
| 8,974,445 B2 | 3/2015 | Warnking et al. |
| 2001/0007070 A1 | 7/2001 | Stewart et al. |
| 2001/0007940 A1* | 7/2001 | Tu et al. .................... 606/41 |
| 2001/0044625 A1 | 11/2001 | Hata et al. |
| 2002/0002329 A1 | 1/2002 | Avitall |
| 2002/0002371 A1 | 1/2002 | Acker et al. |
| 2002/0019627 A1 | 2/2002 | Maguire et al. |
| 2002/0065512 A1 | 5/2002 | Fjield et al. |
| 2002/0065541 A1 | 5/2002 | Fredricks et al. |
| 2002/0068885 A1 | 6/2002 | Harhen et al. |
| 2002/0082594 A1 | 6/2002 | Hata et al. |
| 2002/0087156 A1 | 7/2002 | Maguire et al. |
| 2002/0151889 A1 | 10/2002 | Swanson et al. |
| 2002/0165532 A1 | 11/2002 | Hill et al. |
| 2002/0165535 A1* | 11/2002 | Lesh et al. .................... 606/41 |
| 2002/0183682 A1 | 12/2002 | Darvish et al. |
| 2003/0013968 A1 | 1/2003 | Fjield et al. |
| 2003/0018367 A1 | 1/2003 | DiLorenzo |
| 2003/0036705 A1 | 2/2003 | Hare et al. |
| 2003/0050632 A1 | 3/2003 | Fjield et al. |
| 2003/0050637 A1 | 3/2003 | Maguire et al. |
| 2003/0050681 A1 | 3/2003 | Pianca et al. |
| 2003/0055422 A1 | 3/2003 | Lesh |
| 2003/0065263 A1 | 4/2003 | Hare et al. |
| 2003/0069570 A1 | 4/2003 | Witzel et al. |
| 2003/0109778 A1 | 6/2003 | Rashidi |
| 2003/0114901 A1 | 6/2003 | Leob et al. |
| 2003/0125790 A1 | 7/2003 | Fastovsky et al. |
| 2003/0150464 A1 | 8/2003 | Casscells |
| 2003/0158584 A1 | 8/2003 | Cates et al. |
| 2003/0181897 A1 | 9/2003 | Thomas et al. |
| 2003/0181963 A1 | 9/2003 | Pellegrino et al. |
| 2003/0199747 A1 | 10/2003 | Michlitsch et al. |
| 2003/0199767 A1 | 10/2003 | Cespedes et al. |
| 2003/0199768 A1 | 10/2003 | Cespedes et al. |
| 2003/0199863 A1 | 10/2003 | Swanson et al. |
| 2003/0204138 A1* | 10/2003 | Choi .......................... 600/434 |
| 2003/0216721 A1 | 11/2003 | Diederich et al. |
| 2003/0216792 A1 | 11/2003 | Levin et al. |
| 2003/0216794 A1 | 11/2003 | Becker et al. |
| 2003/0225331 A1* | 12/2003 | Diederich et al. .......... 600/437 |
| 2003/0233099 A1 | 12/2003 | Danaek et al. |
| 2003/0236443 A1 | 12/2003 | Cespedes et al. |
| 2003/0236539 A1 | 12/2003 | Rabiner et al. |
| 2004/0010289 A1 | 1/2004 | Biggs et al. |
| 2004/0054362 A1 | 3/2004 | Lopath et al. |
| 2004/0064090 A1 | 4/2004 | Keren et al. |
| 2004/0064091 A1 | 4/2004 | Keren et al. |
| 2004/0068257 A1 | 4/2004 | Lopath et al. |
| 2004/0082859 A1 | 4/2004 | Schaer |
| 2004/0097996 A1 | 5/2004 | Rabiner et al. |
| 2004/0101523 A1 | 5/2004 | Reitz et al. |
| 2004/0127942 A1 | 7/2004 | Yomtov et al. |
| 2004/0158151 A1 | 8/2004 | Ranucci et al. |
| 2004/0162590 A1 | 8/2004 | Whitehurst et al. |
| 2004/0176699 A1 | 9/2004 | Walker et al. |
| 2004/0176757 A1 | 9/2004 | Sinelnikov et al. |
| 2004/0215186 A1 | 10/2004 | Cornelius et al. |
| 2004/0243102 A1 | 12/2004 | Berg et al. |
| 2004/0243206 A1 | 12/2004 | Tadlock |
| 2004/0249416 A1 | 12/2004 | Yun et al. |
| 2004/0260278 A1 | 12/2004 | Anderson et al. |
| 2005/0010263 A1 | 1/2005 | Schauerte |
| 2005/0010270 A1 | 1/2005 | Laufer |
| 2005/0165391 A1 | 7/2005 | Maguire et al. |
| 2005/0171575 A1 | 8/2005 | Dev et al. |
| 2005/0187579 A1 | 8/2005 | Danek et al. |
| 2005/0192638 A1 | 9/2005 | Gelfand et al. |
| 2005/0209548 A1 | 9/2005 | Dev et al. |
| 2005/0228459 A1 | 10/2005 | Levin et al. |
| 2005/0234523 A1 | 10/2005 | Levin et al. |
| 2005/0240170 A1 | 10/2005 | Zhang et al. |
| 2005/0240241 A1 | 10/2005 | Yun et al. |
| 2005/0245892 A1 | 11/2005 | Elkins et al. |
| 2005/0256518 A1 | 11/2005 | Rama et al. |
| 2005/0288730 A1 | 12/2005 | Deem et al. |
| 2006/0009753 A1 | 1/2006 | Fjield et al. |
| 2006/0025821 A1 | 2/2006 | Gelfand et al. |
| 2006/0041277 A1 | 2/2006 | Deem et al. |
| 2006/0058711 A1 | 3/2006 | Harhen et al. |
| 2006/0089674 A1 | 4/2006 | Walters et al. |
| 2006/0100514 A1 | 5/2006 | Lopath |
| 2006/0100667 A1 | 5/2006 | Machado et al. |
| 2006/0111754 A1 | 5/2006 | Rezai et al. |
| 2006/0121610 A1 | 6/2006 | Rubinsky et al. |
| 2006/0142801 A1 | 6/2006 | Demarais et al. |

(56) References Cited

U.S. PATENT DOCUMENTS

| | | |
|---|---|---|
| 2006/0149350 A1 | 7/2006 | Patel et al. |
| 2006/0155269 A1 | 7/2006 | Warnking |
| 2006/0155344 A1 | 7/2006 | Rezai et al. |
| 2006/0167437 A1 | 7/2006 | Valencia |
| 2006/0167498 A1 | 7/2006 | DiLorenzo |
| 2006/0167499 A1 | 7/2006 | Palti |
| 2006/0189941 A1 | 8/2006 | Seward et al. |
| 2006/0189960 A1 | 8/2006 | Kesten et al. |
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0229594 A1 | 10/2006 | Francischelli et al. |
| 2006/0235474 A1 | 10/2006 | Demarais |
| 2006/0241523 A1 | 10/2006 | Sinelnikov et al. |
| 2006/0265014 A1 | 11/2006 | Demarais et al. |
| 2006/0265015 A1 | 11/2006 | Demarais et al. |
| 2006/0270976 A1 | 11/2006 | Savage et al. |
| 2006/0271111 A1 | 11/2006 | Demarais et al. |
| 2006/0276852 A1 | 12/2006 | Demarais et al. |
| 2007/0066972 A1 | 3/2007 | Ormsby et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0173899 A1 | 7/2007 | Levin et al. |
| 2007/0244479 A1 | 10/2007 | Beatty et al. |
| 2007/0255267 A1 | 11/2007 | Diederich et al. |
| 2007/0265609 A1 | 11/2007 | Thapliyal et al. |
| 2007/0265610 A1 | 11/2007 | Thapliyal et al. |
| 2007/0265687 A1 | 11/2007 | Deem et al. |
| 2007/0282407 A1 | 12/2007 | Clark |
| 2008/0108988 A1 | 5/2008 | Edwards |
| 2008/0140150 A1 | 6/2008 | Zhou et al. |
| 2008/0213331 A1 | 9/2008 | Gelfand et al. |
| 2008/0255449 A1 | 10/2008 | Warnking et al. |
| 2009/0036948 A1 | 2/2009 | Levin et al. |
| 2009/0062697 A1 | 3/2009 | Zhang et al. |
| 2009/0149753 A1 | 6/2009 | Govari et al. |
| 2009/0171202 A1 | 7/2009 | Kirkpatrick et al. |
| 2009/0216286 A1 | 8/2009 | DiLorenzo |
| 2009/0221939 A1 | 9/2009 | Demarais et al. |
| 2009/0228003 A1 | 9/2009 | Sinelnikov |
| 2009/0306739 A1 | 12/2009 | DiLorenzo |
| 2009/0312673 A1 | 12/2009 | Thapliyal et al. |
| 2009/0312693 A1 | 12/2009 | Thapliyal et al. |
| 2009/0312755 A1 | 12/2009 | Thapliyal et al. |
| 2010/0016762 A1 | 1/2010 | Thapliyal et al. |
| 2010/0049099 A1 | 2/2010 | Thapliyal et al. |
| 2010/0057150 A1 | 3/2010 | Demarais et al. |
| 2010/0113928 A1 | 5/2010 | Thapliyal et al. |
| 2010/0113985 A1 | 5/2010 | Thapliyal et al. |
| 2010/0125198 A1 | 5/2010 | Thapliyal et al. |
| 2010/0130892 A1 | 5/2010 | Warnking |
| 2010/0137860 A1 | 6/2010 | Demarais et al. |
| 2010/0137952 A1 | 6/2010 | Demarais et al. |
| 2010/0152582 A1 | 6/2010 | Thapliyal et al. |
| 2010/0174282 A1 | 7/2010 | Demarais et al. |
| 2010/0179424 A1 | 7/2010 | Warnking et al. |
| 2010/0191112 A1 | 7/2010 | Demarais et al. |
| 2010/0198065 A1 | 8/2010 | Thapliyal et al. |
| 2010/0222851 A1 | 9/2010 | Deem et al. |
| 2010/0222854 A1 | 9/2010 | Demarais et al. |
| 2010/0268307 A1 | 10/2010 | Demarais et al. |
| 2011/0079230 A1 | 4/2011 | Danek et al. |
| 2011/0087096 A1 | 4/2011 | Behar |
| 2011/0087097 A1 | 4/2011 | Behar |
| 2011/0118632 A1 | 5/2011 | Sinelnikov et al. |
| 2011/0137298 A1 | 6/2011 | Nguyen et al. |
| 2011/0172527 A1 | 7/2011 | Gertner |
| 2011/0178516 A1 | 7/2011 | Orszulak et al. |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0237983 A1 | 9/2011 | Nita et al. |
| 2011/0257523 A1 | 10/2011 | Hastings et al. |
| 2011/0257563 A1 | 10/2011 | Thapliyal et al. |
| 2011/0257564 A1 | 10/2011 | Demarais et al. |
| 2011/0319765 A1 | 12/2011 | Gertner et al. |
| 2012/0065493 A1 | 3/2012 | Gertner |
| 2012/0065554 A1 | 3/2012 | Pikus |
| 2012/0095461 A1 | 4/2012 | Herscher et al. |
| 2012/0123243 A1 | 5/2012 | Hastings |
| 2012/0123303 A1 | 5/2012 | Sogard et al. |
| 2012/0143097 A1 | 6/2012 | Pike, Jr. |
| 2012/0165667 A1 | 6/2012 | Altmann et al. |
| 2012/0172723 A1 | 7/2012 | Gertner |
| 2012/0232436 A1 | 9/2012 | Warnking |
| 2012/0238918 A1 | 9/2012 | Gertner |
| 2012/0238919 A1 | 9/2012 | Gertner |
| 2012/0265198 A1 | 10/2012 | Crow et al. |
| 2012/0316439 A1 | 12/2012 | Behar |
| 2013/0012844 A1 | 1/2013 | Demarais et al. |
| 2013/0072928 A1 | 3/2013 | Schaer |
| 2013/0090650 A1 | 4/2013 | Jenson et al. |
| 2013/0103064 A1 | 4/2013 | Arenson et al. |
| 2013/0110012 A1 | 5/2013 | Gertner |
| 2013/0131668 A1 | 5/2013 | Schaer |
| 2013/0138018 A1 | 5/2013 | Gertner |
| 2013/0158441 A1 | 6/2013 | Demarais et al. |
| 2013/0158442 A1 | 6/2013 | Demarais et al. |
| 2013/0165822 A1 | 6/2013 | Demarais et al. |
| 2013/0165924 A1 | 6/2013 | Mathur et al. |
| 2013/0197555 A1 | 8/2013 | Schaer |
| 2013/0204167 A1 | 8/2013 | Sverdlik et al. |
| 2013/0211396 A1 | 8/2013 | Sverdlik et al. |
| 2013/0211437 A1 | 8/2013 | Sverdlik et al. |
| 2013/0218054 A1 | 8/2013 | Sverdlik et al. |
| 2013/0274658 A1 | 10/2013 | Steinke et al. |
| 2013/0282084 A1 | 10/2013 | Mathur et al. |
| 2013/0304047 A1 | 11/2013 | Grunewald et al. |
| 2013/0331739 A1 | 12/2013 | Gertner |
| 2014/0012133 A1 | 1/2014 | Sverdlik et al. |
| 2014/0018794 A1 | 1/2014 | Anderson et al. |
| 2014/0025069 A1 | 1/2014 | Willard et al. |
| 2014/0031727 A1 | 1/2014 | Warnking |
| 2014/0039477 A1 | 2/2014 | Sverdlik et al. |
| 2014/0046313 A1 | 2/2014 | Pederson et al. |
| 2014/0067029 A1 | 3/2014 | Schauer et al. |
| 2014/0074083 A1 | 3/2014 | Horn et al. |
| 2014/0107639 A1 | 4/2014 | Zhang et al. |
| 2014/0163540 A1 | 6/2014 | Iyer et al. |
| 2014/0180196 A1 | 6/2014 | Stone et al. |
| 2014/0180197 A1 | 6/2014 | Sverdlik et al. |
| 2014/0194785 A1 | 7/2014 | Gertner |
| 2014/0200489 A1 | 7/2014 | Behar et al. |
| 2014/0214018 A1 | 7/2014 | Behar et al. |
| 2014/0249524 A1 | 9/2014 | Kocur |
| 2014/0272110 A1 | 9/2014 | Taylor et al. |
| 2014/0275924 A1 | 9/2014 | Min et al. |
| 2014/0276742 A1 | 9/2014 | Nabutovsky et al. |
| 2014/0276752 A1 | 9/2014 | Wang et al. |
| 2014/0276755 A1 | 9/2014 | Cao et al. |
| 2014/0276789 A1 | 9/2014 | Dandler et al. |
| 2014/0277033 A1 | 9/2014 | Taylor et al. |
| 2015/0223877 A1 | 8/2015 | Behar et al. |
| 2015/0290427 A1 | 10/2015 | Warnking |
| 2015/0335919 A1 | 11/2015 | Behar et al. |
| 2016/0016016 A1 | 1/2016 | Taylor et al. |

FOREIGN PATENT DOCUMENTS

| | | |
|---|---|---|
| EP | 0 767 630 B1 | 4/1997 |
| EP | 0 774 276 | 5/1997 |
| EP | 1042990 | 10/2000 |
| EP | 1 100 375 B1 | 5/2001 |
| EP | 1 384 445 | 1/2004 |
| EP | 1598024 | 11/2005 |
| EP | 1 647 305 B1 | 4/2006 |
| EP | 2 218 479 A2 | 8/2010 |
| EP | 2 457 614 A1 | 5/2012 |
| EP | 2 460 486 B1 | 6/2012 |
| EP | 2 495 012 B1 | 9/2012 |
| EP | 2 521 593 B1 | 11/2012 |
| EP | 2 561 903 A1 | 2/2013 |
| EP | 2 561 905 A1 | 2/2013 |

(56) References Cited

FOREIGN PATENT DOCUMENTS

| | | |
|---|---|---|
| EP | 2 626 022 A2 | 8/2013 |
| EP | 2 632 373 | 9/2013 |
| EP | 2 662 041 A2 | 11/2013 |
| EP | 2 662 043 A2 | 11/2013 |
| GB | 2037166 | 7/1980 |
| JP | 07-178173 | 7/1995 |
| JP | 10-127678 | 5/1998 |
| JP | 11-218100 | 8/1999 |
| JP | 2002-078809 | 3/2002 |
| WO | WO 90/00420 | 1/1990 |
| WO | WO 92/07622 | 5/1992 |
| WO | WO 92/20291 | 11/1992 |
| WO | WO 94/05365 | 3/1994 |
| WO | WO 94/11057 | 5/1994 |
| WO | WO 95/19143 | 7/1995 |
| WO | WO 95/25472 | 9/1995 |
| WO | WO 96/00039 | 1/1996 |
| WO | WO 97/13463 | 4/1997 |
| WO | WO 97/36548 | 10/1997 |
| WO | WO 98/41178 | 9/1998 |
| WO | WO 98/42403 | 10/1998 |
| WO | WO 98/49957 | 11/1998 |
| WO | WO 98/52465 | 11/1998 |
| WO | WO 99/02096 | 1/1999 |
| WO | WO 99/35987 | 7/1999 |
| WO | WO 99/44519 | 9/1999 |
| WO | WO-99/44523 | 9/1999 |
| WO | WO 99/44523 | 9/1999 |
| WO | WO 99/52423 | 10/1999 |
| WO | WO 99/56812 | 11/1999 |
| WO | WO 00/16850 | 3/2000 |
| WO | WO 00/27292 | 5/2000 |
| WO | WO 00/42934 | 7/2000 |
| WO | WO 00/51511 | 9/2000 |
| WO | WO 00/51683 | 9/2000 |
| WO | WO 00/56237 | 9/2000 |
| WO | WO 00/57495 | 9/2000 |
| WO | WO 00/67648 | 11/2000 |
| WO | WO 00/67656 | 11/2000 |
| WO | WO 00/67830 | 11/2000 |
| WO | WO 00/67832 | 11/2000 |
| WO | WO 01/13357 | 2/2001 |
| WO | WO 01/22897 | 4/2001 |
| WO | WO 01/70114 | 9/2001 |
| WO | WO 01/80723 A2 | 11/2001 |
| WO | WO 01/82814 | 11/2001 |
| WO | WO 01/37925 | 12/2001 |
| WO | WO 02/05868 | 1/2002 |
| WO | WO 01/80723 A3 | 4/2002 |
| WO | WO 02/083196 | 10/2002 |
| WO | WO 02/085192 | 10/2002 |
| WO | WO 03/003930 | 1/2003 |
| WO | WO-03/059437 A2 | 7/2003 |
| WO | WO 2004/023978 | 3/2004 |
| WO | WO-2006/041881 A2 | 4/2006 |
| WO | WO 2012/112165 | 8/2012 |
| WO | WO-2012/112165 A1 | 8/2012 |

OTHER PUBLICATIONS

Arruda, M. S., et al. "Development and validation of an ECG algorithm for identifying accessory pathway ablation site in Wolff-ParkinsonWhite syndrome." J Cardiovasc Electrophysiol, 9:2-12 (1998).

Avitall, B., et al. "The creation of linear continuous lesions in the atria with an expandable loop catheter." J Am Coll Cardiol, 33,4:972-984 (1999).

Bartlett, T. G., et al. "Current management of the Wolff-Parkinson-White syndrome." J Card Surg, 8:503-515 (1993).

Benito, F., et al. "Radio frequency catheter ablation of accessory pathways in infants," Heart, 78: 160-162 (1997).

Blumenfeld, J. D., et al. "β-Adrenergic receptor blockade as a therapeutic approach for suppressing the renin-angiotensin-aldosterone system in norrnotensive and hypertensive subjects." AJH, 12:451-459 (1999).

Callans, D. J. "Narrowing ofthe superior vena cava-right atrium junction during radiofrequency catheter ablation for inappropriate sinus tachycardia: Analysis with intracardiac echocardiography." JACC, 33:1667-1670 (1999).

Cao, H., et al. "Flow effect on lesion formation in RF cardiac catheter ablation." IEEE T Bio-Med Eng, 48:425-433 (2001).

Chen, Shih-Ann, M.D., "Initiation of Atrial Fibrillation by Ectopic Beats Originating From the Pulmonary Veins," Circulation 100(18):1879-86, (1999).

Chen, S.-A., et al. "Complications of diagnostic electrophysiologic studies and radiofrequency catheter ablation in patients with tachyarrhythmias: An eight-year survey of 3,966 consecutive procedures in a tertiary referral center." Am J Cardiol, 77 :41-46 (1996).

Chinitz, Larry A., "Mapping Reentry Around Atriotomy Scars Using Double Potentials," PACE, 19:1978-1983 (1996).

Cioni, R., et al. "Renal artery stenting in patients with a solitary functioning kidney." Cardiovasc Intervent Radiol, 24:372-377 (2001).

Cosby, R. L., et al. "The role of the sympathetic nervous system and vasopressin in the pathogenesis of the abnormal sodium and water." *Nefrologia*, V, 4:271-277 (1985).

Cosio, Francisco G., "Atrial Flutter Mapping and Ablation II," Pacing & Clin. Electrophysiol. 19(6):965-75, (1996).

Cox, J. L. "The status of surgery for cardiac arrhythmias." Circulation, 71 :413-417 (1985).

Cox, J. L., et al. "Five-year experience with the Maze procedure for atrial fibrillation." Ann Thorac Surg, 56:814-824 (1993).

Cruickshank, J. M. "Beta-blockers continue to surprise us." Eur Heart J, 21:354-364 (2000).

Curtis, J. J., et al. "Surgical therapy for persistent hypertension after renal transplantation," Transplantation, 31:125-128 (1981).

Demazumder, D., et al. "Comparison of irrigated electrode designs for radiofrequency ablation of myocardium." J Interv Card Electr, 5:391-400 (2001).

DiBona, G. F. "Neural control of the kidney: Functionally specific renal sympathetic nerve fibers." Am J Physiol Regulatory Integrative Comp Physiol, 279:R1517-R1524 (2000).

DiBona, G. F. "Sympathetic nervous system and kidney in hypertension," Nephrol and Hypertension, 11: 197-200 (2002).

DiBona, G. F., et al. "Neural control of renal function," Physiol Rev, 77:75-197 (1997).

DiBona, G. F., et al. "Renal hemodynamic effects of activation of specific renal sympathetic nerve fiber groups." Am J Physiol Regul Integr Comp Physiol, 276:R539-R549 (1999).

Doggrell, S. A., et al. "Rat models of hypertension, cardiac hypertrophy and failure." Cardiovasc Res, 39:89-105 (1998).

Dong, Q., et al. "Diagnosis ofrenal vascular disease with MR angiography." RadioGraphies, 19:1535-1554 (1999).

Dubuc, M., et al. "Feasibility of cardiac cryoablation using a transvenous steerable electrode catheter," J Interv Cardiac Electrophysiol, 2:285-292 (1998).

Feld, Gregory K., "Radiofrequency Catheter Ablation for the Treatment of Human Type I Atrial Flutter," Circulation, 86:1233-1240 (1992).

Gallagher, John J., "Wolff-Parkinson-White Syndrome: Surgery to Radiofrequency Catheter Ablation," PACE, 20:512-533 (1997).

Gilard, M., et al. "Angiographic anatomy ofthe coronary sinus and its tributaries." PACE, 21:2280-2284 (1998).

Goriseh, W., et al. "Heat-indueed contraction of blood vessels." Lasers Surg Med, 2:1-13 (1982).

Haines, D. E., et al. "Tissue heating during radiofrequeney catheter ablation; A thermodynamic model and observations in isolated perfused and superfused canine right ventrieular free wall." PACE, 12:962-976 (1989).

Haissaguerre, Michel, "Electrophysiological End Point for Catheter Ablation of Atrial Fibrillation Initiated From Multiple Venous Foci," Circulation, 101:1409-1417 (2000).

Haissaguerre, Michel, M.D., "Predominant Origin of Atrial Panarrythmic Triggers in the Pulmonary Veins: A Distinct Electrophysiologic Entity," PACE, 20:1065 (1997).

(56) References Cited

OTHER PUBLICATIONS

Haissaguerre, Michel, M.D., "Radiofrequency Catheter Ablation in Unusual Mechanisms of Atrial Fibrillation," J Cardiovasc Electrophysiol, 5:743-751 (1994).
Haissaguerre, Michel, M.D., "Right and Left Atrial Radiofrequency Catheter Therapy of Paroxysmal Atrial Fibrillation," J Cardiovasc Electrophysiol, 7:1132-1144 (1996).
Haissaguerre, Michel, M.D., "Spontaneous Initiation of Atrial Fibrillation by Ectopic Beats Originating in the Pulmonary Veins," N England J Med, 339, 10:659-666 (1998).
Han, Y-M., et al. "Renal artery embolization with diluted hot contrast medium: An experimental study," J Vasc Interv Radiol, 12:862-868 (2001).
Hansen, J. M., et al. "The transplanted human kidney does not achieve functional reinnervation." Clin Sci, 87, 1: 13-20 (1994).
Hatala, Robert, "Radiofrequency Catheter Ablation of Left Atrial Tachycardia Originating Within the Pulmonary Vein in a Patient with Dextrocardia," PACE, 19:999-1002 (1996).
Hindricks, G. "The Multicentre European Radiofrequency Survey (MERFS): Complications of radiofrequency catheter ablation of arrhythmias." Eur Heart J, 14:1644-1653 (1993).
Ho, S. Y., et al. "Architecture ofthe pulmonary veins: Relevance to radiofrequency ablation." Heart, 86:265-270 (2001).
Hocini, Meleze, "Concealed Left Pulmonary Vein Potentials Unmasked by Left Atrial Stimulation," PACE, 23:1832-1835 (2000).
Hocini, Meleze, "Multiple Sources Initating Atrial Fibrillation from a Single Pulmonary Vein Identified by a Circumferential Catheter," PACE, 23:1828-1831 (2000).
Hsieh, Ming-Hsiung, M.D., "Double Multielectrode Mapping Catheters Facilitate Radiofrequency Catheter Ablation of Focal Atrial Fibrillation Originating from Pulmonary Veins," J Cardiovasc Electrophysiol, 10:136-144 (1998).
Huang et al., "Renal denervation prevents and reverses hyperinsulinemia-induced hypertension in rats," Hypertension 32, pp. 249-254 (1998).
Huang, S. K. S., et al. "Radiofrequency catheter ablation of cardiac arrhythmias: Basic concepts and clinical applications." 2nd ed. Armonk, NY: Futura Publishing Co. (2000).
Jackman, W. M., et al. "Treatment of supraventricular tachycardia due to atrioventricular nodal reentry by radiofrequency catheter ablation of slow-pathway conduction." N England J Med, 327, 5:313-318 (Jul. 30, 1992).
Jain, M. K., et al. "A three-dimensional finite element model of radiofrequency ablation with blood flow and its experimental validation." Ann Biomed Eng, 28:1075-1084 (2000).
Jais, Pierre, M.D., "A Focal Source of Atrial Fibrillation Treated by Discrete Radiofrequency Ablation," Circulation, 95(3): 572-576 (1996).
Janssen, B. J. A., et al. "Renal nerves in hypertension." Miner Electrolyte Metab, 15:74-82 (1989).
Kapural, L., et al. "Radiofrequency ablation for chronic pain control." Curr Pain Headache Rep, 5:517-525 (2001).
Kay, G. Neal, "Radiofrequency Ablation for Treatment of Primary Atrial Tachycardia," JACC 21:901-909 (1993).
Koepke, J. P., et al. "The physiology teacher: Functions ofthe renal nerves." The Physiologist, 28, 1 :47-52 (1985).
Kompanowska, E., et al. "Early effects of renal denervation in the anaesthetised rat: Natriuresis and increased cortical blood flow," J Physiol, 531.2:527-534 (2001).
Krimholtz et al., "New Equivalent Circuits for Elementary Piezoelectric Transducers," Electronics Lettres, vol. 6, No. 13, pp. 398-399, Jun. 25, 1970.
Kumagai, Koichiro, "Treatment of Mixed Atrial Fibrillation and Typical Atrial Flutter by Hybrid Catheter Ablation," PACE 23: 1839-1842 (2000).
Labonte, S. "Numerieal model for radio-frequency ablation of the endocardium and its experimental validation." IEEE T Bio-med Eng, 41,2:108-115 (1994).

Lee, S.-J., et al. "Ultrasonic energy in endoscopic surgery," Yonsei Med J, 40:545-549 (1999).
Leertouwer, T. c., et al. "In-vitro validation, with histology, of intravascular ultrasound in renal arteries." J Hypertens, 17:271-277 (1999).
Lesh, M.D., "An Anatomic Approach to Prevention of Atrial Fibrillation: Pulmonary Vein Isolation with Through-the-Balloon Ultrasound Ablation (TTB-US)," Thorac. Cardiovasc. Surg. 47 (1999) (Suppl.) 347-51.
Lesh, Michael D., M.D., "Radiofrequency Catheter Ablation of Atrial Arrhythmias," 1994.
Liem, L. Bing, "In Vitro and In Vivo Results of Transcatheter Microwave Ablation Using Forward-Firing Tip Antenna Design," 1996.
Lin, Wei-Shiang, M.D., "Pulmonary Vein Morphology in Patients with Paroxysmal Atrial Fibrillation Initiated by Ectopic Beats Originating From the Pulmonary Veins," Circulation 101(11):1274-81, 2000.
Lowe, J. E. "Surgical treatment of the Wolff-Parkinson-White syndrome and other supraventricular tachyarrhythmias." J Card Surg, 1 :117-134 (1986).
Lundin, S. et al. "Renal sympathetic activity in spontaneously hypertensive rats and normotensive controls, as studied by three different methods." Acta Physiol Scand, 120,2:265-272 (1984).
Lustgarten, D. L., et al. "Cryothermal ablation: Mechanism of tissue injury and current experience in the treatment of tachyarrhythmias," Progr Cardiovasc Dis, 41:481-498 (1999).
Mallavarapu, Christopher, "Radiofrequency Catheter Ablation of Atrial Tachycardia with Unusual Left Atrial Sites of Origin," 1996.
McRury, I. D., et al. "Nonunifonn heating during radiofrequency catheter ablation with long electrodes." Circulation, 96:4057-4064 (1997).
Mehdirad, A., et al. "Temperature controlled RF ablation in canine ventricle and coronary sinus using 7 Fr or 5 Fr ablation electrodes." PACE, 21:310-321 (1998).
Miller, B. F., and Keane, C. B. "Miller-Keane Encyclopedia & Dictionary 0/ Medicine, Nursing, & Allied Health." Philadelphia: Saunders (1997) ("ablation").
Misaki, T., et al. "Surgical treatment ofpatients with Wolff-ParkinsonWhite syndrome and associated Ebstein's anomaly." J Thorae Cardiovase Surg, 110: 1702-1707 (1995).
Moak, J. P., et al. "Case report: Pulmonary vein stenosis following RF ablation of paroxysmal atrial fibrillation: Successful treatment with balloon dilation." J Interv Card Electrophys, 4:621-631 (2000).
Montenero, Sandro, Annibale, "Electrograms for Identification of the Atrial Ablation Site During Catheter Ablation of Accessory Pathways," 1996.
Morrissey, D. M., "Sympathectomy in the treatment of hypertension." Lancet, CCLXIV:403-408 (1953).
Moubarak, Jean B., "Pulmonary Veins-Left Atrial Junction: Anatomic and Histological Study," Pacing & Clin. Electrophys. 23(11 pt. 2):1836-8, 2000.
Nakagawa, H., et al. "Comparison of in vivo tissue temperature profile and lesion geometry for radiofrequeney ablation with a saline-irrigated electrode versus temperature control in a eanine thigh muscle preparation." Circulation, 91 :2264-2273 (1995).
Nakagawa, H., et al. "Inverse relationship between electrode size and lesion size during radiofrequency ablation with active electrode cooling." Circulation, 98:458-465 (1998).
Nakagawa, A., et al. "Selective ablation of porcine and rabbit liver tissue using radiofrequency: Preclinical study." Eur Surg Res, 31: 3 71-379 (1999).
Neutel, J. M. "Hypertension and its management: A problem in need of new treatment strategies." JRAAS, I:S 1 O-S 13 (2000).
Nozawa, T., et al. "Effects of long-term renal sympathetic denervation on heart failure after myocardial infarction in rats." Heart Vessels, 16:51-56 (2002).
O'Connor, B. K., et al. "Radiofrequeney ablation of a posteroseptal accessory pathway via the middle cardiac vein in a six-year-old child." PACE, 20:2504-2507 (1997).
Oliveira et al., "Renal Denervation Normalizes Pressure and Baroreceptor Reflex in High Renin Hypertension in Conscious Rats," Hypertension Suppl. II vol. 19 No. 2, pp. 17-21 (1992).

(56) References Cited

OTHER PUBLICATIONS

Oral, H., et al. "Pulmonary vein isolation for paroxysmal and persistent atrial fibrillation." Circulation, 105:1 077-1081 (2002).
Page, I., et al. "The effect of renal denervation on the level of arterial blood pressure and renal function in essential hypertension." J Clin Invest, XIV:27-30 (1935).
Panescu, D., et al. "Radiofrequency multielectrode catheter ablation in the atrium." Phys Med Biol, 44:899-915 (1999).
Pavin, D., et al. "Permanent left atrial tachyeardia: Radiofrequency catheter ablation through the eoronary sinus." J Cardiovasc Electrophysiol, 12:395-398 (2002).
Peet, M., "Hypertension and its surgical treatment by bilateral supradiaphragmatic splanchnicectomy," Am. J. Surgery, pp. 48-68 (1948).
Petersen, H. H., et al. "Lesion dimensions during temperature controlled radiofrequency catheter ablation of left ventricular porcine myocardium: Impact of ablation site, electrode size, and convective cooling." Circulation, 99:319-325 (1999).
Pohl, M.A. "Renovaseular hypertension and isehemie nephropathy" A chapter in a book edited by Sehrier, R. W. "Atlas 0f diseases of the kidney: Hypertension and the kidney." Blackwell Science (1999).
Prager, Nelson, A., "Long Term Effectiveness of Surgical Treatment of Ectopic Atrial Tachycardia," 1993.
Pugsley, M. K., et al. "The vascular system: An overview of structure and function." J Pharmacol Toxical Methods, 44:333-340 (2000).
Rappaport et al., "Wide-Aperture Microwave Catheter-Based Cardiac Ablation", Proceedings of the First Joint BMES/EMBS Conference, Oct. 13-16, 1999, p. 314.
Reuter, David, M.D., "Future Directions of Electrotherapy for Atrial Fibrillation," 1997.
Robbins, Ivan, M.D., "Pulmonary Vein Stenosis After Catheter Ablation of Atrial Fibrillation," *Circulation*, 98:1769-1775 (1998).
Sanderson, J. E., et al. "Effect of B-blockage on baroreceptor and autonomic function in heart failure." Clin Sei, 69:137-146 (1999).
Schauerte, P., et al. "Catheter ablation of cardiac autonomic nerves for prevention of vagal atrial fibrillation," Circulation, 102:2774-2780 (2000).
Scheinman, Melvin M., "NASPE Survey on Catheter Ablation," 1995.
Scheinman, M. M., et al. "The 1998 NASPE prospective catheter ablation registry." PACE, 23:1020-1028 (2000).
Smithwick et al., "Splanchnicectomy for Essential Hypertension," J. Am. Med. Assn. 152:16, pp. 1501-1504 (1953).
Solis-Herruzo et al., "Effects of Lumbar Sympathetic Block on Kidney Function in Cirrhotic Patients with Hepatorenal Syndrome," J. Hepatol. 5, pp. 167-173 (1987).
Stella, A., et al. "Effects of reversible renal denervation on haemodynamic and excretory functions of the ipsilateral and contralateral kidney in the cat," J Hypertension, 4: 181-188 (1986).
Stellbrink, C., et al. "Transcoronary venous radiofrequency catheter ablation ofventricular tachyeardia." J Cardiovasc Electrophysiol, 8:916-921 (1997).
Swartz, John F., "A Catheter-based Curative Approach to Atrial Fibrillation in Humans," 1994.
Swartz, John F., M.D., "Radiofrequency Endocardial Catheter Ablation of Accessory Atrioventricular Pathway Atrial Insertion Sites," Circulation, 87:487-499 1993.
Takahashi, H., et al. "Retardation of the development of hypertension in DOCA-salt rats by renal denervation." Jpn Circ J, 48:567-574 (1984).
Tanaka et al., "A new radiofrequency thermal balloon catheter for pulmonary vein isolation," Journal of the American College of Cardiology 38(7): 2079-86, Dec. 2001.
Tracy, Cynthia M., "Radiofrequency Catheter Ablation of Ectopic Atrial Tachycardia Using Paced Activation Sequence Mapping," J. of the Amer. College of Cardiol. 21(4):910-7, 1993.

Tungjitkusolmun, S. "Ablation." A chapter in a book edited by Webster, J. G., "Minimally invasive medical technology." Bristol UK: IOP Publishing, 219 (2001).
Uchida, F., et al. "Effect of radio frequency catheter ablation on parasympathetic denervation: A comparison of three different ablation sites," PACE, 21:2517-2521 (1998).
Uflacker, R., "Atlas of vascular anatomy: An angiographic approach." Baltimore: Williams & Wilkins, 424 (1997).
Valente, J. F. "Laparoscopic renal denervation for intractable ADPKD-related pain," Nephrol Dial Transplant, 16:160 (2001).
Van Hare, G. F., et al. "Percutaneous radiofrequency catheter ablation for supraventricular arrhythmias in children." JACC, 17:1613-1620 (1991).
Van Hare, George F., "Radiofrequency Catheter Ablation of Supraventricular Arrhythmias in Patients With Congenital Heart Disease: Results and Technical Considerations," J. of the Amer. College of Cardiol. 22(3):883-90, 1993.
Volkmer, Marius, M.D., "Focal Atrial Tachycardia from Deep Inside the Pulmonary Veins," 1997.
Vujaskovie, Z., et al. "Effects of intraoperative hyperthermia on canine seiatie nerve: Histopathologie and morphometric studies." Int J Hyperthermia, 10,6:845-855 (1994).
Walsh, Edward P., M.D., "Transcatheter Ablation of Ectopic Atrial Tachycardia in Young Patients Using Radiofrequency Current," 1992.
Weinstock, M., et al. "Renal denervation prevents sodium retention and hypertension in salt-sensitive rabbits with genetic baroreflex impairment," Clinical Science, 90:287-293 (1996).
Weir, M. R., et al. "The renin-angiotensin-aldosterone system: A specific target for hypertension management." Am J Hypertens,12:205S-213S (1999).
Yamamoto, T., et al. "Blood velocity profiles in the human renal artery by Doppler ultrasound and their relationship to atherosclerosis." Arterioscl Throm Vas, 16: 172-177 (1996).
Zhang et al., "The development of a RF electrical pole catheter for heart ablation," China Academic Journal Electronic Publishing House 23(5): 279-80, Sep. 1999.
Zipes, Douglas P., M.D., "Catheter Ablation of Arrhythmias," 1994.
Reexam Appl. 95/002,110, Filed: Aug. 29, 2012, Demarais et al.
Reexam Appl. 95/002,209, Filed: Sep. 14, 2012, Levin et al.
Reexam Appl. 95/002,233, Filed: Sep. 13, 2012, Levin et al.
Reexam Appl. 95/002,243, Filed: Sep. 13, 2012, Levin et al.
Reexam Appl. 95/002,253, Filed: Sep. 13, 2012, Demarais et al.
Reexam Appl. 95/002,255, Filed: Sep. 13, 2012, Demarais et al.
Reexam Appl. 95/002,292, Filed: Sep. 14, 2012, Demarais et al.
Reexam Appl. 95/002,327, Filed: Sep. 14, 2012, Demarais et al.
Reexam Appl. 95/002,335, Filed: Sep. 14, 2012, Demarais et al.
Reexam Appl. 95/002,336, Filed: Sep. 14, 2012, Levin et al.
Reexam Appl. 95/002,356, Filed: Sep. 14, 2012, Demarais et al.
Diederich C.J et al. *Transurethral ultrasound array for prostate thermal therapy: initial studies*, IEEE Transactions on Ultrasonics, Ferroelectrics and Frequency Control IEEE USA, vol. 43, No. 6 Nov. 1996 pp. 1011-1022.
Campese, et al., Renal afferent denervation prevents hypertension in rats with chronic renal failure, Hypertension, 25:878-882 (1995).
Dibona, Renal nerves in compensatory renal response to contralateral renal denervation, Renal Physiology, 238 (1):F26-F30 (1980).
Diederich C.J. et al. "Transurethral Ultrasound Array for Prostate Thermal Therapy: Initial Studies", IEEE Transactions on Ultrasonic, Ferroelectronics And Frequency Control IEEEE USA, vol. 43No. 6 Nov. 1996 pp. 1011-1022.
Oliveira, et a., Renal Denervation Normalizes Pressure and Baroreceptor Reflex in High Renin Hypertension in Conscious Rats, Hypertension 19:17-21 (1992).
Smithwick, R.H., Surgery in hypertension, Lancet, 2:65 (1948).
Smithwick, R.H., Surgical treatment of hypertension, Am J Med 4:744-759 (1948).

\* cited by examiner

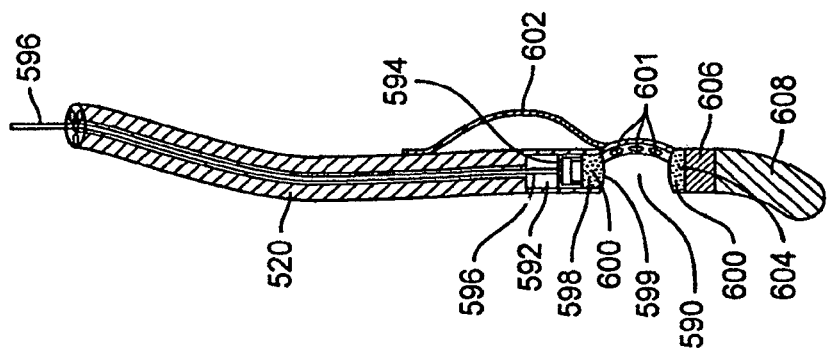
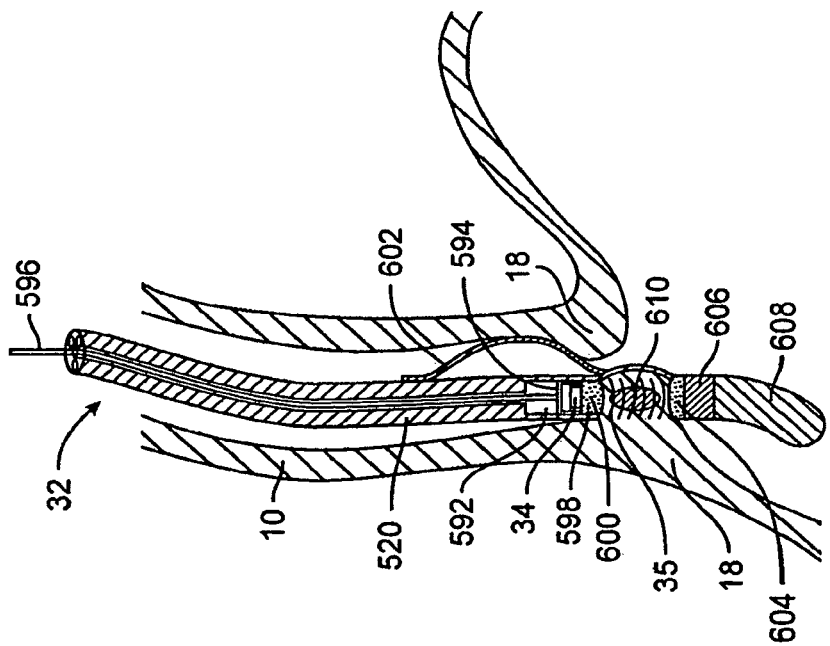

INTRALUMINAL METHOD AND APPARATUS FOR ABLATING NERVE TISSUE

CROSS-REFERENCES TO RELATED APPLICATIONS

The present application is a continuation of U.S. patent application Ser. No. 10/611,838 filed Jun. 30, 2003, which is a non-provisional of U.S. patent application Ser. No. 60/419,317 filed Oct. 16, 2002, which contained the entire content of prior Provisional Application No. 60/393,339 filed on Jul. 1, 2002, with additional material added, the full disclosures of which are incorporated herein by reference.

BACKGROUND OF THE INVENTION

1. Field of the Invention

In a general sense, the invention is directed to systems and methods for treating interior tissue regions of the body. More specifically, the invention is directed to systems and methods for treating dysfunction in body sphincters and adjoining tissue, e.g., in and around the lower esophageal sphincter and cardia of the stomach.

2. Description of the Background Art

The gastrointestinal (GI) tract extends from the mouth to the anus, and includes the esophagus, stomach, small and large intestines, and rectum. Along the way, ring-like muscle fibers called sphincters control the passage of food from one specialized portion of the GI tract to another. The GI tract is lined with a mucosal layer about 1-2 mm thick that absorbs and secretes substances involved in the digestion of food and protects the body's own tissue from self-digestion. The esophagus is a muscular tube that extends from the pharynx through the esophageal hiatus of the diaphragm to the stomach. Peristalsis of the esophagus propels food toward the stomach as well as clears any refluxed contents of the stomach.

The junction of the esophagus with the stomach is controlled by the lower esophageal sphincter (LES), a thickened circular ring of smooth esophageal muscle. The LES straddles the squamocolumnar junction, or z-line--a transition in esophageal tissue structure that can be identified endoscopically. At rest, the LES maintains a high-pressure zone between 10 and 30 mm Hg above intragastric pressures. The LES relaxes before the esophagus contracts, and allows food to pass through to the stomach. After food passes into the stomach, the LES constricts to prevent the contents from regurgitating into the esophagus. The resting tone of the LES is maintained by muscular and nerve mechanisms, as well as different reflex mechanisms, physiologic alterations, and ingested substances. Transient LES relaxations may manifest independently of swallowing. This relaxation is often associated with transient gastroesophageal reflux in normal people. Muscular contractions of the diaphragm around the esophageal hiatus during breathing serve as a diaphragmatic sphincter that offers secondary augmentation of lower esophageal sphincter pressure to prevent reflux.

The stomach stores, dissolves, and partially digests the contents of a meal, then delivers this partially digested food across the pyloric sphincter into the duodenum of the small intestine in amounts optimal for maximal digestion and absorption. Feelings of satiety are influenced by the vagally modulated muscle tone of the stomach and duodenum as well as through the reception and production of biochemicals (e.g., hormones) therein, particularly the gastric antrum.

Finally, after passage of undigested food into the large intestine, it is passed out of the body through the anal sphincter. Fluids unused by the body are passed from the kidneys into the bladder, where a urinary sphincter controls their release.

A variety of diseases and ailments arise from the dysfunction of a sphincter. Dysfunction of the lower esophageal sphincter, typically manifest through transient, relaxations, leads to reflux of stomach acids into the esophagus. One of the primary causes of the sphincter relaxations is believed to be aberrant vagally-mediated nerve impulses to the LES and cardia (upper part of the stomach). This condition, called Gastroesophageal Reflux Disease (GERD), creates discomfort such as heartburn and with time can begin to erode the lining of the esophagus—a condition that can progress to esophagitis and a pre-cancerous condition known as Barrett's Epithelium. Complications of the disease can progress to difficulty and pain in swallowing, stricture, perforation and bleeding, anemia, and weight loss. Dysfunction of the diaphragmatic sphincter, such as that caused by a hiatal hernia, can compound the problem of LES relaxations. It has been estimated that approximately 7% of the adult population suffers from GERD on a daily basis. The incidence of GERD increases markedly after the age of 40, and it is not uncommon for patients experiencing symptoms to wait years before seeking medical treatment.

Treatment of GERD includes drug therapy to reduce or block stomach acid secretions, and/or increase LES pressure and peristaltic motility of the esophagus. Most patients respond to drug therapy, but it is palliative in that it does not cure the underlying cause of sphincter dysfunction, and thus requires lifelong dependence. Invasive abdominal surgical intervention has been shown to be successful in improving sphincter competence. One procedure, called Nissen fundoplication, entails invasive, open abdominal surgery. The surgeon wraps the gastric fundis about the lower esophagus, to, in effect, create a new "valve." Less invasive laparoscopic techniques have also been successful in emulating the Nissen fundoplication. As with other highly invasive procedures, antireflux surgery is associated with the risk of complications such as bleeding and perforation. In addition, a significant proportion of individuals undergoing laparascopic fundoplication report difficulty swallowing (dysphagia), inability to vomit or belch, and abdominal distention.

In response to the surgical risks and drug dependency of patients with GERD, new trans-oral endoscopic technologies are being evaluated to improve or cure the disease. One approach is the endoscopic creation and suturing of folds, or plications, in the esophageal or gastric tissue in proximity to the LES, as described by Swain, et al, [Abstract], Gastrointestinal Endoscopy, 1994; 40:AB35. Another approach, as described in U.S. Pat. No. 6,238,335, is the delivery of biopolymer bulking agents into the muscle wall of the esophagus. U.S. Pat. No. 6,112,123 describes RF energy delivery to the esophageal wall via a conductive medium. Also, as described in U.S. Pat. No. 6,056,744, RF energy has been delivered to the esophageal wall via discrete penetrating needles. The result is shrinkage of the tissue and interruption of vagal afferent pathways some believe to play a role in the transient relaxations of the LES.

The above endoscopic techniques all require the penetration of the esophageal wall with a needle-like device, which entails the additional risks of perforation or bleeding at the puncture sites. Special care and training by the physician is required to avoid patient injury. Use of the plication technique requires many operational steps and over time sutures have been reported to come loose and/or the tissue folds have diminished or disappeared. Control of the amount and location of bulking agent delivery remains an art form, and in some cases the agent has migrated from its original location. RF delivery with needles requires careful monitoring of impedance and temperature in the tissue to prevent coagulation around the needle and associated rapid increases in temperature. Lesion size is also limited by the needle size. Limitations of the design require additional steps of rotating the device to achieve additional lesions. Physicians have to be careful not to move the device during each of the multiple one-minute energy deliveries to ensure the needles do not tear the tissue.

Dysfunction of the anal sphincter leads to fecal incontinence, the loss of voluntary control of the sphincter to retain stool in the rectum. Fecal incontinence is frequently a result of childbearing injuries or prior anorectal surgery. In most patients, fecal incontinence is initially treated with conservative measures, such as biofeedback training, alteration of the stool consistency, and the use of colonic enemas or suppositories. Biofeedback is successful in approximately two-thirds of patients who retain some degree of rectal sensation and functioning of the external anal sphincter. However, multiple sessions are often necessary, and patients need to be highly motivated. Electronic home biofeedback systems are available and may be helpful as adjuvant therapy. Several surgical approaches to fecal incontinence have been tried, with varying success, when conservative management has failed. These treatments include sphincter repair, gracilis or gluteus muscle transposition to reconstruct an artificial sphincter, and sacral nerve root stimulation. The approach that is used depends on the cause of the incontinence and the expertise of the surgeon. Surgical interventions suffer from the same disadvantages discussed above with respect to GERD. An RF needle ablation device, similar in design to that described above for treatment of GERD, has been described in WO/01/80723. Potential device complications and use limitations are similar to those described for GERD.

Dysfunction of the urinary sphincter leads to urinary incontinence, the loss of voluntary control of the sphincter to retain urine in the bladder. In women this is usually manifest as stress urinary incontinence, where urine is leaked during coughing, sneezing, laughing, or exercising. It occurs when muscles and tissues in the pelvic floor are stretched and weakened during normal life events such as childbirth, chronic straining, obesity, and menopause. In men, urinary incontinence is usually a result of pressure of an enlarged prostate against the bladder.

U.S. Pat. No. 6,073,052 describes a method of sphincter treatment using a microwave antennae and specific time and temperature ranges, and U.S. Pat. No. 6,321,121 a method of GERD treatment using a non-specific energy source, with limited enabling specifications. The use of ultrasound energy for circumferential heating of the pulmonary vein to create electrical conduction block has been described in U.S. Pat. Nos. 6,012,457 and 6,024,740. The use of ultrasound for tumor treatments has been described in U.S. Pat. No. 5,620,479.

In view of the foregoing, and notwithstanding the various efforts exemplified in the prior art, there remains a need for a more simple, rapid, minimally invasive approach to treating sphincters that minimizes risk to the patient.

SUMMARY OF THE INVENTION

The present invention seeks to heat sphincter tissues using ultrasound energy. The preferred method is to use ultrasound energy to heat tissue and thus create necrotic regions (lesions) in the tissue. The lesions tighten the tissue by shrinking it (through dessication, protein denaturation, and disruption of collagen bonds), and/or bulking it (with new collagen formation). The lesions also prevent or delay opening of the sphincter by reducing the compliance of the tissue in either or both the radial and longitudinal directions as the sphincter is forced to expand and shorten when the internal pressure increases. The lesions also interrupt nerve pathways responsible for sphincter relaxations. In general, during the heating process, the invention employs means to minimize heat damage to the mucosal layer of the sphincter. However, in the case of Barrett's Esophagus, selective heating of the intestinal metaplasia on the luminal surface of the esophagus is preferred. Ultrasound may also be used (continuously or in pulsed mode) to create shock waves that cause mechanical disruption through cavitation that create the desired tissue effects. While this invention relates broadly to many tissue sphincters in the body, the focus of the disclosure will be on the treatment of a dysfunctional lower esophageal sphincter (LES) responsible for GERD.

The key advantage of an ultrasound ablation system over others is that a uniform annulus of tissue can be heated simultaneously. Alternatively, the transducers can be designed so that only user-defined precise regions of the circumference are heated. Ultrasound also penetrates tissue deeper than RF or simple thermal conduction, and therefore can be delivered with a more uniform temperature profile. Thus lesions can be created at deeper locations than could be safely achieved with RF needles puncturing the tissue. Similarly, the deeper heating and uniform temperature profile also allow for an improved ability to create a cooling gradient at the surface. Relatively low power can be delivered over relatively long durations to maximize tissue penetration but minimize surface heating. If only surface heating is desired, as in the case of Barrett's Esophagus, the acoustic energy can be focused at or just before the tissue surface. Another means to selectively heat the tissue surface is to place a material against the tissue, between the tissue and the transducer, that selectively absorbs acoustic energy and preferentially heats at the tissue interface. A device using ultrasound for ablation may also be configured to allow diagnostic imaging of the tissue to determine the proper location for therapy and to monitor the lesion formation process.

In a first specific aspect of the present invention, methods for remodeling luminal tissue comprise positioning a vibrational transducer at a target site in a body lumen of a patient. The vibrational transducer is energized to produce acoustic energy under conditions selected to induce tissue remodeling in at least a portion of the tissue circumferentially surrounding the body lumen. In particular, the tissue remodeling may be directed at or near the luminal surface, but will more usually be directed at a location at a depth beneath the luminal surface, typically from 1 mm to 10 mm, more usually from 2 mm to 6 mm. In the case of Barrett's Esophagus, the first 1 to 3 mm of tissue depth is to be remodeled. In the most preferred cases, the tissue remodeling will be performed in a generally uniform matter on a ring or region of tissue circumferentially surrounding the body lumen, as described in more detail below.

The acoustic energy will typically be ultrasonic energy produced by electrically exciting an ultrasonic transducer which may optionally be coupled to an ultrasonic horn, resonant structure, or other additional mechanical structure which can focus or enhance the vibrational acoustic energy. In an exemplary case, the transducer is a phased array transducer capable of selectively focusing and/or scanning energy circumferentially around the body lumen.

The acoustic energy is produced under conditions which may have one or more of a variety of biological effects. In many instances, the acoustic energy will be produced under conditions which cause shrinkage of the tissue, optionally by heating the tissue and inducing shrinkage of the collagen. Alternatively or additionally, the acoustic energy may be produced under conditions which induce collagen formation in order to bulk or increase the mass of tissue present. Such collagen formation may in some cases, at least, result from cavitation or other injury-producing application of the vibrational energy. Thus, under some conditions, the vibrational energy will be produced under conditions which cause cavitation within the tissues. Additionally, the acoustic energy may be produced under conditions which interrupt nerve pathways within the tissue, such as the vagal nerves as described in more detail hereinafter.

Preferred ultrasonic transducers may be energized to produce unfocused acoustic energy from the transducer surface in the range from 10 W/cm.sup.2 to 100 W/cm.sup.2, usually from 30 W/cm.sup.2 to 70 W/cm.sup.2. The transducer will usually be energized at a duty cycle in the range from 10% to 100%, more usually from 70% to 100%. Focused ultrasound may have much higher energy densities, but will typically use shorter exposure times and/or duty cycles. In the case of heating the tissue, the transducer will usually be energized under conditions which cause a temperature rise in the tissue to a tissue temperature in the range from 55.degree. C. to 95.degree. C., usually from 60.degree. C. to 80.degree. C. In such instances, it will usually be desirable to cool the luminal surface, which is a mucosal surface in the case of the esophagus which may treated by the present invention, in order to reduce the risk of injury.

Usually, the vibrational transducer will be introduced to the body lumen using a catheter which carries the transducer. In certain specific embodiments, the transducer will be carried within an inflatable balloon on the catheter, and the balloon when inflated will at least partly engage the luminal wall in order to locate the transducer at a pre-determined position relative to the luminal target site. In a particular instance, the transducer is disposed within the inflatable balloon, and the balloon is inflated with an acoustically transmissive material so that the balloon will both center the transducer and enhance transmission of acoustic energy to the tissue. In an alternative embodiment, the transducer may be located between a pair of axially spaced-apart balloons. In such instances, when the balloons are inflated, the transducer is centered within the lumen. Usually, an acoustically transmissive medium is then introduced between the inflated balloons to enhance transmission of the acoustic energy to the tissue. In any of these instances, the methods of the present invention optionally comprise moving the transducer relative to the balloons, typically in an axially direction, in order to focus or scan the acoustic energy at different locations on the luminal tissue surface.

In specific embodiments, the acoustically transmissive medium may be cooled in order to enhance cooling of the luminal tissue surface. Additionally, the methods may further comprise monitoring temperature of the luminal tissue surface and/or at a point beneath the luminal tissue surface.

In other specific examples, methods of the present invention further comprise focusing acoustic energy beneath the luminal tissue surface. Or in the case of Barrett's Esophagus, acoustic energy is focused at or just before the luminal tissue surface. In such instances, focusing may be achieved using a phased array (by selectively energizing particular elements of the array) and the tissue may be treated at various locations and various depths.

The methods as described above are particularly preferred for treating patients suffering from gastroesophageal reflex disease (GERD) where the acoustic energy remodels the tissue surrounding a lower esophageal sphincter (LES). In other instances, the methods of the present invention may be used to treat patients suffering hiatal hernias, where the acoustic energy is directed at tissue surrounding a diaphragmatic sphincter above the LES, to treat the anal sphincter for incontinent patients, to remodel tissues of the bladder neck and surrounding endopelvic fascia for urinary stress incontinence, etc. Further, the methods of the present invention can be used to induce feelings of satiety in obese patients, where acoustic energy is delivered to regions of the stomach and small intestine to interrupt or modify vagal mediation of muscle tone, or to block or modify the reception and production of biochemicals that affect satiety. The acoustic energy may also be used to selectively necrose or shrink tissue in the pylorus to delay gastric emptying and prolong the sensation of fullness. Acoustic energy may also be used to render regions of tissue unable to absorb food.

The methods of the present invention may further comprise introducing a cannula to the target site, expanding a balloon on the cannula at the target site with an acoustically transmissive medium, and selectively directing the vibrational transducer within the balloon to remodel targeted tissue. The balloon can provide a relatively large working space and optionally can seal an opening to the body lumen, such as to the esophagus. Optionally, a viewing scope or other viewing means can be introduced into the balloon on the cannula to allow visualization of the tissue being treated. In such cases, the acoustically transmissive medium should also be transparent. Within the inflated balloon, the transducer on the catheter may be manipulated in a variety of ways, including deflecting, rotating, everting, and the like, in order to direct the vibrational energy precisely where desired. Alternatively or additionally, phased array and other circumferential array transducers may be axially translated to otherwise selectively positioned to achieve a desired therapy. When used at the end of the esophagus or at another opening to a body lumen, the balloon on the cannula may be expanded to cover the entire opening or alternatively may be expanded over a location adjacent to the opening.

In other embodiments, directing the transducer may comprise selectively pivoting at least one transducer from a fixed location on the catheter or otherwise within the balloon, optionally comprising deflecting at least two catheters from spaced-apart locations. In such cases, the two transducers may be used together in order to focus energy at particular location(s) within the target tissue.

In yet another aspect of the present invention, positioning the transducer may comprise capturing luminal tissue between opposed elements on the catheter where the transducer is disposed on at least one of the elements. The energy may then be directed from the transducer into the captured tissue. Capturing may comprise clamping the tissue between moveable elements and/or applying a vacuum to the tissue to draw tissue between the opposed elements.

The present invention still further comprises apparatus for remodeling the lower esophageal sphincter. Such apparatus comprise a catheter or probe adapted to be esophageally introduced to the lower esophageal sphincter and a vibrational transducer on the catheter. The transducer is adapted to deliver acoustic energy to the tissue of the LES in order to lessen gastroesophageal reflux. Apparatus for treating other sphincters may also be provided for certain sphincters such as the anal sphincter. The apparatus may comprise a more rigid probe instead of a highly flexible catheter.

Specific apparatus constructions include providing an inflatable balloon on the catheter, where the balloon is adapted when inflated to position the catheter within the LES so that the transducer can deliver energy to the LES. The transducer is usually positioned coaxially within the balloon, and means may be provided for inflating the balloon with an acoustically transmissive medium.

Alternatively, the transducer may be positioned between a pair of axially-spaced-apart balloons, where the apparatus will typically further comprise means for delivering an acoustically transmissive medium between the balloons. In all instances, the apparatus may further comprise means for cooling the acoustically transmissive medium, and means for axially translating the transducer relative to the catheter. In certain specific examples, the transducer comprises a phased array transducer.

The present invention may further comprise systems including apparatus as set forth above in combination with a cannula having a channel for receiving and deploying the catheter of the apparatus. Usually, the systems will further include a viewing scope or other imaging component which is either part of the cannula or introducable through the cannula.

In preferred embodiments, the cannula further comprises an inflatable balloon formed over a distal end thereof, where the catheter is extendable from the cannula into the balloon when the balloon is inflated. In such embodiments, the vibrational transducer on the catheter is preferably deflectable, rotatable, and/or evertable within the balloon when inflated to allow a high degree of selective positioning of the transducer. Alternatively, the vibrational transducer may comprise a circumferential array which is axially translatable or otherwise positionable on the catheter when the balloon is inflated. Still further optionally, the transducer(s) may comprise pivotally mounted transducers on the catheter to permit separate or focused positioning of the transducers. Still further alternatively, the transducer(s) may be mounted on a pair of spaced-apart elements on the catheter, where the elements are configured to receive target tissue therebetween. Usually, the elements will be movable to clamp tissue therebetween and/or a vacuum source will be provided on the catheter to selectively draw tissue into the space between the spaced-apart elements.

BRIEF DESCRIPTION OF THE DRAWINGS

FIGS. 52a and 52b illustrate the use of an ablation device that sucks tissue in the region of the LES into a chamber where energy delivered into captured tissue.

DETAILED DESCRIPTION OF THE INVENTION

This Specification discloses various catheter-based systems and methods for treating dysfunction of sphincters and adjoining tissue regions in the body. The systems and methods are particularly well suited for treating these dysfunctions in the upper gastrointestinal tract, e.g., in the lower esophageal sphincter (LES) and adjacent cardia of the stomach. For this reason, the systems and methods will be described in this context.

Still, it should be appreciated that the disclosed systems and methods are applicable for use in treating other dysfunctions elsewhere in the body, which are not necessarily sphincter-related. For example, the various aspects of the invention have application in procedures requiring treatment of hemorrhoids, or incontinence, or restoring compliance to or otherwise tightening interior tissue or muscle regions. The systems and methods that embody features of the invention are also adaptable for use with systems and surgical techniques that are not necessarily catheter-based.

In general, this disclosure relates to the ability of the ultrasound to heat the tissue in order to cause it to acutely shrink and tighten. It should also be noted that another physiologic means by which the tissue may move inward after heating is through the stimulation of new collagen growth during the healing phase. Besides swelling the wall, it may also serve to strengthen the wall. Further, by necrosing viable tissue, vagal afferent pathways responsible for transient relaxations of the LES are reduced or eliminated, leading to improved tonic contraction of the LES.

For the purposes of stimulating collagen growth, it may be sufficient to deliver shock waves to the tissue such that the tissue matrix is mechanically disrupted (i.e, via cavitation), but not necessarily heated. This is another means by which ultrasound could be a more beneficial energy modality than others. The ultrasound could be delivered in high-energy MHz pulses or through lower energy kHz or "lithotriptic" levels.

Figure 1:
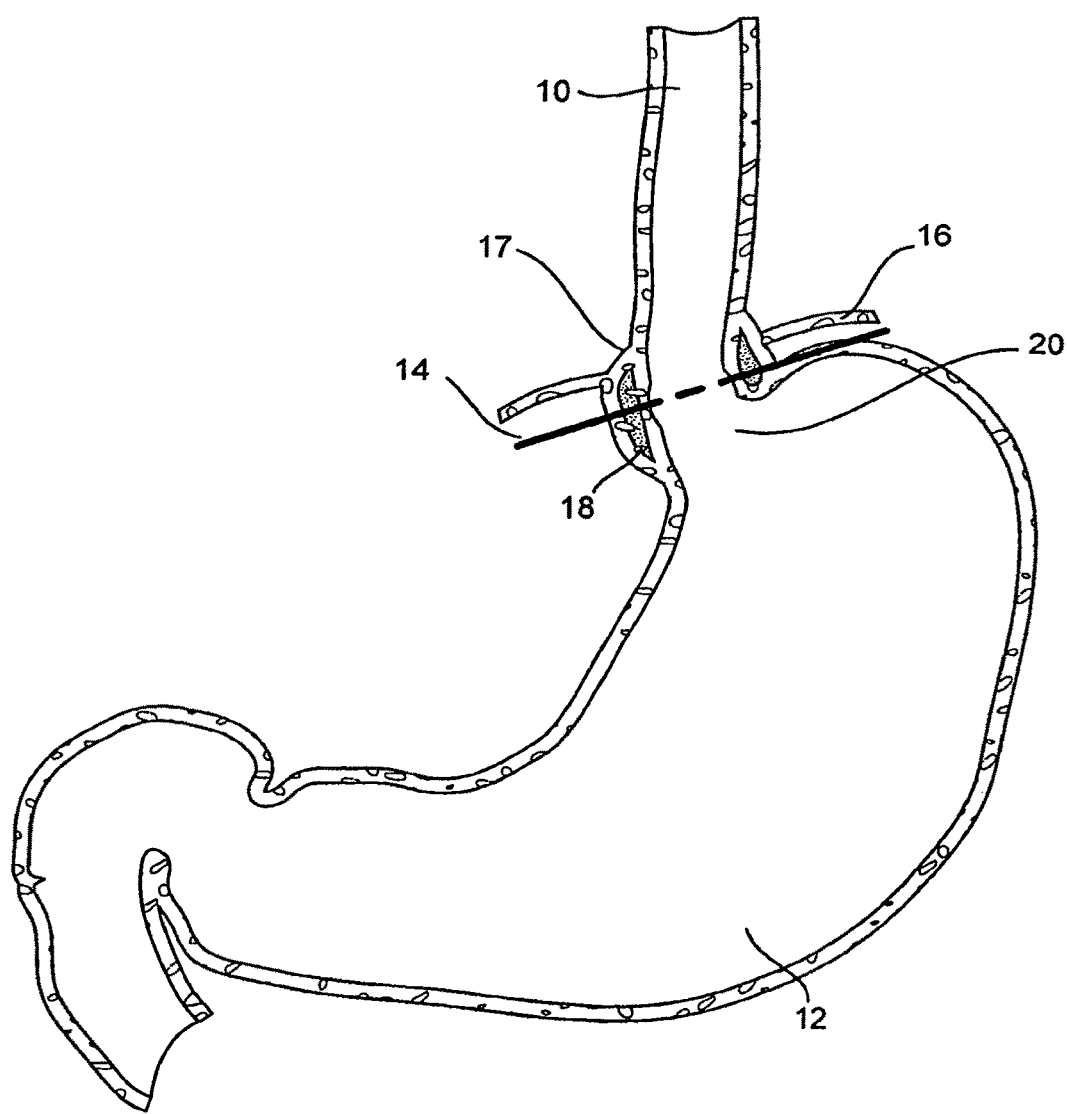
FIG. 1 is an illustration of the tissue structures comprising the esophagus and stomach.

As FIG. 1 shows, the esophagus 10 is an approximately 25 cm long muscular tube that transports food from the mouth to the stomach 12 using peristaltic contractions. Mucous is secreted from the walls of the esophagus to lubricate the inner surface and allow food to pass more easily.

The junction of the esophagus 10 with the stomach 12 is controlled by the lower esophageal sphincter (LES) 18, a thickened circular ring of smooth esophageal muscle. The LES straddles the squamocolumnar junction, or z-line 14—a transition in esophageal tissue structure that can be identified endoscopically. An upper region of the stomach 12 that surrounds the LES 18 is referred to as the cardia 20. After food passes into the stomach 12, the LES 18 constricts to prevent the contents from regurgitating into the esophagus 10. Muscular contractions of the diaphragm 16 around the esophageal hiatus 17 during breathing serve as a diaphragmatic sphincter that offers secondary augmentation of lower esophageal sphincter pressure to prevent reflux.

The LES 18 relaxes before the esophagus 10 contracts, and allows food to pass through to the stomach 12. After food passes into the stomach 12, the LES 18 constricts to prevent the contents from regurgitating into the esophagus 10. The resting tone of the LES 18 is maintained by muscular and nerve mechanisms, as well as different reflex mechanisms, physiologic alterations, and ingested substances. Transient LES relaxations may manifest independently of swallowing. This relaxation is often associated with transient gastroesophageal reflux in normal people.

Dysfunction of the LES 18, typically manifest through transient relaxations, leads to reflux of stomach acids into the esophagus 10. One of the primary causes of the sphincter relaxations is believed to be aberrant vagally-mediated nerve impulses to the LES 18 and cardia 20. This condition, called Gastroesophageal Reflux Disease (GERD), creates discomfort such as heartburn and other debilitating symptoms. Dysfunction of the diaphragmatic sphincter (at the esophageal hiatus 17), such as that caused by a hiatal hernia, can compound the problem of LES relaxations.

It should be noted that the views of the esophagus and stomach shown in FIG. 1 and elsewhere in the drawings are not intended to be strictly accurate in an anatomic sense. The drawings show the esophagus and stomach in somewhat diagrammatic form to demonstrate the features of the invention.

Figure 2:
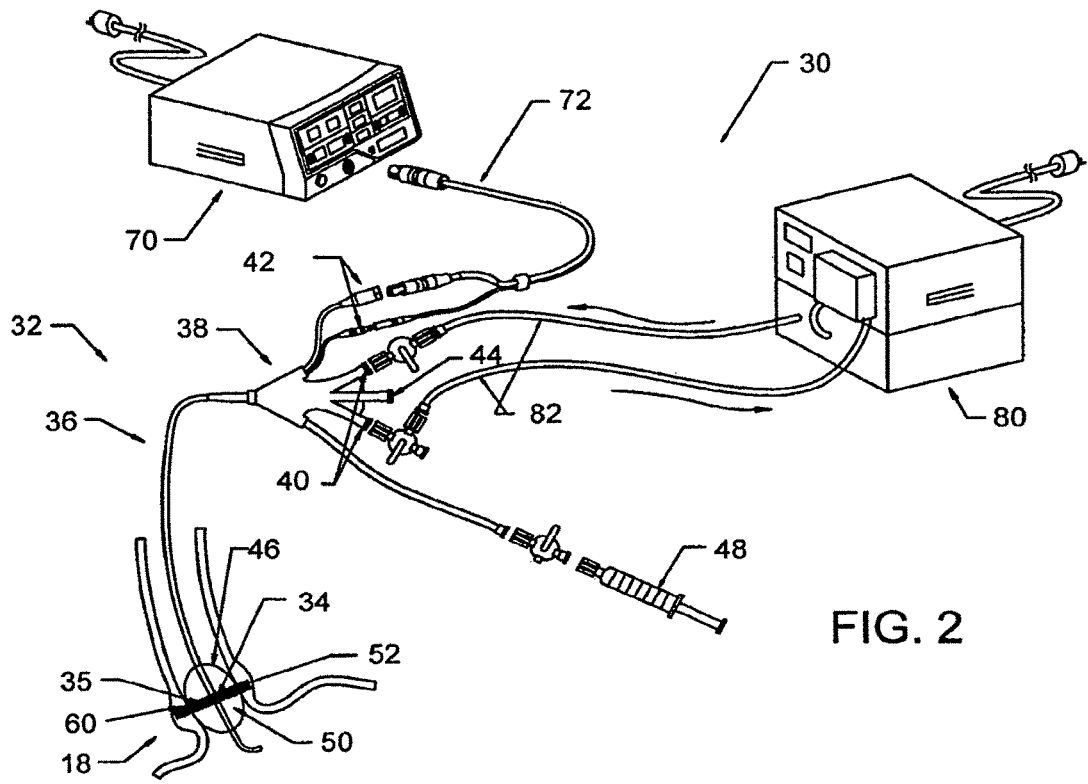
FIG. 2 is an Ultrasound Ablation System for GERD Treatment.

As shown in FIG. 2, the present invention relates to an ablation system 30 consisting of an ablation device 32 with an acoustic energy delivery element (ultrasound transducer) 34 mounted on the distal end of the catheter. The device is delivered transorally to the region of the LES 18. The system 30 consists of the following key components:

1. A catheter shaft 36 with proximal hub 38 containing fluid ports 40, electrical connectors 42, and optional central guidewire lumen port 44.
2. An ultrasound transducer 34 that produces acoustic energy 35 at the distal end of the catheter shaft 36
3. An expandable balloon 46 operated with a syringe 48 used to create a fluid chamber 50 that couples the acoustic energy 35 to the tissue 60
4. Temperature sensor(s) 52 in the zone of energy delivery
5. An energy generator 70 and connector cable(s) 72 for driving the transducer and displaying temperature values
6. A fluid pump 80 delivering cooling fluid 82.

Figure 3:
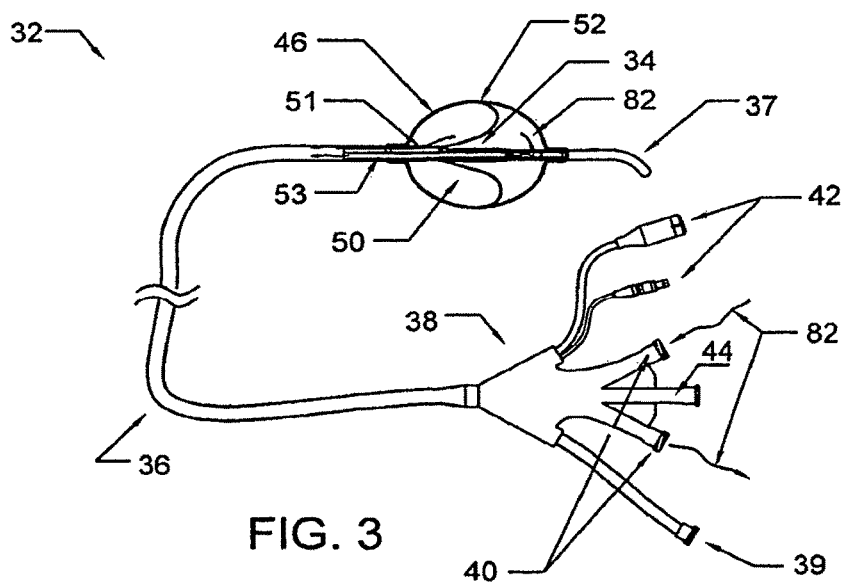
FIG. 3 is an Ultrasound Ablation Catheter.

As shown in FIG. 3, the preferred embodiment of the ablation device consists of an ultrasound transducer 34 mounted within the balloon 46 near the distal end of an elongated catheter shaft 36. A proximal hub, or handle, 38 allows connections to the generator 70, fluid pump 80, and balloon inflation syringe 48. In other embodiments (not shown) the hub/handle 38 may provide a port for a guidewire and an actuator for deflection or spline deployment. The distal tip 39 is made of a soft, optionally preshaped, material such as low durometer silicone or urethane to prevent tissue trauma. The ultrasound transducer 34 is preferably made of a cylindrical ceramic PZT material, but could be made of other materials and geometric arrangements as are discussed in more detail below. Depending on performance needs, the balloon 46 may consist of a compliant material such as silicone or urethane, or a more non-compliant material such as nylon or PET, or any other material having a compliance range between the two. Temperature sensors 52 are aligned with the beam of acoustic energy 35 where it contacts the tissue. Various configurations of temperature monitoring are discussed in more detail below. The catheter is connected to an energy generator 70 that drives the transducer at a specified frequency. The optimal frequency is dependent on the transducer 34 used and is typically in the range of 7-10 MHz, but could be 1-40 MHz. The frequency may be manually entered by the user or automatically set by the generator 70 when the catheter is connected, based on detection algorithms in the generator. The front panel of the generator 70 displays power levels, delivery duration, and temperatures from the catheter. A means of detecting and displaying balloon inflation volume and/or pressure, and cooling flow rate/pressure may also be incorporated into the generator. Prior to ablation, the balloon 46 is inflated with a fluid such as saline or water, or an acoustic coupling gel, until it contacts the esophagus over a length exceeding the transducer length. Cooling fluid 82 is used to minimize heat buildup in the transducer and keep the mucosal surface temperatures in a safe range. In the preferred embodiment shown, cooling fluid 82 is circulated in through the balloon inflation lumen 51 and out through the central lumen 53 using a fluid pump 80. As described later, the circulation fluid may be routed through lumens different than the balloon lumen, requiring a separate balloon inflation port 39. Also, it may be advantageous to irrigate the outer proximal and/or distal end of the balloon to cool it and to ensure the expulsion or air on the outer edges of the balloon that could interfere with the coupling of the ultrasound into the tissue. The path of this irrigating fluid could be from a lumen in the catheter and out through ports proximal and/or distal to the balloon, or from the inner lumen of a sheath placed over the outside of or alongside the catheter shaft.

In other embodiments (not shown) of the catheter, the central lumen 53 could allow passage of a guidewire (i.e., 0.035") from a proximal port 44 out the distal tip 39 for atraumatic placement into the body. Alternatively, a monorail guidewire configuration could be used, where the catheter 30 rides on the wire just on the tip section 39 distal to the transducer 34. A central lumen with open tip configuration would also allow passage of an endoscope for visualization during the procedure. The catheter could also be fitted with a pull wire connected to a proximal handle to allow deflection to aid in placement through the mouth and down the esophagus. This could also allow deflection of an endoscope in the central lumen. The balloon may also be designed with a textured surface (i.e., adhesive bulbs or ribs) to prevent movement in the inflated state. Finally, the catheter shaft or balloon or both could be fitted with electrodes that allow pacing and electrical signal recording within the esophagus.

The above ablation device 32 is configured as an elongated catheter. Of course, depending on the sphincter being treated, the ablation device may be configured as a probe, or a surgically delivered instrument.

In use (see FIGS. 4a, 4b, 5 and 6), the patient lies awake but sedated in a reclined or semi-reclined position. If used, the physician inserts an esophageal introducer 92 through the throat and partially into the esophagus 10. The introducer 92 is pre-curved to follow the path from the mouth, through the pharynx, and into the esophagus 10. The introducer 92 also includes a mouthpiece 94, on which the patient bites to hold the introducer 92 in position. The introducer 92 provides an open, unobstructed path into the esophagus 10 and prevents spontaneous gag reflexes during the procedure.

The physician need not use the introducer 92. In this instance, a simple mouthpiece 94, upon which the patient bites, is used.

Figure 4A:
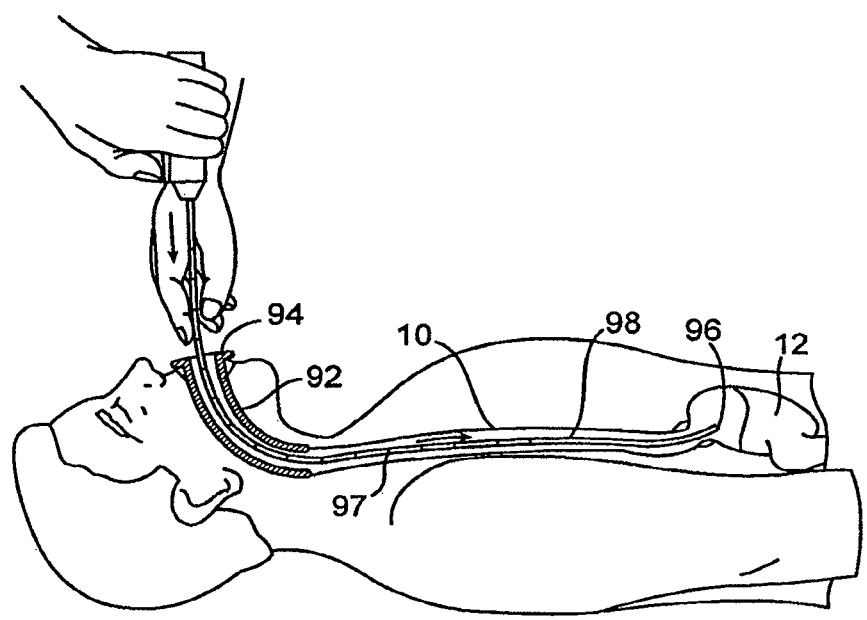
FIG. 4*a* illustrates the diagnostic endoscopic procedure used to identify the target treatment area.

The physician preferably first conducts a diagnostic phase of the procedure, to localize the site to be treated. As FIG. 4a shows, a visualization device can be used for this purpose. The visualization device can comprise an endoscope 96, or other suitable visualizing mechanism, carried at the end of a flexible catheter tube 98. The catheter tube 98 for the endoscope 96 includes measured markings 97 along its length. The markings 97 indicate the distance between a given location along the catheter tube 98 and the endoscope 96.

The physician passes the catheter tube 98 through the patient's mouth and pharynx, and into the esophagus 10, while visualizing through the endoscope 96. Relating the alignment of the markings 97 to the mouthpiece 94, the physician can gauge, in either relative or absolute terms, the distance between the patient's mouth and the endoscope 96 in the esophagus 10. When the physician visualizes the desired treatment site (lower esophageal sphincter 18 or cardia 20) with the endoscope 96, the physician records the markings 97 that align with the mouthpiece 94.

Figure 4B:
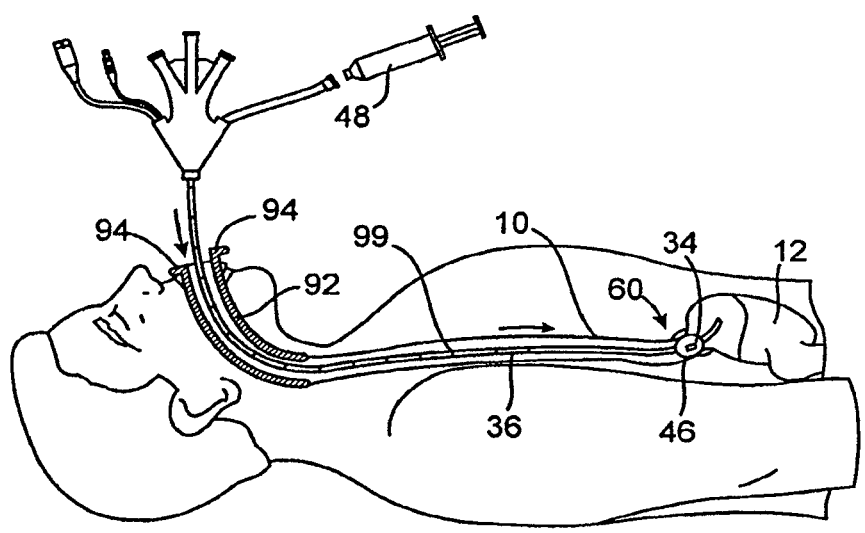
FIG. 4*b* illustrates the delivery of the tissue treatment apparatus.

The physician next begins the treatment phase of the procedure. As shown in FIG. 4b, the physician passes the catheter shaft 36 carrying the ultrasound transducer 34 through the introducer 92. For the passage, the expandable balloon 46 is in its collapsed condition. The physician can keep the endoscope 96 deployed for viewing the expansion and fit of the balloon 46 with the tissue 60, either separately deployed in a side-by-side relationship with the catheter shaft 36, or (as will be described later) by deployment through a lumen in the catheter shaft 36 or advancement of the catheter 32 through a lumen in the endoscope 96 itself and expansion of the balloon distal to the endoscope 96. If there is not enough space for side-by-side deployment of the endoscope 96, the physician deploys the endoscope 96 before and after expansion of the balloon 46.

As illustrated in FIG. 4b, the catheter shaft 36 includes measured markings 99 along its length. The measured markings 99 indicate the distance between a given location along the catheter shaft 36 and the ultrasound transducer 34. The markings 99 on the catheter shaft 36 correspond in spacing and scale with the measured markings 97 along the endoscope catheter tube 98. The physician can thereby relate the markings 99 on the catheter shaft 36 to gauge, in either relative or absolute terms, the location of the ultrasound transducer 34 inside the esophagus 10. When the markings 99 indicate that the ultrasound transducer 34 is at the desired location (earlier visualized by the endoscope 96), the physician stops passage of the ultrasound transducer 34. The ultrasound transducer 34 is now located at the site targeted for treatment.

Figure 5:
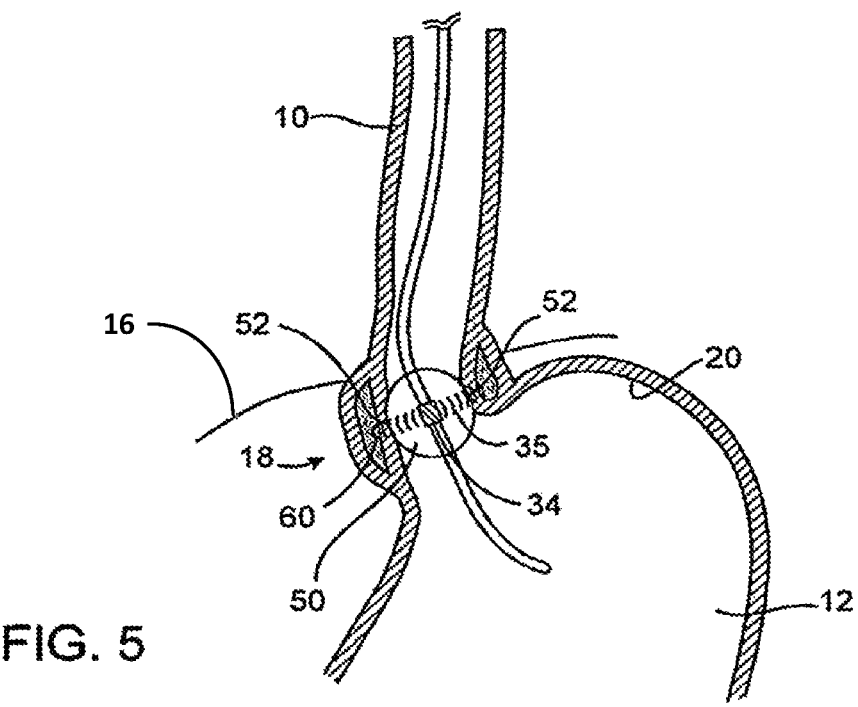
FIG. 5 illustrates the positioning of the ultrasound transducer and balloon at the region of the lower esophageal sphincter.
Figure 6:
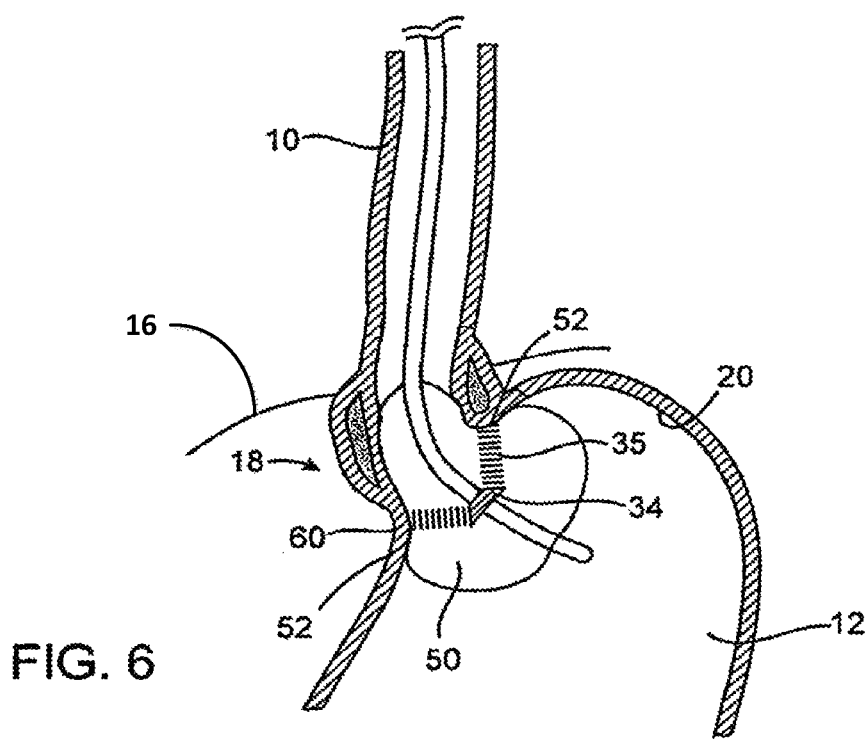
FIG. 6 illustrates the positioning of the "rear-directed" ultrasound transducer and balloon distal to the lower esophageal sphincter for delivering energy to the inferior aspect of the lower esophageal sphincter and the cardia.

In FIG. 5, the targeted site is shown to be the lower esophageal sphincter 18. In FIG. 6, the targeted site is shown to be the cardia 20 of the stomach 12.

Once located at the targeted site, the physician operates the syringe 48 to convey fluid or coupling gel into the expandable balloon 46. The balloon 46 expands to make intimate contact with the mucosal surface, either with the sphincter (see FIG. 5) or the cardia 20 (FIG. 6) over a length longer than where the acoustic energy 35 impacts the tissue. The balloon is expanded to temporarily dilate the lower esophageal sphincter 18 or cardia 20, to remove some or all the folds normally present in the mucosal surface, and to create a chamber 50 of fluid or gel through which the acoustic energy 35 couples to the tissue 60. The expanded balloon 46 also places the temperature sensors 52 in intimate contact with the mucosal surface.

The physician commands the energy generator 70 to apply electrical energy to the ultrasound transducer 34. The function of the ultrasound transducer 34 is to then convert the electrical energy to acoustic energy 35.

The energy heats the smooth muscle tissue below the mucosal lining. The generator 70 displays temperatures sensed by the temperature sensors 80 to monitor the application of energy. The physician may choose to reduce the energy output of the generator 70 if the temperatures exceed predetermined thresholds. The generator 70 may also automatically shutoff the power if temperature sensors 80 or other sensors in the catheter exceed safety limits.

Prior to energy delivery, it will most likely be necessary for the physician to make use of a fluid pump 80 to deliver cooling fluid 82 to keep the mucosal temperature below a safe threshold. This is discussed in more detail later. The pump 80 may be integrated into the generator unit 70 or operated as a separate unit.

Preferably, for a region of the lower esophageal sphincter 18 or cardia 20, energy is applied to achieve tissue temperatures in the smooth muscle tissue in the range of 55.degree. C. to 95.degree. C. In this way, lesions can typically be created at depths ranging from one 1 mm below the mucosal surface to as far as the outside wall of the esophagus 10. Typical acoustic energy densities range 10 to 100 W/cm.sup.2 as measured at the transducer surface. For focusing elements, the acoustic energy densities at the focal point are much higher.

It is desirable that the lesions possess sufficient volume to evoke tissue-healing processes accompanied by intervention of fibroblasts, myofibroblasts, macrophages, and other cells. The healing processes results in a contraction of tissue about the lesion, to decrease its volume or otherwise alter its biomechanical properties. Replacement of collagen by new collagen growth may also serve to bulk the wall of the sphincter. The healing processes naturally tighten the smooth muscle tissue in the sphincter 18 or cardia 20. Ultrasound energy typically penetrates deeper than is possibly by RF heating or thermal conduction alone.

Figure 7:
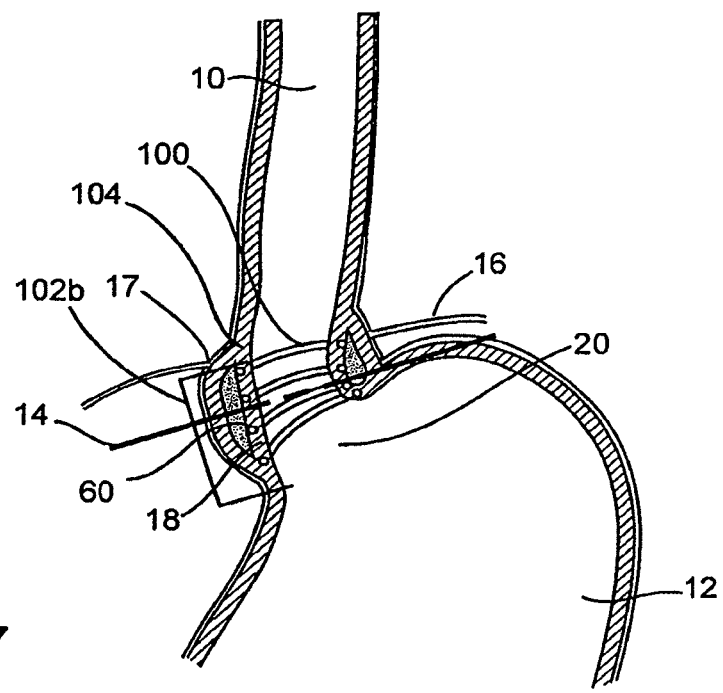
FIG. 7 is a preferred pattern of completely circumferential lesions.

With a full circumferential output of acoustic energy 35 from ultrasound transducer 34, it is possible to create a completely circumferential lesion 100 in the tissue 60 of the LES 18. To create greater lesion density in a given targeted tissue area, it is also desirable to create a pattern of multiple circumferential lesions 102a spaced axially along the length of the targeted treatment site in the LES 18 or cardia 20 (above and below the z-line 14, as shown in FIG. 7. Preferably, a pattern of 4 circumferential lesions 102a is desired spaced 1 cm apart, with 2 above the z-line 14, and 2 below; however, the safe and effective range may be just one or higher, depending on how the lesions form and heal. As shown in FIG. 6, the use of a "rear directed" ultrasound beam also allows treatment of the inferior aspect of the LES 18 and the cardia 20.

Figure 8:
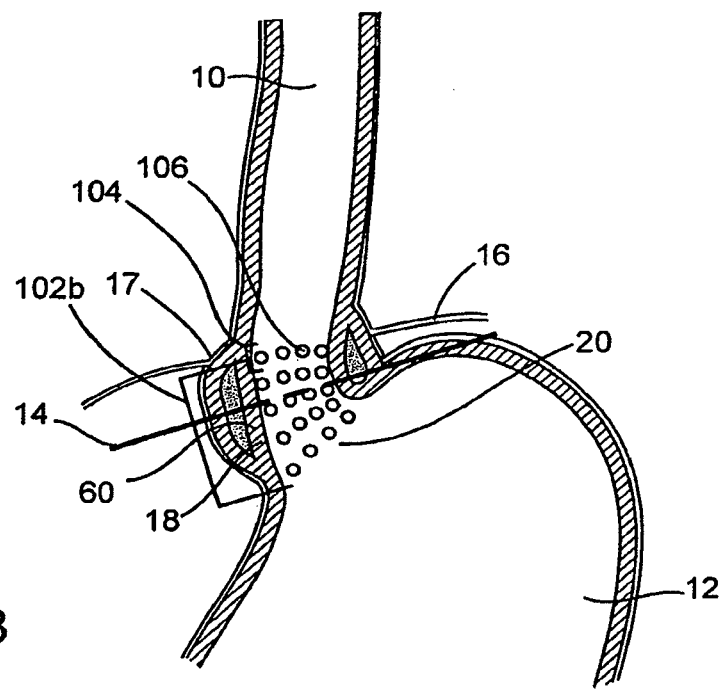
FIG. 8 is a preferred pattern of groups of discrete lesions formed in circumferential groups.

To limit the amount of tissue ablated, and still achieve the desired effect, it may be beneficial to spare and leave viable some circumferential sections of the esophageal wall. To this end, the ultrasound transducer 34 can be configured (embodiments of which are discussed in detail below) to emit ultrasound in discrete locations around the circumference. Various lesion patterns 102b can be achieved. A preferred pattern (shown in FIG. 8 for the esophagus 10) comprises several rings 104 of lesions 106 about 5 mm apart, each ring 104 comprising preferably 8 (potential range 1-16) lesions 106. For example, a preferred pattern 102b comprises six rings 104, 3 above and 3 below the z-line 14, each with eight lesions 106.

The physician can create a given ring pattern (either fully circumferential lesions or discrete lesions spaced around the circumference) 100 by expanding the balloon 46 with fluid or gel, pumping fluid 82 to cool the mucosal tissue interface as necessary, and delivering electrical energy from the generator 70 to produce acoustic energy 35 to the tissue 90. The lesions in a given ring (100 or 104) can be formed simultaneously with the same application of energy, or one-by-one, or in a desired combination. Additional rings of lesions can be created by advancing the ultrasound transducer 34 axially, gauging the ring separation by the markings 99 on the catheter shaft 36. Other, more random or eccentric patterns of lesions can be formed to achieve the desired density of lesions within a given targeted site.

The catheter 32 can also be configured such that once the balloon 46 is expanded in place, the distal shaft 36 upon which the transducer 34 is mounted can be advanced axially within the balloon 46 that creates the fluid chamber 35, without changing the position of the balloon 46. Preferably, the temperature sensor(s) 52 move with the transducer 34 to maintain their position relative to the energy beam 35.

The distal catheter shaft 36 can also be configured with multiple ultrasound transducers 34 and temperature sensors 52 along the distal axis in the fluid chamber 35 to allow multiple rings to be formed simultaneously or in any desired combination. They can also simply be formed one-by-one without having to adjust the axial position of the catheter 32.

To achieve certain heating effects, it may be necessary to utilize variations of the transducer, balloon, cooling system, and temperature monitoring. For instance, in order to prevent ablation of the mucosal lining of the esophagus 10, it may be necessary to either (or both) focus the ultrasound under the surface, or sufficiently cool the surface during energy delivery. To treat Barrett's Esophagus, the ultrasound may be focused at or just before the tissue surface. The balloon material, or an additional material adjacent to the balloon between the tissue and the transducer may be made of sufficient dimensions and acoustic properties to selectively absorb energy at the tissue interface. Materials having good acoustic absorption properties include silicone and polyurethane rubbers, and oil suspensions. Increasing the frequency of the transducer will also aid in confining acoustic absorption at the surface. Temperature monitoring provides feedback as to the how well the tissue is being heated and cooled.

The following sections describe various embodiments of the ultrasound transducer 34 design, the mounting of the ultrasound transducer 34, cooling configurations, and means of temperature monitoring.

Figure 9:
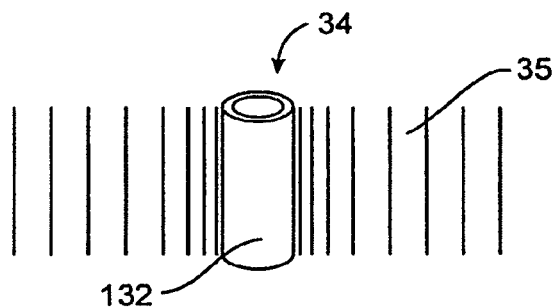
FIG. 9 is a cylindrical PZT material.

Ultrasound Transducer Design Configurations: In one preferred embodiment, shown in FIG. 9, the transducer 34 is a cylinder of PZT (i.e., PZT-4, PZT-8) material 130. The material is plated on the inside and outside with a conductive metal, and poled to "flip", or align, the dipoles in the PZT material 130 in a radial direction. This plating 120 allows for even distribution of an applied potential across the dipoles. It may also be necessary to apply a "seed" layer (i.e., sputtered gold) to the PZT 130 prior to plating to improve plating adhesion. The dipoles (and therefore the wall of the material) stretch and contract as the applied voltage is alternated. At or near the resonant frequency, acoustic waves (energy) 35 emanate in the radial direction from the entire circumference of the transducer. The length of the transducer can be selected to ablate wide or narrow regions of tissue. The cylinder is 5 mm long in best mode, but could be 2-20 mm long. Inner diameter is a function of the shaft size on which the transducer is mounted, typically ranging from 1 to 4 mm. The wall thickness is a function of the desired frequency. An 8 MHz transducer would require about a 0.011" thick wall.

Figure 10:
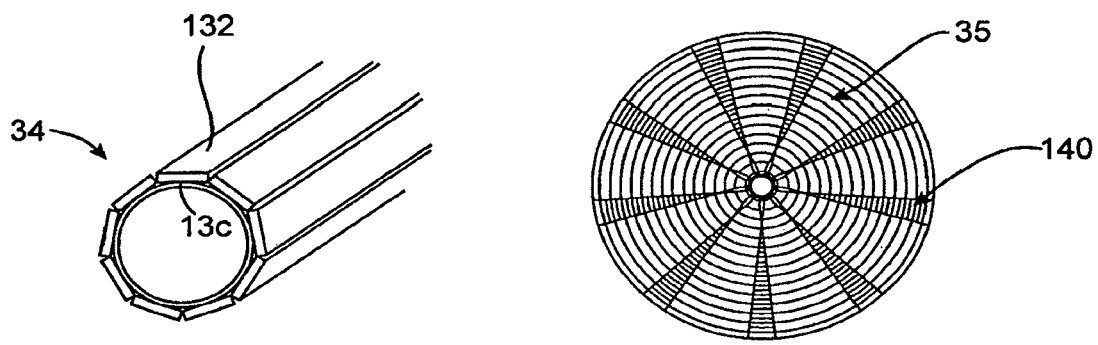
FIG. 10 is an annular array of flat panel transducers and the acoustic output from the array.

In another embodiment of the transducer 34 design, illustrated in FIG. 10, multiple strips 132 of PZT 130 or MEMS (Micro Electro Mechanical Systems—Sensant, Inc., San Leandro, Calif.) material are positioned around the circumference of the shaft to allow the user to ablate selected sectors. The strips 132 generally have a rectangular cross section, but could have other shapes. Multiple rows of strips could also be spaced axially along the longitudinal axis of the device. By ablating specific regions, the user may avoid collateral damage in sensitive areas, or ensure that some spots of viable tissue remain around the circumference after energy delivery. The strips 132 may be all connected in parallel for simultaneous operation from one source, individually wired for independent operation, or a combination such that some strips are activated together from one wire connection, while the others are activated from another common connection. In the latter case, for example, where 8 strips are arranged around the circumference, every other strip (every 90.degree.) could be activated at once, with the remaining strips (90.degree. C. apart, but 45.degree. C. from the previous strips) are activated at a different time. Another potential benefit of this multi-strip configuration is that simultaneous or phased operation of the strips 132 could allow for regions of constructive interference (focal regions 140) to enhance heating in certain regions around the circumference, deeper in the tissue. Phasing algorithms could be employed to enhance or "steer" the focal regions 140. Each strip 132 could also be formed as a curved x-section or be used in combination with a focusing lens to deliver multiple focal heating points 140 around the circumference.

The use of multiple strips 132 described above also allows the possibility to use the strips for imaging. The same strips could be used for imaging and ablation, or special strips mixed in with the ablation strips could be used for imaging. The special imaging strips may also be operated at a different frequency than the ablation strips. Since special imaging strips use lower power than ablation strips, they could be coated with special matching layers on the inside and outside as necessary, or be fitted with lensing material. The use of MEMs strips allows for designs where higher resolution "cells" on the strips could be made for more precise imaging. The MEMs design also allows for a mixture of ablation and imaging cells on one strip. Phasing algorithms could be employed to enhance the imaging.

Figure 11:
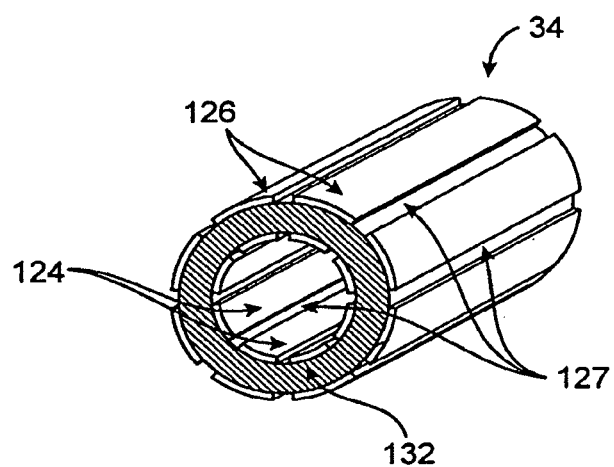
FIG. 11 is isolated active sectors of a transducer formed by isolating the plated regions.

In another embodiment of the transducer 34 design, shown in FIG. 11, a single cylindrical transducer 34 as previously described is subdivided into separate active longitudinal segments 134 arrayed around the circumference through the creation of discrete regions of inner plating 124 and outer plating 126. To accomplish this, longitudinal segments of the cylindrical PZT material 130 could be masked to isolate regions 127 from one another during the plating process (and any seed treatment, as applicable). Masking may be accomplished by applying wax, or by pressing a plastic material against the PZT 130 surface to prevent plating adhesion. Alternatively, the entire inner and outer surface could be plated followed by selective removal of the plating (by machining, grinding, sanding, etc.). The result is similar to that shown in FIG. 10, with the primary difference being that the transducer is not composed of multiple strips of PZT 130, but of one continuous unit of PZT 130 that has different active zones electrically isolated from one another. Ablating through all at once may provide regions of constructive interference (focal regions 140) deeper in the tissue. Phasing algorithms could also be employed to enhance the focal regions 140.

As described above, this transducer 34 can also be wired and controlled such that the user can ablate specific sectors, or ablate through all simultaneously. Different wiring conventions may be employed. Individual "+" and "−" leads may be applied to each pair of inner 124 and outer 126 plated regions. Alternatively, a common "ground" may be made by either shorting together all the inner leads, or all the outer leads and then wiring the remaining plated regions individually.

Similarly, it may only be necessary to mask (or remove) the plating on either the inner 124 or the outer 126 layers.

Continuous plating on the inner region 124, for example, with one lead extending from it, is essentially the same as shorting together the individual sectors. However, there may be subtle performance differences (either desirable or not) created when poling the device with one plating surface continuous and the other sectored.

Figure 12:
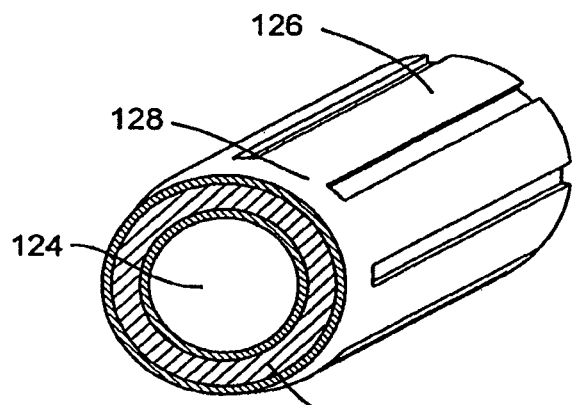
FIG. 12 is a selective plating linked with continuous plating ring.

In addition to the concept illustrated in FIG. 11, it may be desirable to have a continuous plating ring 128 around either or both ends of the transducer 34, as shown in FIG. 12 (continuous plating shown on the proximal outer end only, with no discontinuities on the inner plating). This arrangement could be on either or both the inner and outer plating surface. This allows for one wire connection to drive the given transducer surface at once (the concept in FIG. 11 would require multiple wire connections).

Figure 13:
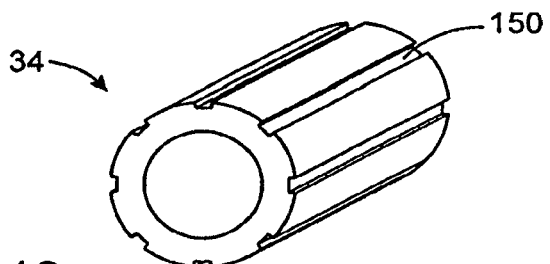
FIG. 13 is a cylindrical transducer with non-resonant channels.

Another means to achieve discrete active sectors in a single cylinder of PZT is to increase or decrease the wall thickness (from the resonant wall thickness) to create non-resonant and therefore inactive sectors. The entire inner and outer surface can be then plated after machining. As illustrated in FIG. 13, channels 150 are machined into the transducer to reduce the wall thickness from the resonant value. As an example, if the desired resonant wall thickness is 0.0110", the transducer can be machined into a cylinder with a 0.0080" wall thickness and then have channels 150 machined to reduce the wall thickness to a non-resonant value (i.e., 0.0090"). Thus, when the transducer 34 is driven at the frequency that resonates the 0.0110" wall, the 0.0090" walls will be non-resonant. Or the transducer 34 can be machined into a cylinder with a 0.015" wall thickness, for example, and then have selective regions machined to the desired resonant wall thickness of, say, 0.0110". Some transducer PZT material is formed through an injection molding or extrusion process. The PZT could then be formed with the desired channels 150 without machining.

Figure 14:
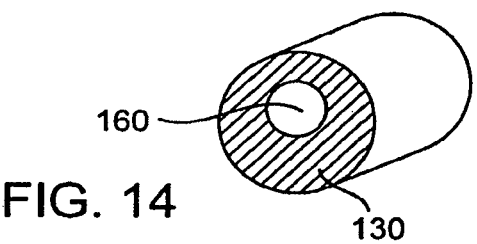
FIG. 14 is a cylindrical transducer with an eccentric core.

Another way to achieve the effect of a discrete zone of resonance is to machine the cylinder such that the central core 160 is eccentric, as shown in FIG. 14. Thus different regions will have different wall thicknesses and thus different resonant frequencies.

It may be desirable to simply run one of the variable wall thickness transducers illustrated above at a given resonant frequency and allow the non-resonant walls to be non-active. However, this does not allow the user to vary which circumferential sector is active. As a result, it may be desirable to also mask/remove the plating in the configurations with variable wall thickness and wire the sectors individually.

In another method of use, the user may gain control over which circumferential sector is active by changing the resonant frequency. Thus the transducer 34 could be machined (or molded or extruded) to different wall thicknesses that resonate at different frequencies. Thus, even if the plating 122 is continuous on each inner 124 and outer 126 surface, the user can operate different sectors at different frequencies. This is also the case for the embodiment shown in FIG. 10 where the individual strips 132 could be manufactured into different resonant thicknesses. There may be additional advantages of ensuring different depths of heating of different sectors by operating at different frequencies. Frequency sweeping or phasing may also be desirable.

For the above transducer designs, longitudinal divisions are discussed. It is conceivable that transverse or helical divisions would also be desirable. Also, while the nature of the invention relates to a cylindrical transducer, the general concepts of creating discrete zones of resonance can also be applied to other shapes (planar, curved, spherical, conical, etc.). There can also be many different plating patterns or channel patterns that are conceivable to achieve a particular energy output pattern or to serve specific manufacturing needs.

Except where specifically mentioned, the above transducer embodiments have a relatively uniform energy concentration as the ultrasound propagates into the tissue. The following transducer designs relate to configurations that focus the energy at some depth. This is desirable to minimize the heating of the tissue at the mucosal surface but create a lesion at some depth.

One means of focusing the energy is to apply a cover layer "lens" 170 (not shown) to the surface of the transducer in a geometry that causes focusing of the acoustic waves emanating from the surface of the transducer 34. The lens 170 is commonly formed out an acoustically transmissive epoxy that has a speed of sound different than the PZT material 130 and/or surrounding coupling medium. The lens 170 could be applied directly to the transducer, or positioned some distance away from it. Between the lens 170 and the transducer may be a coupling medium of water, gel, or similarly non-attenuating material. The lens could be suspended over (around) the transducer 34 within the balloon 46, or on the balloon itself.

Figure 15:
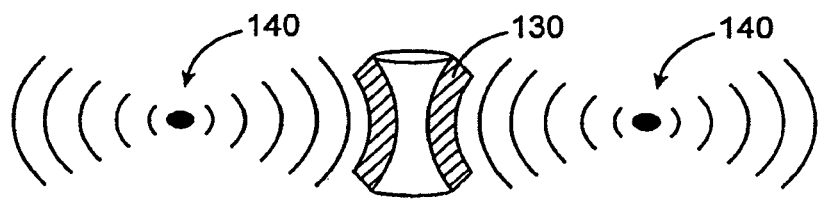
FIG. 15 is a cylindrical transducer with curved cross-section and resulting focal region of acoustic energy.

In another embodiment, the cylindrical transducer 34 can be formed with a circular or parabolic cross section. As illustrated in FIG. 15, this design allows the beam to have focal regions 140 and cause higher energy intensities within the wall of the tissue.

Figure 16:
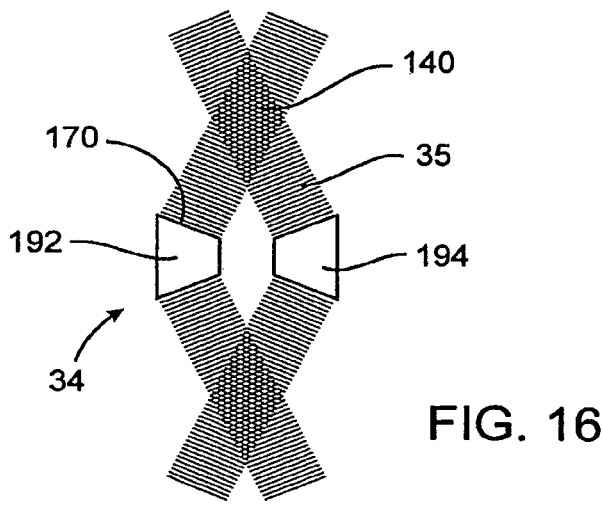
FIG. 16 is an illustration of acoustic output from conical transducers.

In another embodiment shown in FIG. 16, angled strips or angled rings (cones) allow forward and/or rear projection of ultrasound (acoustic energy 35). Rearward projection of ultrasound 35 may be particularly useful to heat the underside of the LES 18 or cardia 20 when the transducer element 34 is positioned distal to the LES 18. Each cone could also have a concave or convex shape, or be used with a lensing material 170 to alter the beam shape. In combination with opposing angled strips or cones (forward 192 and rearward 194) the configuration allows for focal zones of heating 140.

Figure 17:
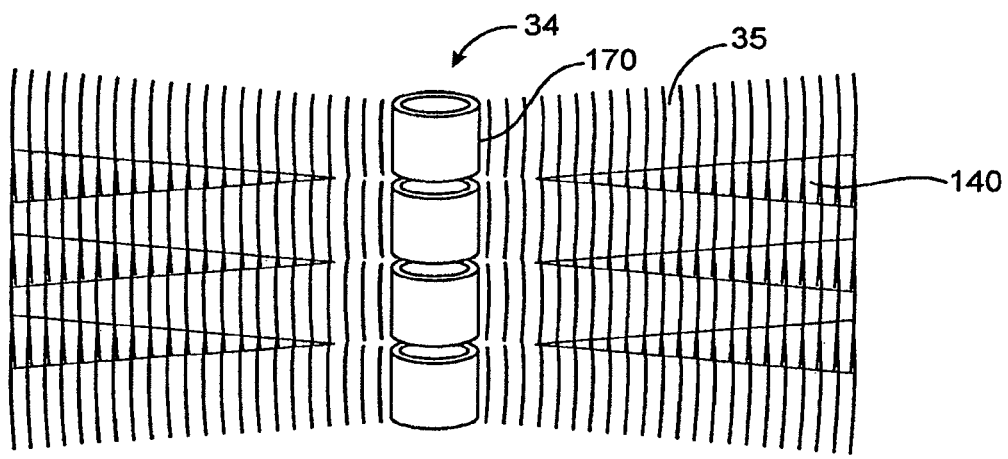
FIG. 17 is a longitudinal array of cylindrical transducers.

In another embodiment, shown in FIG. 17, multiple rings (cylinders) of PZT transducers 34 would be useful to allow the user to change the ablation location without moving the catheter. This also allows for regions of constructive/destructive interference (focal regions 140) when run simultaneously. Anytime multiple elements are used, the phase of the individual elements may be varied to "steer" the most intense region of the beam in different directions. Rings could also have a slight convex shape to enhance the spread and overlap zones, or a concave shape to focus the beam from each ring. Pairs of opposing cones or angled strips (described above) could also be employed. Each ring could also be used in combination with a lensing material 170 to achieve the same goals.

Transducer Mounting: One particular challenge in designing transducers that deliver significant power (approximately 10 acoustic watts per cm.sup.2 at the transducer surface, or greater) is preventing the degradation of adhesives and other heat/vibration sensitive materials in proximity to the transducer. If degradation occurs, materials under or over the transducer can delaminate and cause voids that negatively affect the acoustic coupling and impedance of the transducer. In cases where air backing of the transducer is used, material degradation can lead to fluid infiltration into the air space that will compromise transducer performance. Some methods of preventing degradation are described below.

Figure 18:
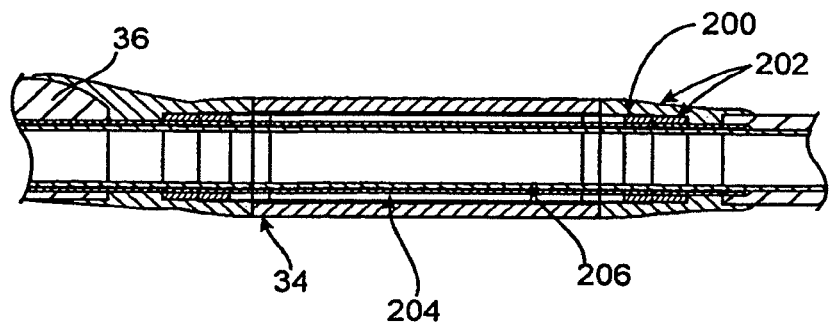
FIG. 18 is a transducer mounting configuration using metal mounts.

In FIG. 18, a preferred means of mounting the transducer 34 is to securely bond and seal (by welding or soldering) the transducer to a metal mounting member 200 that extends beyond the transducer edges. Adhesive attachments 202 can then be made between the mounting member 200 extensions remote to the transducer 34 itself. The mounting member(s) can provide the offsets from the underlying mounting structure 206 necessary to ensure air backing between the transducer 34 and the underlying mounting structure 206. One example of this is shown in FIG. 18 where metal rings 200 are mounted under the ends of the transducer 34. The metal rings 200 could also be attached to the top edges of the transducer 34, or to a plated end of the transducer. It may also be possible to mechanically compress the metal rings against the transducer edges. This could be accomplished through a swaging process or through the use of a shape-memory material such as nitenol. It may also be possible to use a single metal material under the transducer as the mounting member 200 that has depressions (i.e. grooves, holes, etc.) in the region under the transducer to ensure air backing. A porous metal or polymer could also be placed under the transducer 34 (with the option of being in contact with the transducer) to provide air backing.

Figure 19:
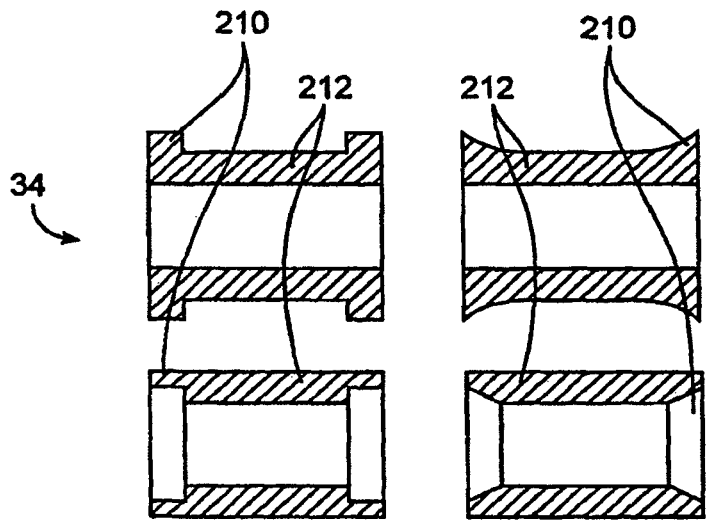
FIG. 19 shows transducer geometry variations used to enhance mounting integrity.

In FIG. 19, another means of mounting the transducer 34 is to form the transducer 34 such that non-resonating portions 210 of the transducer 34 extend away from the central resonant section 212. The benefit is that the non-resonant regions 210 are integral with the resonant regions 212, but will not significantly heat or vibrate such that they can be safely attached to the underlying mounting structure 206 with adhesives 202. This could be accomplished by machining a transducer 34 such that the ends of the transducer are thicker (or thinner) than the center, as shown in FIG. 19.

Figure 20:
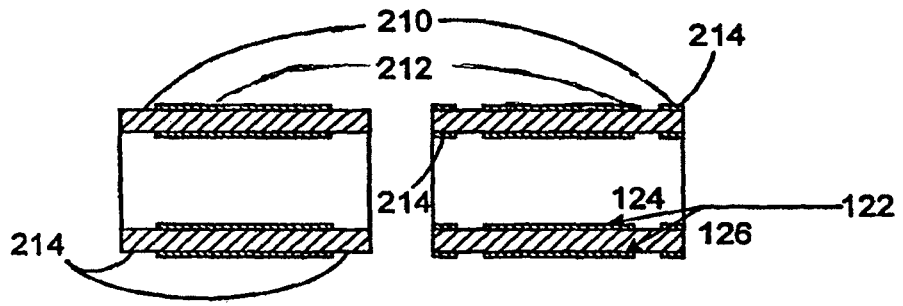
FIG. 20 is transducer plating variations used to enhance mounting integrity.

As shown in FIG. 20, another option is to only plate the regions of the transducer 34 where output is desired, or interrupt the plating 122 such that there is no electrical conduction to the mounted ends 214 (conductor wires connected only to the inner plated regions).

The embodiments described in FIGS. 18-20 can also be combined as necessary to optimize the mounting integrity and transducer performance.

Cooling Design Configurations: Cooling flow may be necessary to 1) Prevent the transducer temperature from rising to levels that may impair performance, and 2) Prevent the mucosal lining of the sphincter from heating to the point of irreversible damage. The following embodiments describe the various means to meet these requirements.

Figure 21:
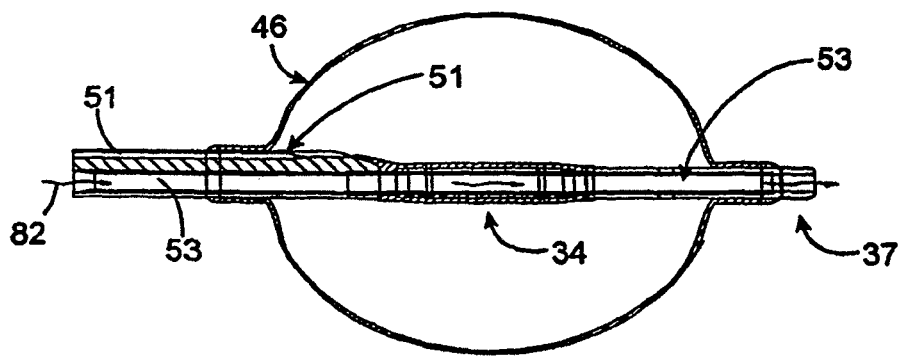
FIG. 21 shows cooling flow through the catheter center lumen, exiting the tip.

FIG. 21 shows cooling fluid 82 being passed through a central lumen 53 and out the distal tip 37 to prevent heat buildup in the transducer 34. The central column of fluid 82 serves as a heat sink for the transducer 34.

Figure 22:
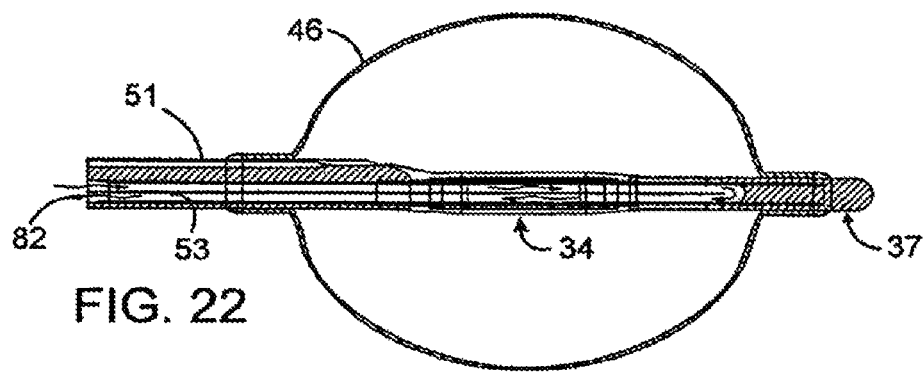
FIG. 22 shows cooling flow recirculating within the catheter central lumen.

FIG. 22 is similar to FIG. 21 except that the fluid 82 is recirculated within the central lumen 53 (actually a composition of two or more lumens), and not allowed to pass out the distal tip 37.

Figure 23:
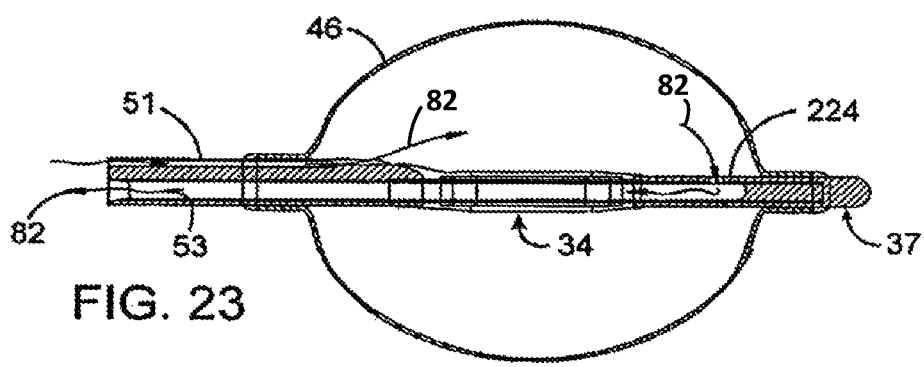
FIG. 23 shows cooling flow circulating within the balloon.

FIG. 23 (also shown a part of the preferred embodiment of FIG. 2) shows the fluid circulation path involving the balloon itself. The fluid enters through the balloon inflation lumen 51 and exits through one or more ports 224 in the central lumen 53, and then passes proximally out the central lumen 53. The advantage of this embodiment is that the balloon 46 itself is kept cool, and draws heat away from the mucosal lining of the sphincter. Pressure of the recirculating fluid 82 would have to be controlled within a tolerable range to keep the balloon 46 inflated the desired amount. Conceivably, the central lumen 53 could be the balloon inflation lumen, with the flow reversed with respect to that shown in FIG. 23. Similarly, the flow path does not necessarily require the exit of fluid in the central lumen 53 pass under the transducer 34—fluid 82 could return through a separate lumen located proximal to the transducer.

In another embodiment (not shown), the balloon could be made from a porous material that allowed the cooling fluid to exit directly through the wall of the balloon. Examples of materials used for the porous balloon include open cell foam, ePTFE, porous urethane or silicone, or a polymeric balloon with laser-drilled holes. It is also conceivable that if a conductive media, such as saline is used for the cooling fluid, and a ground patch attached to the patient, electrical RF energy from the outer plating of the transducer could be allowed to pass into the tissues and out to the ground patch, resulting in a combination of acoustic and RF heating of the tissue.

Figure 24:
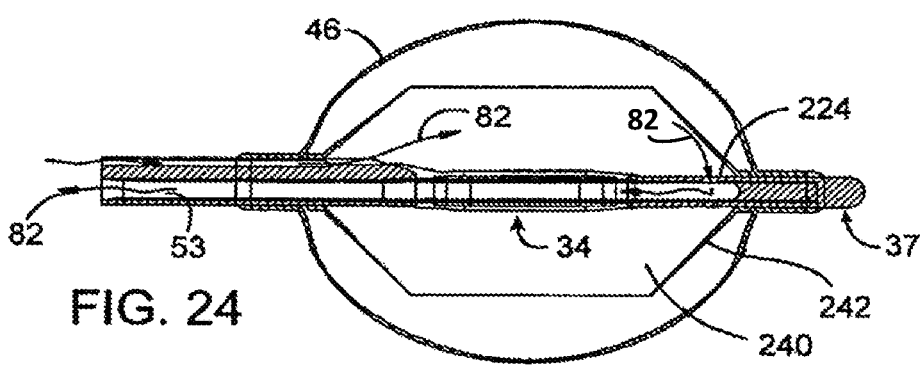
FIG. 24 shows cooling flow circulating within a lumen/balloon covering the transducer.

FIG. 24 shows the encapsulation of the transducer 34 within another lumen 240. This lumen 240 is optionally expandable, formed from a compliant or non-compliant balloon material 242 inside the outer balloon 46 (the lumen for inflating the outer balloon 46 is not shown). This allows a substantial volume of fluid to be recirculated within the lumen 240 without affecting the inflation pressure/shape of the outer balloon 46 in contact with the sphincter. Allowing a substantial inflation of this lumen decreases the heat capacity of the fluid in the balloon in contact with the sphincter and thus allows for more efficient cooling of the mucosal lining. Fluid 82 could also be allowed to exit the distal tip. It can also be imagined that a focusing lens material 170 previously described could be placed on the inner or outer layer of the lumen material 242 surrounding the transducer 34.

Figure 25:
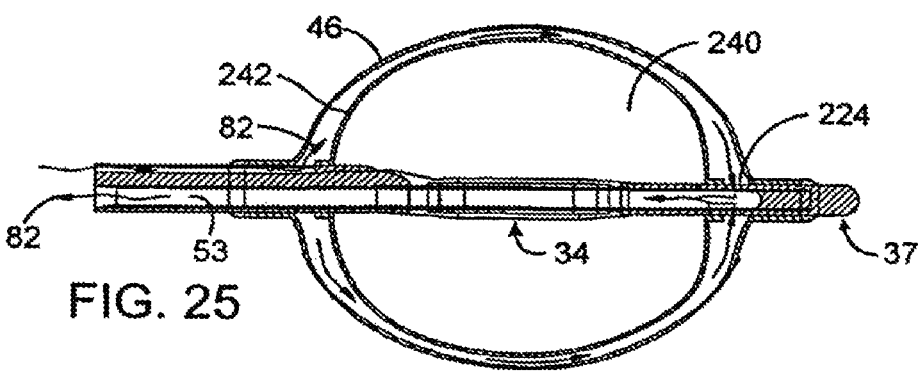
FIG. 25 shows cooling flow circulating between an inner and an outer balloon.

As is shown in FIG. 25, there can be an outer balloon 46 that allows circulation over the top of the inner balloon 242 to ensure rapid cooling at the interface. To ensure flow between the balloons, the inner balloon 242 can be inflated to a diameter less than the outer balloon 46. Flow 82 may be returned proximally or allowed to exit the distal tip. Another version of this embodiment could make use of raised standoffs 250 (not shown) either on the inside of the outer balloon 46 or the outside of the inner balloon 242, or both. The standoffs 250 could be raised bumps or splines. The standoffs 250 could be formed in the balloon material itself, from adhesive, or material placed between the balloons (i.e., plastic or metal mandrels). The standoffs 250 could be arranged longitudinally or circumferentially, or both. While not shown in a figure, it can be imagined that the outer balloon 46 shown in FIG. 25 may only need to encompass one side (i.e., the proximal end) of the inner balloon, allowing sufficient surface area for heat convection away from the primary (inner) balloon 242 that in this case may be in contact with the tissue. In the case of treating Barrett's Esophagus, the space between the two balloons may be filled with an oil suspension or other fluidic or thixotropic medium that has relatively high acoustic attenuation properties. The medium does not necessarily need to recirculate. The intent is that this space between the balloons will preferentially heat and necrose the intestinal metaplasia lining the esophagus.

Figure 26:
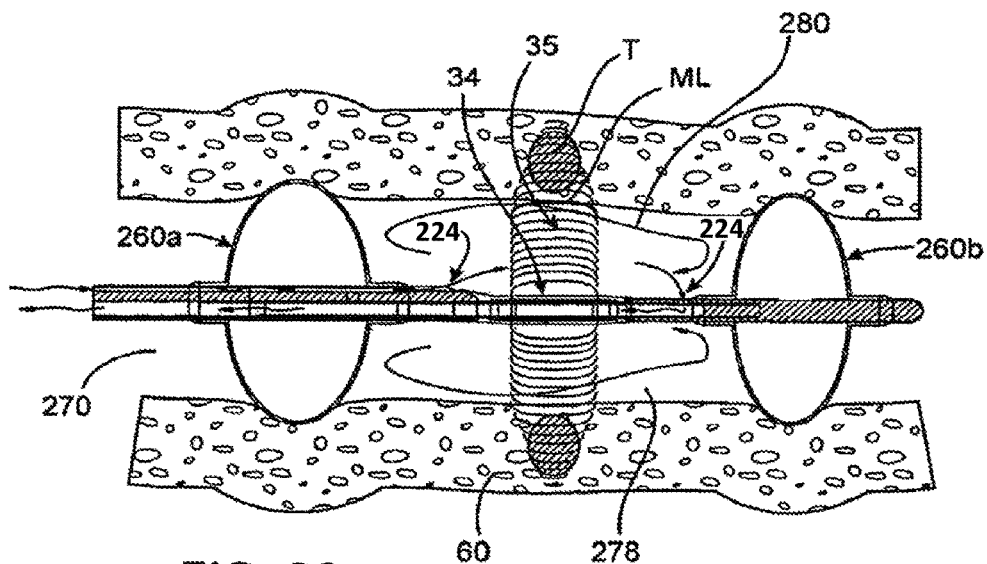
FIG. 26 is an ultrasound ablation element bounded by tandem occluding members.

In another embodiment, illustrated in FIG. 26, occluding members 260 are positioned proximal (260*a*) and distal (260*b*) to the transducer element for occluding the sphincter lumen 270. The occluding members 260 may also serve to dilate the sphincter region to a desired level. The occluding members 260 are capable of being expanded from a collapsed position (during catheter delivery) for occlusion. Each occluding member 260 is preferably an inflatable balloon, but could also be a self-expanding disk or foam material, or a wire cage covered in a polymer, or combination thereof. To deploy and withdraw a non-inflatable occluding member, either a self-expanding material could be expanded and compressed when deployed out and back in a sheath, or the occluding member could be housed within a braided or other cage-like material that could be alternatively cinched down or released using a pull mechanism tethered to the proximal end of the catheter 30. It may also be desirable for the occluding members 260 to have a "textured" surface to prevent slippage of the device. For example, adhesive spots could be applied to the outer surface of the balloon, or the self-expanding foam could be fashioned with outer ribs.

With the occluding members 260 expanded against the sphincter lumen, the chamber 278 formed between the balloons is then filled with a fluid or gel 280 that allows the acoustic energy 35 to couple to the tissue 60. To prevent heat damage to the mucosal lining ML of the tissue lumen 270, the fluid/gel 280 may be chilled and/or recirculated. Thus with cooling, the lesion formed within a target site T the tissue 60 is confined inside the tissue wall and not formed at the inner surface. This cooling/coupling fluid 280 may be routed into and out of the space between the occluding members with single entry and exit port, or with a plurality of ports. The ports can be configured (in number, size, and orientation) such that optimal or selective cooling of the mucosal surface is achieved. Note also that cooling/coupling fluid 280 routed over and/or under the transducer 34 helps keep the transducer cool and help prevent degradation in performance.

The transducer element(s) 34 may be any of those previously described. Output may be completely circumferential or applied at select regions around the circumference. It is also conceivable that other energy sources would work as well, including RF, microwave, laser, and cryogenic sources.

Figure 27:
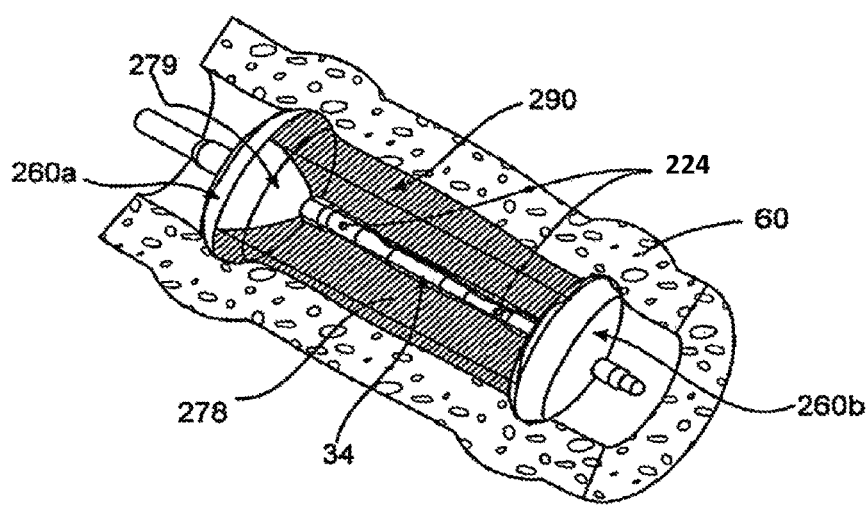
FIG. 27 shows sector occlusion for targeted ablation and cooling.

In the case where only certain sectors of tissue around the circumference are treated, it may be desirable to utilize another embodiment, shown in FIG. 27, of the above embodiment shown in FIG. 26. In addition to occluding the proximal and distal ends, such a design would use a material 290 to occlude regions of the chamber 278 formed between the distal and proximal occluding members 260. This would, in effect, create separate chambers 279 around the circumference between the distal and proximal occluding members 260, and allow for more controlled or greater degrees of cooling where energy is applied. The material occluding the chamber could be a compliant foam material or an inflatable balloon material attached to the balloon and shaft. The transducer would be designed to be active only where the chamber is not occluded.

Temperature Monitoring: The temperature at the interface between the tissue and the balloon may be monitored using thermocouples, thermistors, or optical temperature probes. Although any one of these could be used, for the illustration of various configurations below, only thermocouples will be discussed. The following concepts could be employed to measure temperature.

Figure 28:
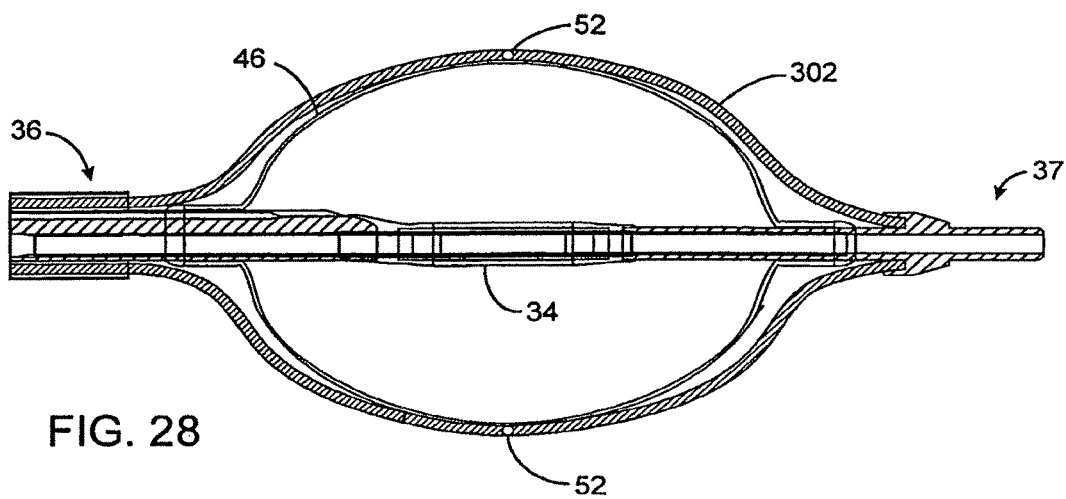
FIG. 28 shows thermocouples incorporated into proximally slideable splines positioned over the outside of the balloon.

In one embodiment shown in FIG. 28, one or more splines 302, supporting one or more temperature sensors 52 per spline, run longitudinally over the outside of the balloon 46. On each spline 302 are routed one or more thermocouple conductors (actually a pair of wires) 306. The temperature sensor 52 is formed at the electrical junction formed between each wire pair in the conductor 306. The thermocouple conductor wires 306 could be bonded straight along the spline 302, or they could be wound or braided around the spline 302, or they could be routed through a central lumen in the spline 302.

At least one thermocouple sensor 52 aligned with the center of the ultrasound beam 35 is desired, but a linear array of thermocouple sensors 52 could also be formed to be sure at least one sensor 52 in the array is measuring the hottest temperature. Software in the generator 70 may be used to calculate and display the hottest and/or coldest temperature in the array. The thermocouple sensor 52 could be inside or flush with the spline 302; however, having the sensor formed in a bulb or prong on the tissue-side of the spline 302 is preferred to ensure it is indented into the tissue. It is also conceivable that a thermocouple placed on a slideable needle could be used to penetrate the tissue and measure the submucosal temperature.

Each spline 302 is preferably formed from a rigid material for adequate tensile strength, with the sensors 52 attached to it. Each individual spline 302 may also be formed from a braid of wires or fibers, or a braid of the thermocouple conductor wires 306 themselves. The splines 302 preferably have a rectangular cross section, but could also be round or oval in cross section. To facilitate deployment and alignment, the splines 302 may be made out a pre-shaped stainless steel or nitenol metal. One end of the spline 302 would be fixed to the catheter tip 37, while the proximal section would be slideable inside or alongside the catheter shaft 36 to allow it to move with the balloon 46 as the balloon inflates. The user may or may not be required to push the splines 302 (connected to a proximal actuator, not shown) forward to help them expand with the balloon 46.

The number of longitudinal splines could be anywhere from one to eight. If the transducer 34 output is sectored, the splines 302 ideally align with the active transducer elements.

In a related embodiment, a braided cage (not shown) could be substituted for the splines 302. The braided cage would be expandable in a manner similar to the splines 302. The braided cage could consist of any or a combination of the following: metal elements for structural integrity (i.e., stainless steel, nitenol), fibers (i.e., Dacron, Kevlar), and thermocouple conductor wires 306. The thermocouple sensors 52 could be bonded to or held within the braid. For integrity of the braid, it may be desirable for the thermocouple conductors 306 to continue distal to the thermocouple junction (sensor) 52. The number structural elements in the braid may be 4 to 24.

Figure 29:
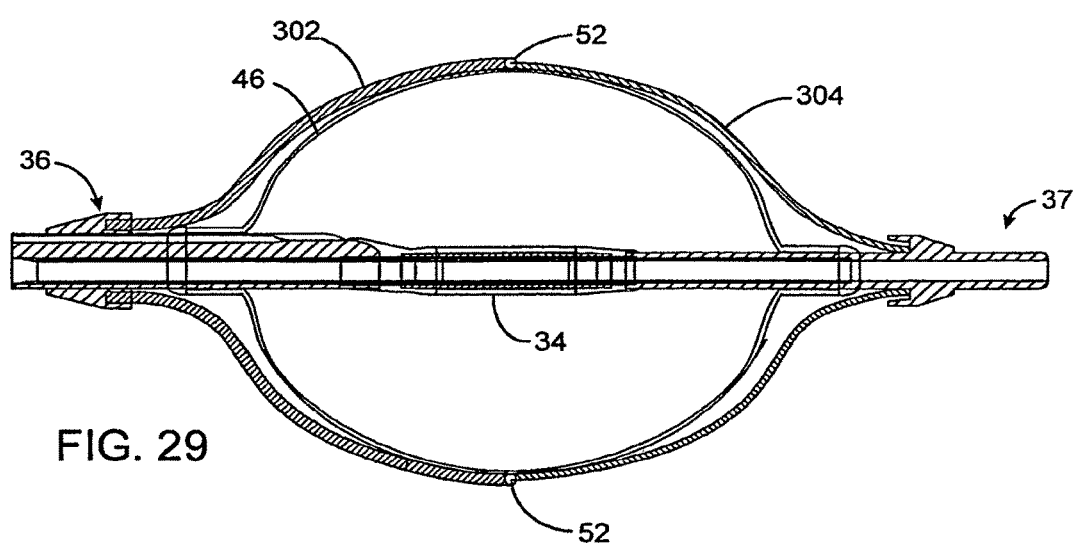
FIG. 29 shows thermocouples incorporated into splines fixed to the shaft but tethered to the distal end with an elastic member.

In another embodiment shown in FIG. 29, a design similar to the embodiment above is used, except the distal end of the spline 302 is connected to a compliant band 304 that stretches over the distal end of the balloon as the balloon inflates. The band 304 may be formed out of a low durometer material such as silicone, urethane, and the like. It may also be formed from a wound metal spring. The spline 302 proximal to the balloon may then be fixed within the catheter shaft 36. Of course the arrangement could be reversed with the spline 302 attached to the distal end of the balloon 46, and the compliant band 304 connected to the proximal shaft 36.

Figure 30:
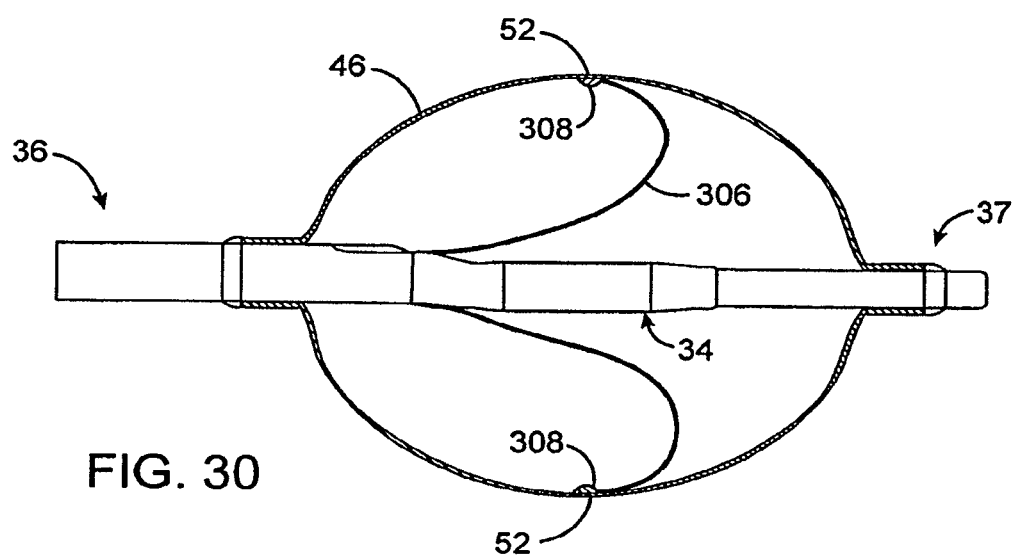
FIG. 30 shows thermocouples attached to the inside of the balloon, aligned with the ultrasound transducer.

In another embodiment shown in FIG. 30, the sensors 52 are bonded with adhesive 308 to the inside of the balloon (in the path of the ultrasound beam 35). The adhesive 308 used is ideally a compliant material such as silicone or urethane if used with a compliant balloon. It may also be a cyanoacrylate, epoxy, or UV cured adhesive. The end of the conductor wire 306 at the location of the sensor 52 is preferably shaped into a ring or barb or the like to prevent the sensor from pulling out of the adhesive. Multiple sensors 52 may be arranged both circumferentially and longitudinally on the balloon 46 in the region of the ultrasound beam 35. Thermocouple conductor wires 306 would have sufficient slack inside the balloon 46 to expand as the balloon inflates.

In another embodiment (not shown), the thermocouple conductor wires are routed longitudinally through the middle of the balloon wall inside preformed channels.

Figure 31:
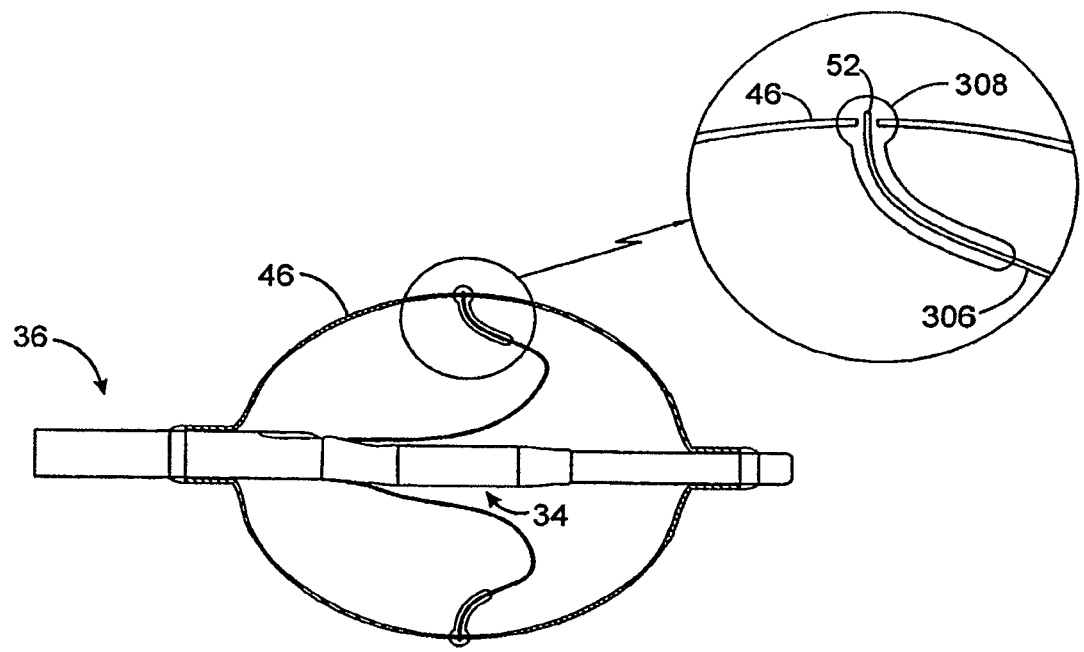
FIG. 31 shows thermocouples positioned on the outside of the balloon, aligned with the ultrasound transducer, and routed across the wall and through the inside of the balloon.

In another embodiment shown in FIG. 31, the thermocouple sensors 52 are bonded to the outside of the balloon 46, with the conductor wires 306 routed through the wall of the balloon 46, in the radial direction, to the inside of the balloon 46 and lumens in the catheter shaft 36. The conductor wires 306 would have sufficient slack inside the balloon to expand as the balloon inflates. To achieve the wire routing, a small hole is punched in the balloon material, the conductor wire routed through, and the hole sealed with adhesive. The conductor wire could be coated in a material that is bondable with the balloon (i.e., the balloon material itself, or a compatible adhesive 308 as described for FIG. 30) prior to adhesive bonding to help ensure a reliable seal.

Figures 32A, 32B, 32C:
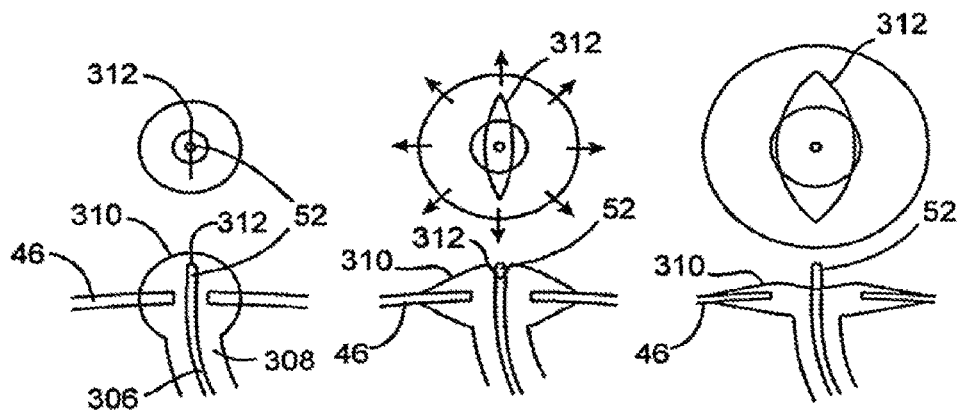
FIGS. 32*a*-32*c* show the use of a slit in the elastic encapsulation of a thermocouple bonded to the outside of an elastic balloon that allows the thermocouple to become exposed during balloon inflation.

In another embodiment shown in FIGS. 32a-32c, the thermocouple sensors 52 mounted on the outer surface of the balloon (regardless of how the wires 306 are routed) are housed in raised bulbs 310 of adhesive 308 (or a molded section of the balloon material itself) that help ensure they are pushed into the tissue, allowing more accurate tissue temperature measurement that is less susceptible to the temperature gradient created by the fluid in the balloon. For compliant balloons, a stiff exposed sensor 52 could be housed in a bulb of compliant material with a split 312. As the balloon 46 inflates, the split 312 in the bulb 210 opens and exposes the sensor 52 to the tissue. As the balloon 46 deflates, the bulb 310 closes back over the sensor 52 and protects it during catheter manipulation in the body.

In another embodiment (not shown), an infrared sensor pointed toward the heat zone at the balloon-tissue interface could be configured inside the balloon to record temperatures in a non-contact means.

For the embodiments described in either FIG. 26 or FIG. 27 above, it may also be desirable to monitor the temperature of the tissue during energy delivery.

This would be best accomplished through the use of thermocouples aligned with the ultrasound beam emanating from the transducer. Each thermocouple would monitor the temperature of the mucosal surface to ensure that the appropriate amount of power is being delivered. Power can be decreased manually or though a feedback control mechanism to prevent heat damage to the mucosa, or the power can be increased to a predetermined safe mucosal temperature rise to ensure adequate power is being delivered to the submucosa.

Figure 33:
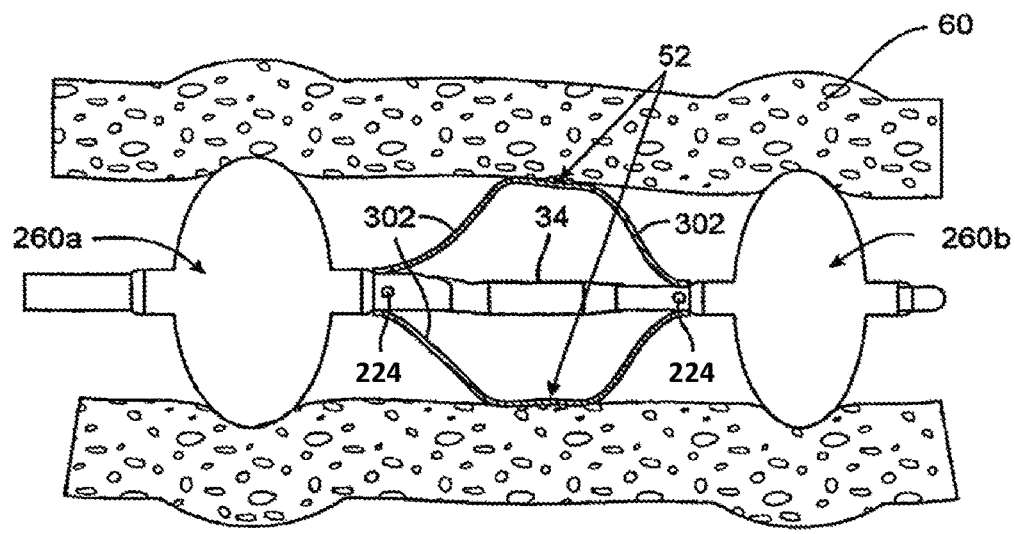
FIG. 33 shows thermocouples mounted on splines between two occluding balloons and aligned with the transducer.

As shown in FIG. 33, the thermocouple sensors 52 could be mounted on splines 302 similar in design, construction, and operation to those described previously. In this configuration, the splines 302 are expanded against the tissue without the use of an interior balloon. They are deployed before, during, or after the occlusion members 260 are expanded. The braided cage configuration described above may also be used.

In another embodiment (not shown), the splines 302 or braided cage containing the thermocouple sensors 52 could span over the top of either or both expandable occlusive members 260. If the occlusive members 260 are balloons, the balloons act to expand the cage outward and against the tissue. If the occlusive members 206 are made from a self-expanding foam or disk material, the cage can be used to contain the occlusive material 206 during advancement of the catheter by holding the individual components of the cage down against the shaft under tension. Once positioned at the site of interest, the cage can be manually expanded to allow the occlusive members 260 to self-expand.

The direction of ultrasound delivery to this point has mostly been described as moving radially into the tissues of the esophagus, LES, and/or gastric cardia. Other system embodiments described below may be employed to aid in using an ablation device that delivers energy in a variety of directions into the tissue. For example, the ablation device can be oriented such that the energy is applied through the longitudinal axis of the sphincter wall, as opposed to radially through the wall. This has the advantage of preventing energy from passing through the outer wall where surrounding structures, such as the vagal nerves, liver, aorta, and mediastinum reside. In addition, longitudinal lesions may help reduce the axial compliance of the sphincter, preventing it from shortening and thus delaying how soon it opens as the gastric pressure increases. The designs also lend themselves to use of a planar or partial arc transducer that can be more reliably fabricated into a thinner wall than a cylindrical (for circumferential output) transducer. This allows for operation at higher frequencies that increases energy attenuation in the tissue and limits the depth of penetration of the ultrasound energy. In this instance, radial direction of the energy is more feasible without damage to collateral structures. Finally, particular embodiments of this invention may make lesion formation in the gastric cardia easier than is possible with a circumferential system. Lesions created on the "underside" of the sphincter in the region of the gastric cardia may help reduce the compliance of the gastric sling fibers in this region. This may help delay opening of the sphincter as the stomach expands due to increases in gastric pressure. The region of the gastric cardia may also have more vagal innervation responsible for transient relaxations of the sphincter; the lesions would reduce this innervation.

Figure 34A:
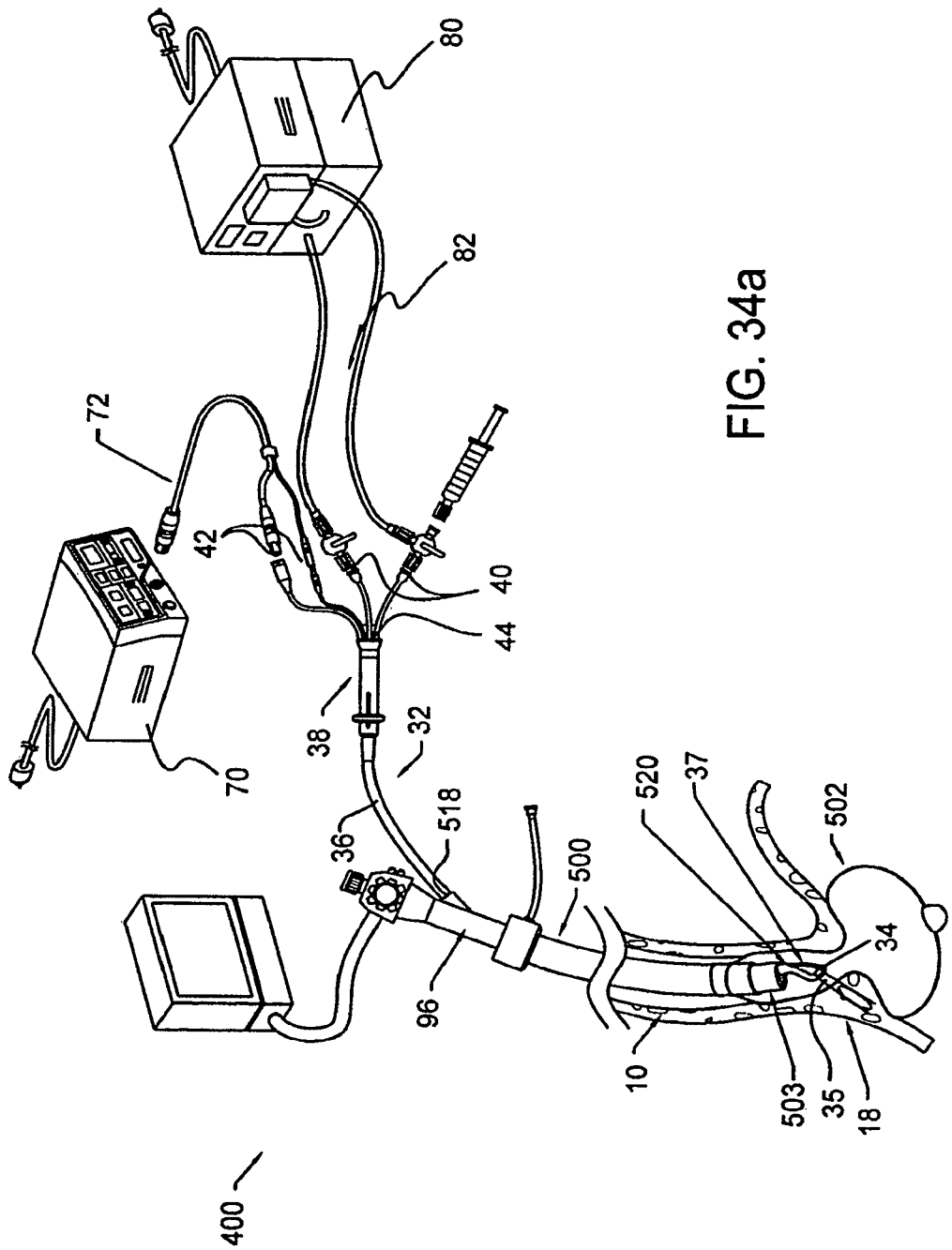
FIG. 34*a* is an Ultrasound Ablation System for GERD Treatment that includes an ablation catheter with a tip controllable from a member attached to the distal tip.

As shown in FIG. 34a, the present invention relates to an ablation system 400 consisting of an ablation catheter 32 with an acoustic energy delivery element (ultrasound transducer) 34 mounted on the distal end of the catheter. The device is delivered transorally to the region of the LES 18. The system 400 consists of the following key components:

1. An overtube 500 having a balloon 502 attached to the distal opening 503.
2. An endoscope 96 having at least one therapeutic channel 518 greater than 2.8 mm.
3. A catheter 32 having a shaft 36 and a proximal hub/handle 38 containing fluid ports 40, electrical connectors 42, and optional central guidewire lumen port 44. The catheter also has an ultrasound transducer 34 on a mounting 37 that produces acoustic energy 35 at the distal end of the distal catheter shaft 520
4. An energy generator 70 and connector cable(s) 72 for driving the transducer and displaying temperature values
5. A fluid pump 80 delivering cooling fluid 82.

Figure 34B:
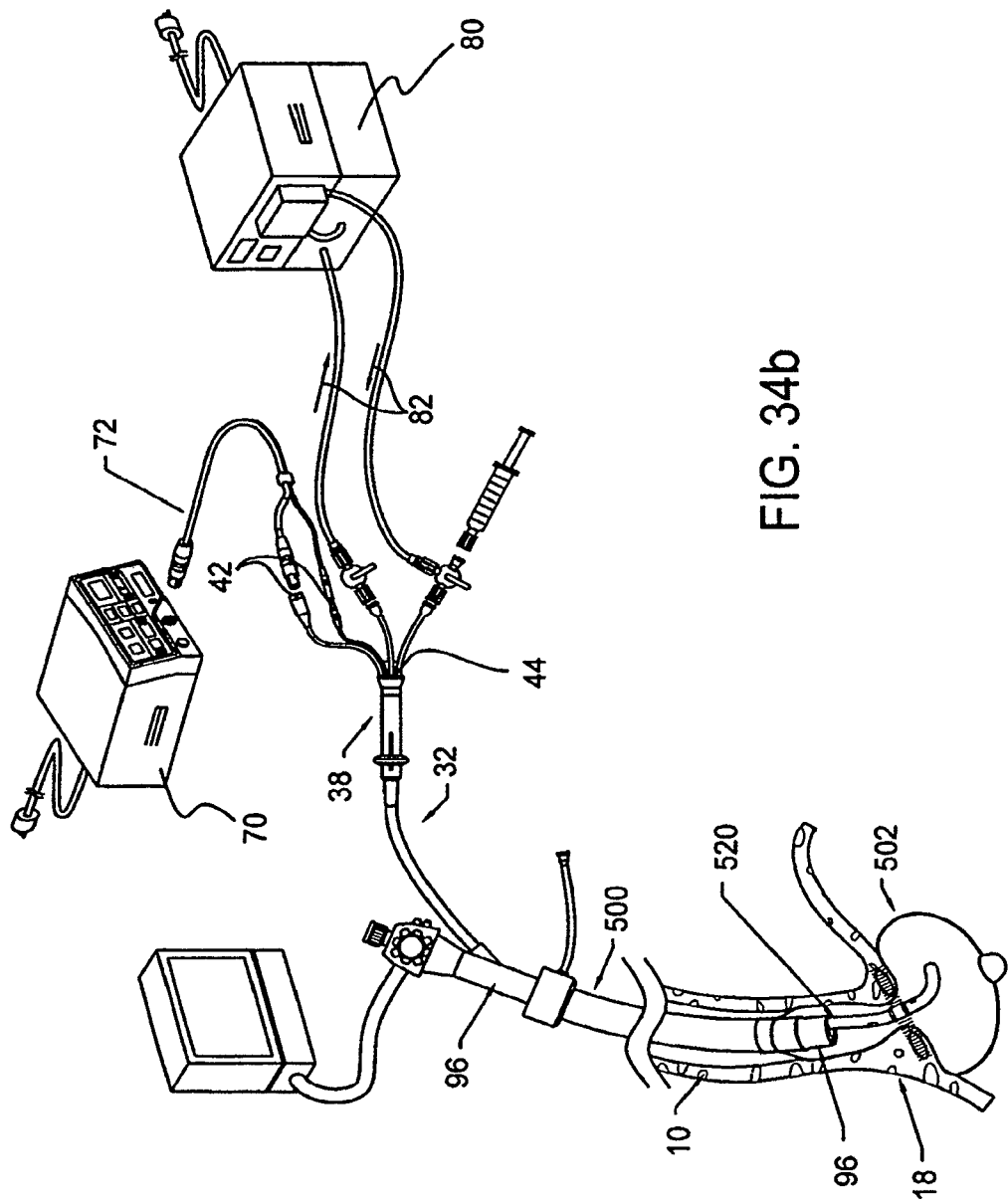
FIG. 34*b* is an Ultrasound Ablation System for GERD Treatment that includes an ablation catheter with a tip optionally controlled via an internal tensioning mechanism.

FIG. 34b illustrates a similar system where the ablation catheter 32 makes use of a transducer 34 designed to deliver acoustic energy radially (either circumferentially or in one or more discrete sectors) from the longitudinal axis. The catheter 32 can be moved with respect to the overtube balloon 502. The tip of the catheter may also be deflectable from an actuator on the proximal hub/handle 38.

While use of the catheter 32 through a channel in the endoscope 96 is preferred, it is conceivable that the catheter 32 could be deployed through the overtube 500 without the use of the endoscope 96.

Figure 35:
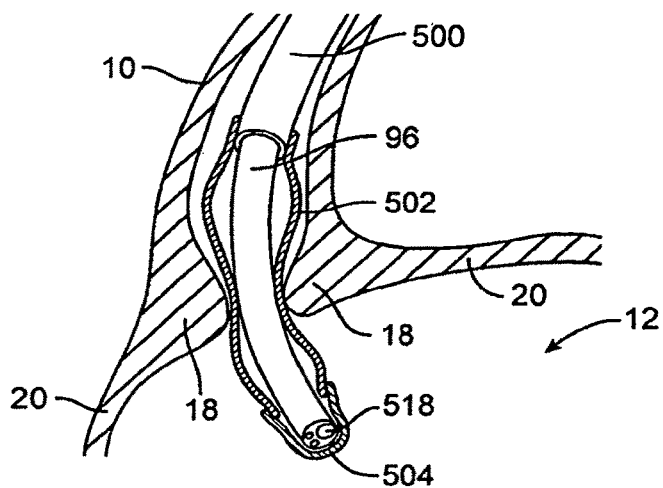
FIG. 35 illustrates the deployment of an overtube with balloon over an endoscope.

The preferred method of ablation treatment is illustrated in FIGS. 35-39. In FIG. 35, an overtube device 500 having a peanut-shaped balloon 502 is preloaded over an endoscope 96. The balloon 502 is preferably made of a compliant material such as silicone or polyurethane, but could also be a material such as polyethylene or PET. The wall thickness of the balloon is preferably thicker in the middle of the "peanut" to limit the degree of radial expansion compared to the proximal and distal sections. Alternatively the middle of the balloon is simply blown or molded to a smaller diameter. The tip of the overtube balloon 502 is fitted with a relatively rigid nipple-shaped dome 504 that allows a snug fit with the tip of the endoscope. The dome 504 may be an integral, thickened portion of the balloon itself, or a separate component that the balloon is bonded to. It is conceivable that to aid seating the endoscope 96 in the dome 504 and make later release more reliable, the tip of the endoscope could be secured to the dome with the aid of one of the available endoscope channels. For instance, suction from a channel of the endoscope 96 could be applied to hold the dome against the endoscope tip, or a screw or barb or other grasping mechanism could be advanced through the channel to secure the dome tip to the tip of the endoscope. Also, vacuum may be applied to the balloon 502 using the lumen of the overtube 500, or from a lumen of the endoscope 96, to fold the balloon 502 down onto the endoscope. The proximal end of the overtube 502 is fitted with appropriate stasis valves to prevent leakage out the proximal end. The balloon 502 and/or the dome 504 should be transparent to allow visualization of tissue structures through the balloon wall.

An optional embodiment (not shown) would be the use of a vent tube alongside the overtube 500 and overtube balloon 520 to allow air in the stomach to vent out of the patient. The tube could be positioned completely separate from the overtube or advanced through an optional lumen in the overtube, exiting just proximal to the overtube balloon 520. The distal end of the vent tube would be positioned in the stomach 20 distal to the overtube balloon 520. The tube is preferably relatively stiff at the proximal end (for push transmission), and floppy at the distal end so that it is atraumatic and conforms well to the overtube balloon 520 as the balloon entraps the vent tube against the tissue. While the inner diameter of the vent tube needs to be only on the order of 0.005" to vent air, larger inner diameters up to 0.042" may be used to speed the aspiration of fluids or allow the passage of a guide wire (for ease in placement). The wall thickness may be 0.003" to 0.010", preferably, 0.004". The wall of the tube may be a solid material, or a composite of plastic and adhesives and/or stainless steel or nitenol wires or Dacron fibers. The wall may consist of stainless steel, nitenol, or a plastic such as polyurethane, pebax, polyethylene, PET, polyimide, or PVC.

Figure 36:
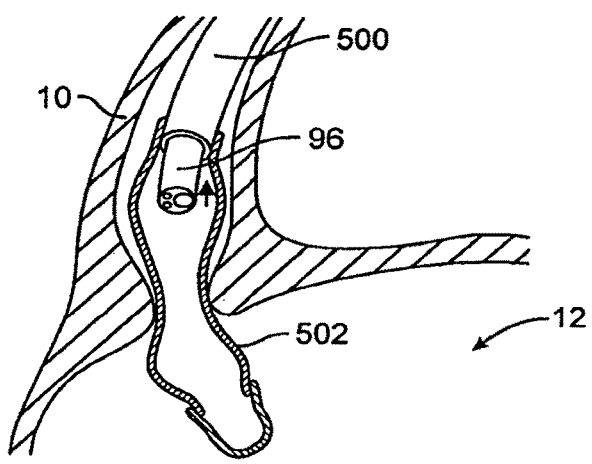
FIG. 36 illustrates retraction of the endoscope within the balloon of the overtube.

With the endoscope 96 seated in the dome 504 of the balloon 502, the overtube 500 and endoscope 96 are advanced down the esophagus 10 to the region of the LES 18. As illustrated in FIG. 36, using endoscopy visualization, and retracting the endoscope as necessary, the balloon is positioned so that the peanut shape straddles the LES 18.

Figure 37:
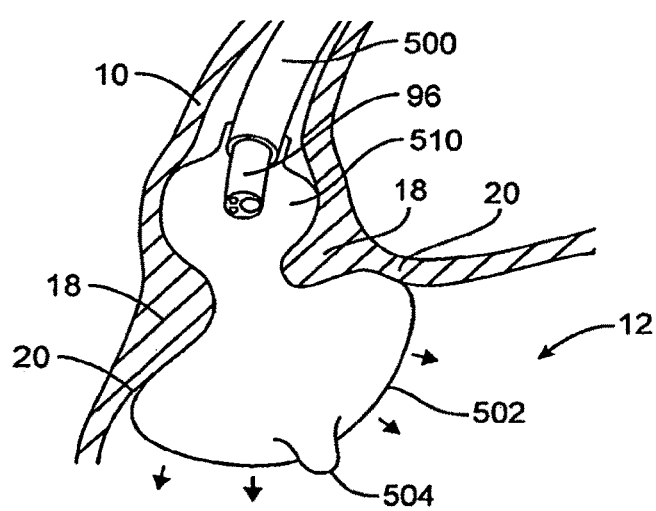
FIG. 37 illustrates inflation of the overtube balloon at the region of the Lower Esophageal Sphincter (LES).

The balloon is then inflated with a fluid medium (water, saline, contrast, etc.) as illustrated in FIG. 37. Inflation is performed preferably through the lumen of the overtube, although an available channel in the endoscope 96, or lumens in the ablation catheter 32 may also be used. The shape of the balloon allows it to conform to the contours of the esophagus at, and on either side of, the LES. The shape also helps stabilize the balloon at the LES. The balloon is inflated to a diameter that allows safe dilatation of the folds in the esophagus. The nominal inflated diameter of the proximal section 510 should be 20 mm, with a range of 15-30 mm. The distal section 512 can be larger, nominally 40 mm and a range of 15-50 mm. Diameter may be assessed by fluid volume, pressure, endoscopic visualization, or fluoroscopic visualization. The balloon and the fluid inside form a "coupling chamber" that allows ultrasound energy to be transmitted to the tissue from inside the balloon. Addition of contrast to the fluid allows fluoroscopic visualization of the shape and diameter.

Figure 38A:
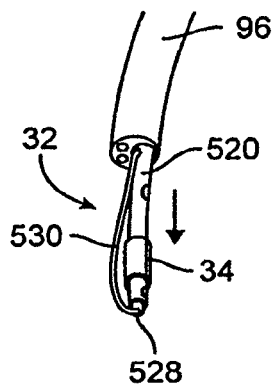
FIG. 38a illustrates advancement of the ablation catheter out of the endoscope.
Figure 38B:
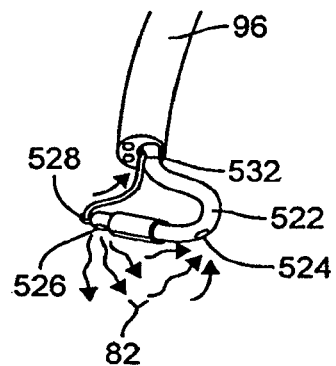
FIG. 38b illustrates manipulation of the tip of the ablation catheter in order to direct the energy in a particular direction.

With the balloon inflated, the distal shaft 520 of the ablation catheter 32 is advanced out of the endoscope channel 518, as shown in FIGS. 38a and 38b. Mounted on the distal shaft 520 is an ultrasound transducer 34. The transducer 34 is preferably a cylinder with only one segment of the circumference active. Other transducers have been described in provisional patent application 60/393,339 and are incorporated by reference herein. An external manipulation member (hereafter called pull wire) 530 is positioned on the side of the distal shaft 520 opposite the active transducer segment. The distal end of the pull wire 530 is attached to a hinge (or weld-joint 528 at the catheter tip, and the proximal end is routed through a lumen orifice 532 in the distal catheter shaft 520 and out the proximal end of the catheter to an actuator on the hub/handle 38. As the pull wire 530 is tensioned, a soft, kink resistant section 522 of the distal shaft 520 forms a tight bend that allows the transducer to be oriented at the desired angle inside the balloon 502. Compression of the pull wire straightens the distal shaft 520 and may also bend it in the opposite direction. The endoscope and/or fluoroscope may be used to determine the proper orientation of the transducer relative to the tissue.

With the transducer 34 oriented towards the tissue, cooling flow circulation is initiated as shown in FIG. 38b, to prevent heating of the mucosa during subsequent energy delivery. Chilled fluid 82 from the pump 80 is preferably routed through a lumen under/behind the transducer, out the distal orifice 526 and back through the proximal (to the transducer) orifice 524 to a separate lumen returning to the pump 80 or other reservoir. Alternatively, or in addition, chilled fluid may be circulated via the overtube lumen or a lumen in the endoscope.

Figure 39:
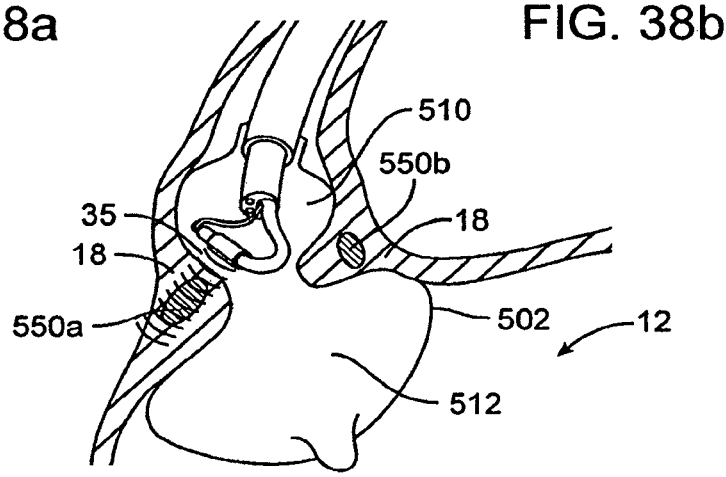
FIG. 39 illustrates lesion formation from above the LES using the preferred system.
Figure 40:
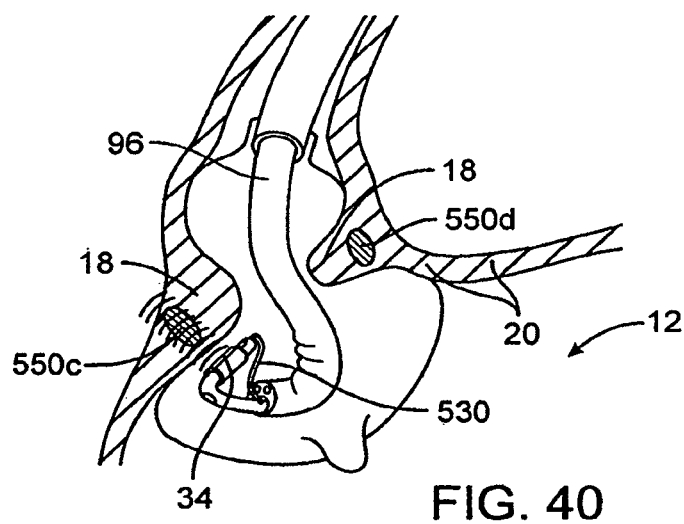
FIG. 40 illustrates lesion formation from below the LES using the preferred system.

As shown in FIG. 39, energy from the generator 70 is applied to the transducer 54, which creates a beam of acoustic energy 35 directed towards the LES tissue 18. The transducer frequency, power level, and power duration are chosen to create a lesion 550a of a desirable size. The catheter 32 may be torqued and the pullwire 530 adjusted to reorient the transducer to another location around the circumference and/or the length of the LES region, where energy delivery and lesion creation are repeated. Ideally, each lesion is formed for about 5-10 mm down the axial length of the LES at a radial depth of 3-8 mm. As shown in FIG. 40, the transducer can also be directed towards the LES 18 from within the stomach 12. Also, from the same position, the transducer can be oriented to ablate the gastric cardia 20, just beyond the LES 18. Lesions in the gastric cardia might be more effective in ablating vagal afferent nerve fibers responsible for transient relaxations of the LES and also reduce the compliance of the gastric sling fibers to delay sphincter opening during gastric distension.

Figure 41:
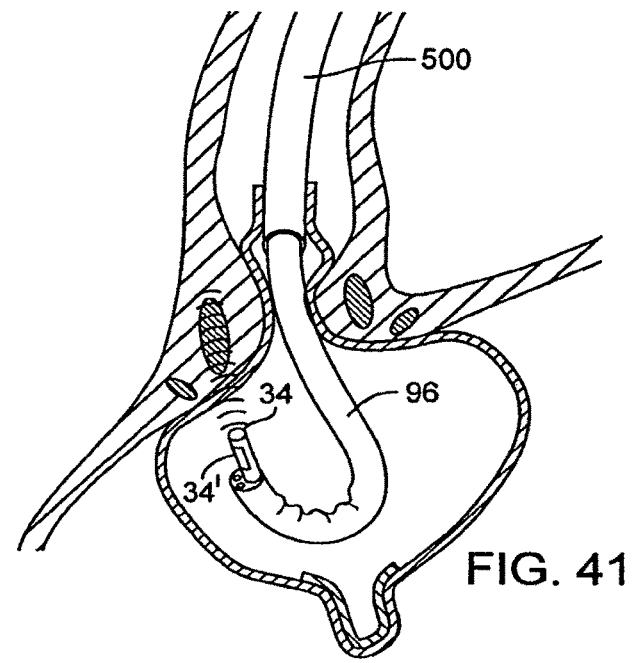
FIG. 41 illustrates lesion formation during the forward delivery of ultrasound from a transducer mounted on the tip of the catheter.

FIG. 41 shows another embodiment of the invention where the transducer 34 is instead (or in addition to) positioned at the tip of the ablation catheter to direct energy in the same direction as the axis of the catheter.

Figure 42:
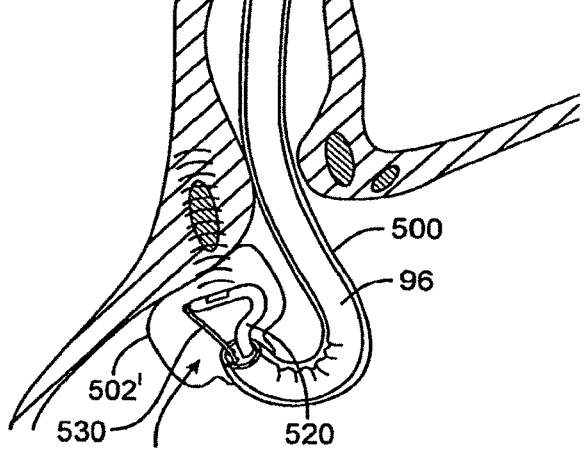
FIG. 42 illustrates lesion formation using the preferred catheter with one external pullwire routed through a second open channel of the endoscope. A smaller, simper overtube balloon is also used.

FIG. 42 shows another embodiment where a smaller balloon 502' is fitted on the tip of the overtube 500 to contain the distal portion of the ablation catheter 32. The distal end of the overtube shaft 500 in this case is aligned with the distal end of the endoscope 96 and may be deflected with the endoscope 96. Also as shown in FIG. 42, the pull wire may be routed through a separate channel of the endoscope (the wire would need to be back-loaded through the endoscope before it is inserted into the overtube).

Figure 43:
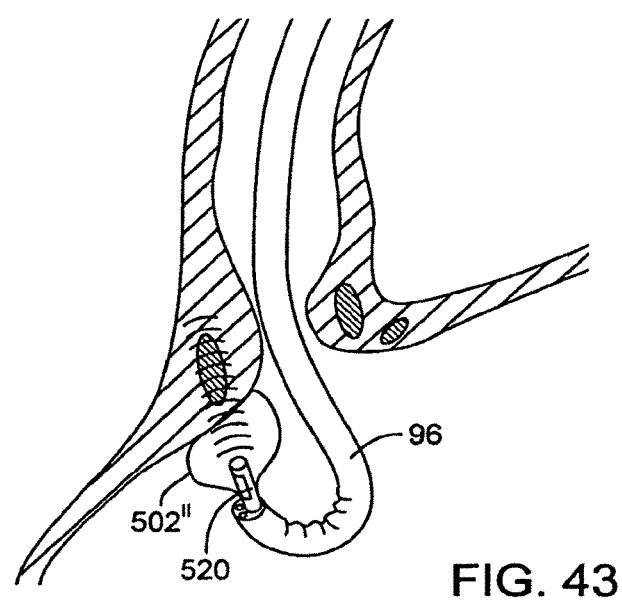
FIG. 43 illustrates lesion formation using a catheter advanced through an endoscope channel. No overtube is used; instead, a balloon is mounted on the catheter tip which inflates outward from the tip of the shaft.

FIG. 43 shows another embodiment where the balloon 502" is attached to the distal shaft 520 of the catheter 32, and no overtube is used. The distal end of pull wire 530 may be attached to the outside of the shaft proximal to the balloon, or fixed inside the distal shaft.

Figure 44:
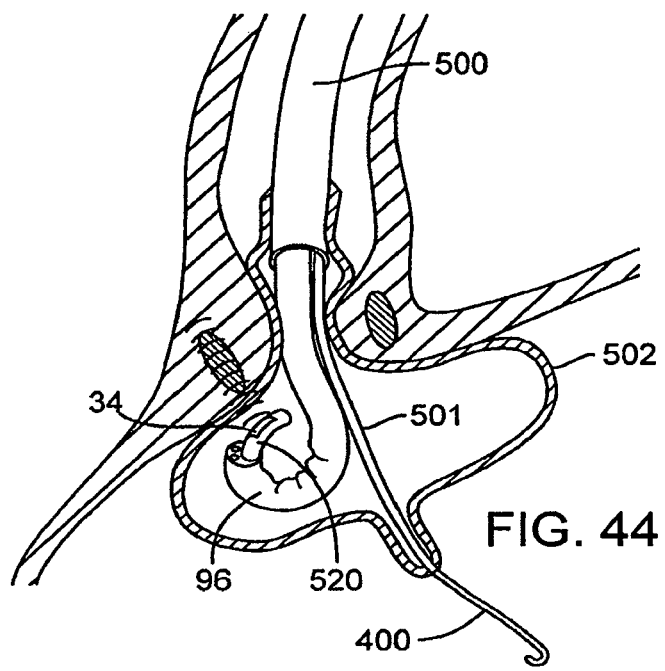
FIG. 44 illustrates lesion formation using a deflectable or preshaped catheter advanced out on an endoscope channel. The overtube has a member extending distally from the distal opening of the overtube. The balloon is mounted at its distal end to the distal end of the member. The member has one or more lumens for fluid delivery and guide wire use.

FIG. 44 shows another embodiment of the overtube 500 where a distal member 501 extends from the distal opening of the overtube to the distal end of the balloon 502. The distal end of the balloon 502 is bonded to the distal end of the member 501. The member 501 may have one or more lumens to allow passage of a guide wire 400, and for inflation/deflation of the balloon, and/or circulating cooling fluid within the balloon. The distal opening of member 501 may also be used to vent air from the stomach. The endoscope 96 carrying catheter 32 may be advanced through the main channel of the overtube 500 as described previously.

Figure 45:
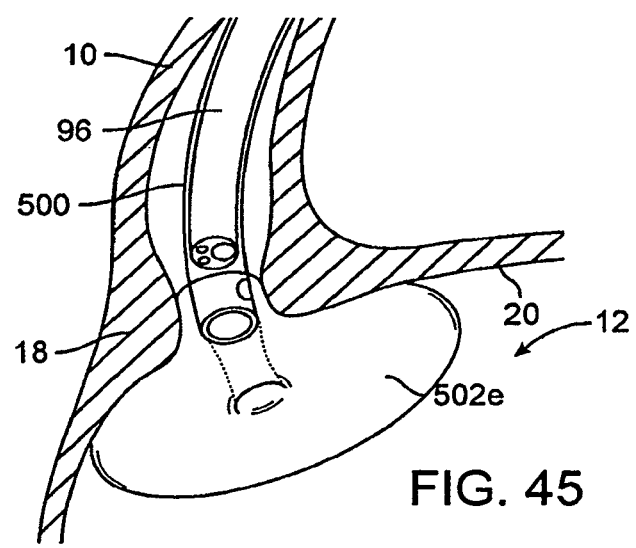
FIG. 45 illustrates the deployment of an overtube having a doughnut shaped balloon.

FIG. 45 shows another embodiment of the overtube 500 employing the use of a doughnut shaped balloon 502e attached to the distal end of the overtube. The doughnut shape allows for a central lumen in the balloon. This may be important to vent air from the stomach 12 or allow passage of the endoscope distal to the balloon. The doughnut shape also provides a good reference to the position of the inferior LES when inflated in the stomach and pulled back against the bottom of the LES.

Figure 46:
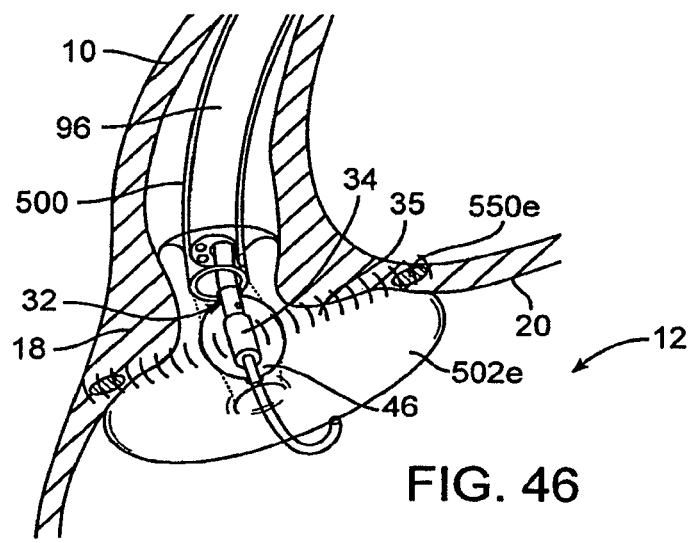
FIG. 46 illustrates the lesion formation from an ultrasound ablation catheter positioned inside the doughnut shaped balloon of the overtube.

FIG. 46 illustrates the use of the ablation catheter 32 with the overtube having a doughnut shaped balloon. The distal end of the ablation catheter 32 is advanced through the center of the doughnut shaped balloon 502e. With the transducer 34 aligned in the desired location, the ablation catheter balloon 46 is inflated inside the overtube balloon 502e. With both the overtube balloon and 502e and the ablation catheter balloon 46 filled with an adequate coupling fluid (i.e., water), the ultrasound energy is able to propagate relatively undamped until it reaches the tissue of the LES 18 or gastric cardia 20. The fluid inside either or both the overtube balloon 502e or the ablation catheter balloon 46 may be recirculated and chilled to prevent overheating of the transducer 34 or the mucosa. Conceivably, the overtube 500 could have a window opening (not shown) proximal to the doughnut shaped balloon 502e. This would allow the balloon 46 of the ablation catheter to inflate out of the inner lumen of the overtube proximal to the overtube balloon 502e.

Figure 47:
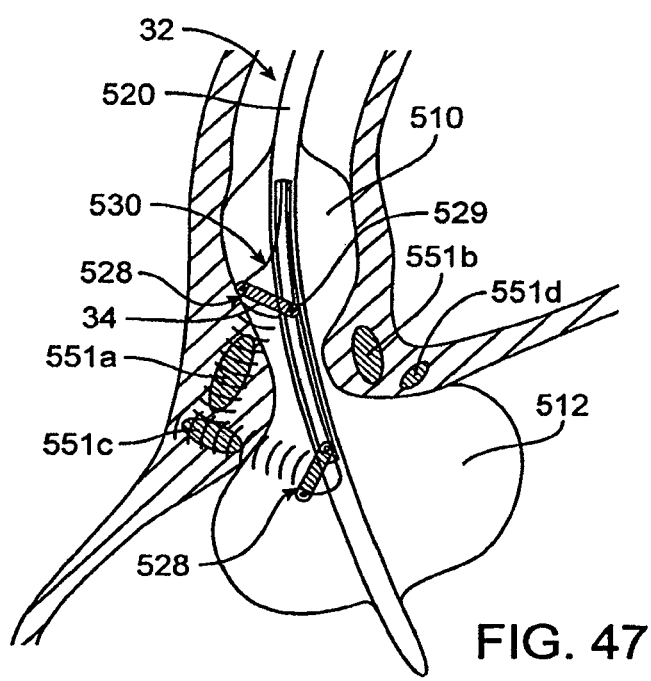
FIG. 47 illustrates lesion formation from a catheter having either or both distal and proximal ablation elements mounted within a peanut shaped balloon.

FIG. 47 shows another embodiment where the peanut shaped balloon 502 is mounted on the distal ablation catheter shaft 520, and no overtube is used. The ablation catheter may or may not be passed through an endoscope 96. If not passed through an endoscope, an endoscope is advanced alongside the catheter shaft, or positioned at the desired location and the distance noted before it is removed and the ablation catheter inserted the same distance. Transducers 34 are mounted on the distal shaft 520 under to balloon at locations either or both distal and proximal to the LES 18 (the sunken region of the peanut balloon 502). The transducers may be hinged to the side of the shaft and at point 229, and hinged at the other end 528 where a pull wire is attached. The pull wire 530 is routed through the shaft 520 to an actuator on the proximal end of the device. Push and pull of the pull wire 530 may allow swiveling of the transducer to create lesions 551a-551d. The transducers may also be driven simultaneously while angled to focus at an intersection point within the wall of the LES 18.

Figure 48A:
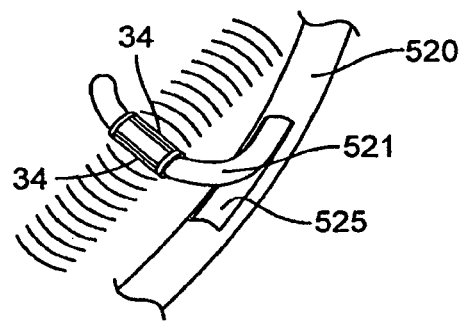
FIGS. 48a-48d illustrate alternative means for changing the orientation of the ultrasound transducer.
Figure 48B:
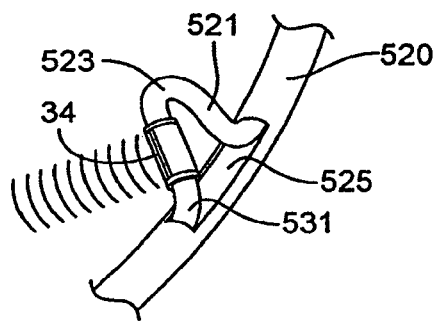
Figure 48C:
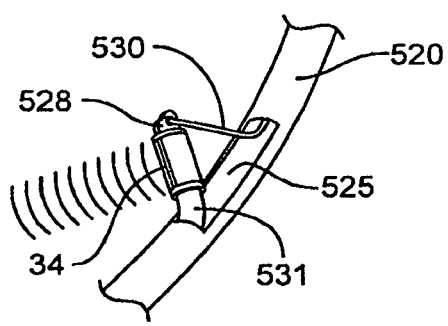
Figure 48D:
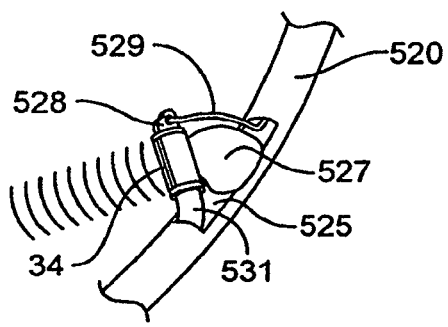

Other embodiments focused on a means to change the angle of the transducer are illustrated in FIGS. 48a-48d. In FIG. 48a, the transducer is mounted on a shaft member 521, which is advanced out of a lumen in the distal shaft 520 of the ablation catheter 32. The shaft 521 may have a set curve or be deflectable with an internal pull wire. It can be seated in a channel 525 in shaft 520 during advancement and retraction. The transducer 34 can be uni- or multidirectional. In FIG. 48b, the shaft 521 continues distal to the transducer where it is fixed inside shaft 520. Pushing and pulling on the proximal shaft 520 causes a prolapse proximal to the transducer at a soft, kink-resistant point 523. In FIG. 48c, pull wire 530 is attached to the proximal end of the transducer at hinge 528. The "pull wire" is pushed forward to increase the transducer angle, and pulled back to reduce the angle. In FIG. 48d, the transducer 34 is angulated by inflating a bladder 527 under the transducer. A floppy tether 529 may be tensioned to fully seat the transducer 34 and bladder 527 into groove 525 during insertion and removal.

Figure 49A:
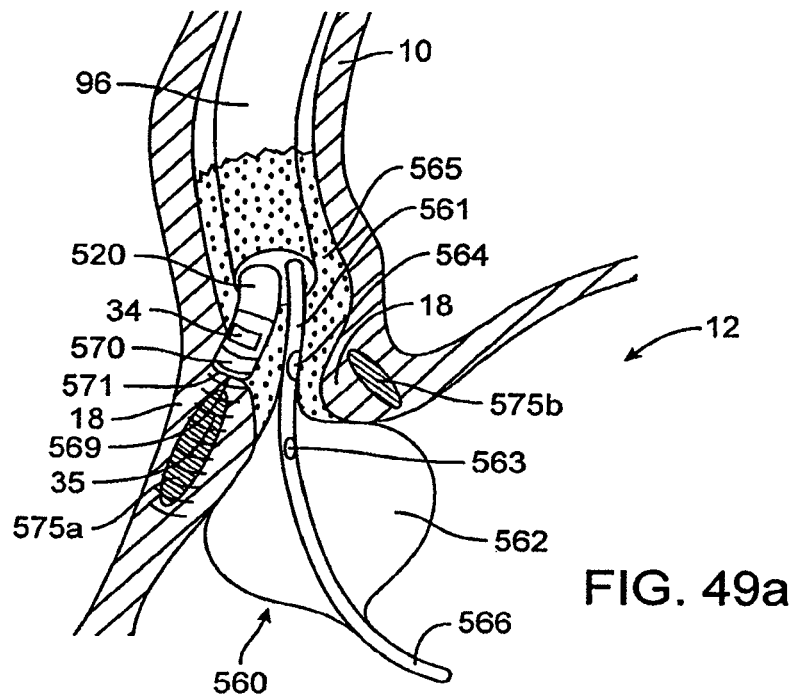
FIG. 49a illustrates lesion formation from an ablation catheter while sealing the distal LES orifice with a balloon catheter.

In another embodiment shown in FIG. 49a, an endoscope 96 with two available channels is advanced down the esophagus 10 to the region of the LES 18. The distal shaft 520 of ablation catheter is advanced out of one of the available channels of the endoscope 96 to the region of the LES 18 to be treated. Mounted on the distal shaft 520 is an ultrasound transducer 34. The transducer 34 is preferably mounted to deliver a beam of acoustic energy in the same direction as the catheter's longitudinal axis, but could also be designed to deliver energy at other angles to the axis. The transducer is optionally surrounded distally by a coupling chamber 570, consisting of a rigid or flexible membrane 571 filled with an acoustic coupling medium (e.g., water, saline, gel). The thickness of the membrane 571 where the ultrasound energy passes is preferably less than one-quarter the wavelength of the ultrasound to prevent transmission loss. One or more temperature sensors 569 may be mounted on the tip of the membrane 571 in the path of the ultrasound beam 35 to monitor temperature of the mucosa to prevent overheating.

An occlusion balloon catheter 560 consisting of a catheter shaft 561 and balloon 562 is advanced through another available channel of the endoscope 96 and distal to the LES 18. The balloon 562 is inflated (with air or water via a lumen in the catheter, exiting at port 563 inside the balloon) in the stomach 12 to a diameter larger than the LES opening and then pulled back against the LES to create a seal. Fluid 565 (e.g., water, saline) is injected through a lumen in catheter 560, exiting from a port 564 proximal to the balloon, to fill the region of the esophagus 10 proximal to the LES 18. This provides a means of ensuring acoustic energy is coupled to the tissue as well as providing a means of cooling the mucosa to prevent heat damage. The fluid 565 may alternatively or additionally be infused through a lumen in the endoscope 96. Circulation of the fluid 565 may also be accomplished through multiple lumens in shaft 561 of catheter 560, or endoscope 96.

Figure 49B:
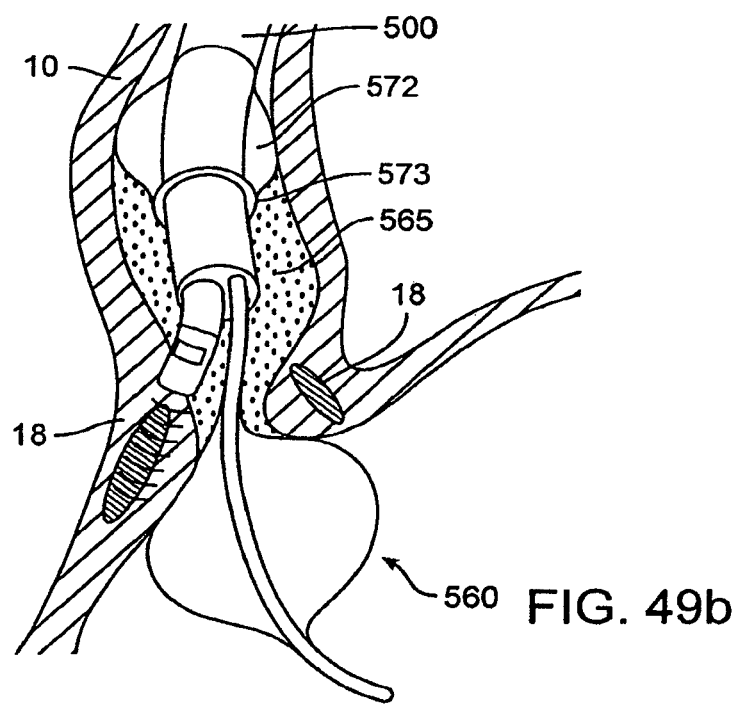
FIG. 49b illustrates lesion formation from an ablation catheter while sealing the distal LES orifice with a balloon catheter and sealing the esophagus proximal to the LES with a balloon on an overtube.
Figure 49C:
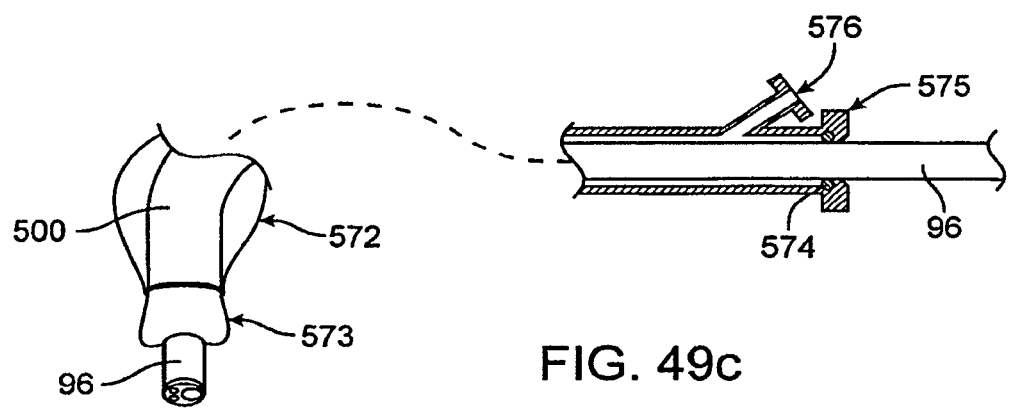
FIG. 49c illustrates the use of a stasis valve between the overtube and endoscope to prevent fluid from flowing out the lumen between the two devices.
Figure 49E:
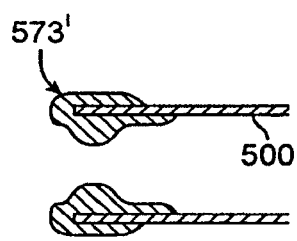
FIGS. 49d and 49e illustrate different embodiments of the stasis valve mounted on the tip of the overtube.
Figure 49D:
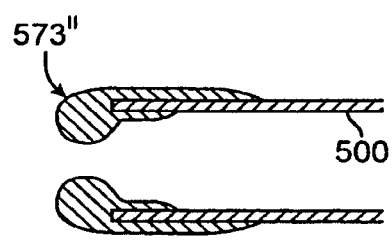

As shown in FIG. 49b, an overtube 500 having a balloon 572 bonded to the distal portion of the overtube shaft may be used to create a proximal seal to contain the fluid 565 infused in the region of the LES 18 (the balloon catheter 560 would continue to be used to contain the fluid 565 at the distal portion of the LES 18). As illustrated in FIG. 49b and FIGS. 49c-e, a stasis valve 573 on the tip of the overtube may be used to prevent fluid from migrating up the space between the endoscope and overtube, as well as to prevent scraping the mucosa when the overtube is moved relative to the endoscope. The valve 573 is compressible (formed from silicone rubber or polyurethane) to accommodate a range of endoscope outer diameters. The proximal end of overtube 500 may be fitted with a similar stasis valve, or o-ring 574 which may be manually compressed by turning a threaded nut 575. A side port luer 576 may be used to flush the lumen of the overtube 500.

Referring back to FIG. 49a, once the fluid 565 is infused, the transducer 34 is energized to deliver ultrasound energy 35 to the region of the LES 18. The energy 35 is delivered for a sufficient time and energy to create a lesion 575a in the tissue in the region of the LES 18. The process may be repeated multiple times around the circumference and/or axis of the LES 18 to create additional lesions, such as 575b.

Figure 50:
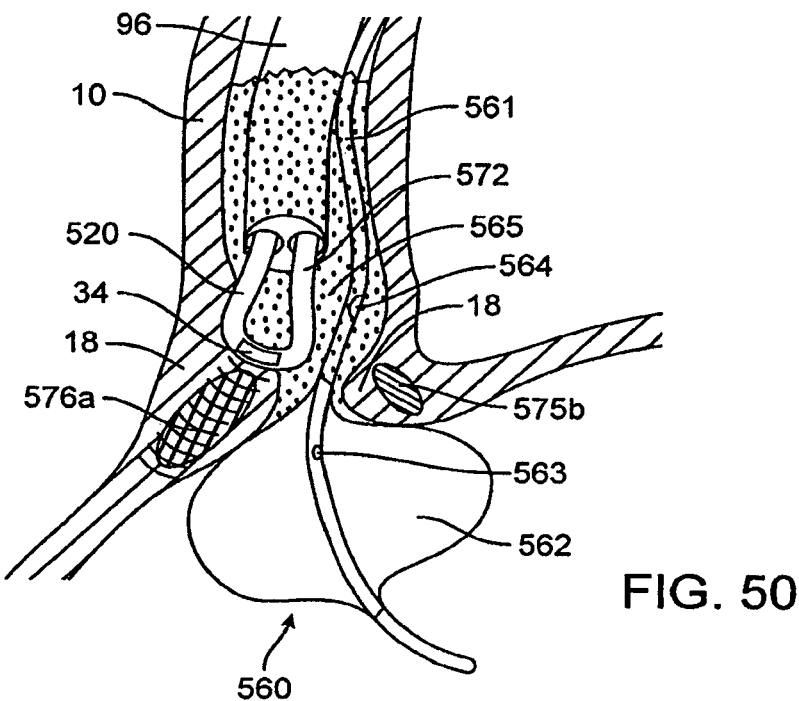
FIG. 50 illustrates lesion formation from an ablation catheter routed through 2 available channels in the endoscope while sealing the distal LES orifice with a balloon catheter.
Figure 51:
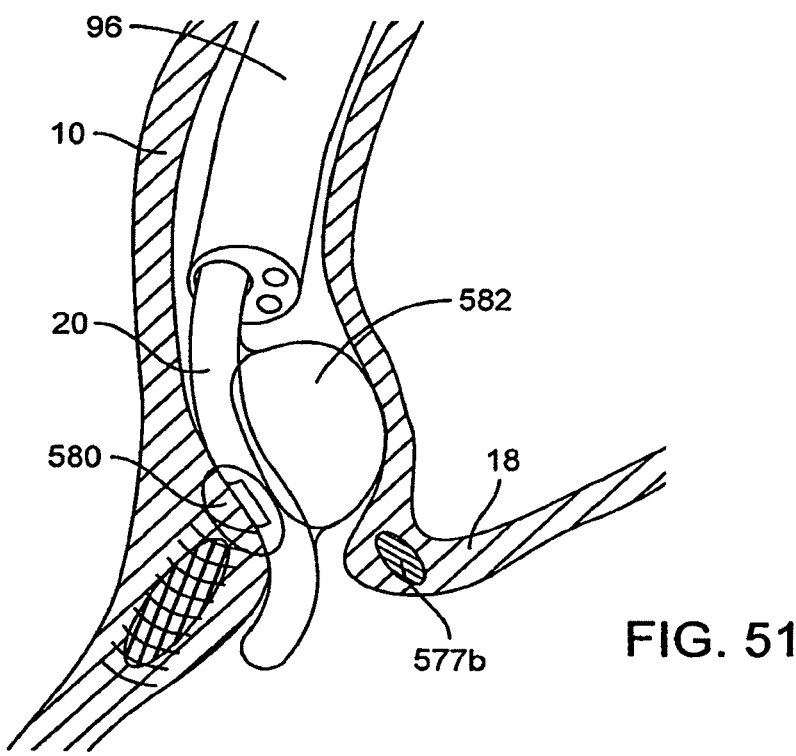
FIG. 51 illustrates lesion formation from an ablation catheter having a membrane surrounding the transducer while a balloon attached to the opposite side of the shaft forcing the transducer against the tissue.

In another embodiment shown in FIG. 50, the ablation catheter 32 is configured similar to that shown in FIG. 51. The catheter 32 is designed to be preloaded in the endoscope 96 such that an extended portion of the shaft 572 distal to the transducer 34 runs from the distal endoscope, out through the proximal end. This allows manipulation of two shaft elements, 570 and 572, proximal and distal to the transducer, respectively, to change the orientation of the transducer 34. The transducer 34 in this configuration is elongated such that its width is approximately the same as the diameter of the catheter shaft, and the length is in the range of 3-10 mm. An occlusion balloon catheter 560 is again positioned distal to the LES, but runs alongside the endoscope 96, not through it. An overtube 500 with balloon 572 may be used in a manner similar to that of FIG. 49b. As described for FIGS. 49a and 49b, fluid 565 is infused into the region of the LES 18 and acoustic energy 35 is delivered from the transducer 34 into the tissue to form lesions in various locations such as 576a and 576b.

In another embodiment shown in FIG. 51, the distal shaft 520 of ablation catheter 32 is advanced out of an endoscope 96 in the region of the LES 18. In this embodiment, the endoscope only requires one free channel, that dedicated to the ablation catheter 32. The distal shaft 520 of the catheter 32 is fitted with a transducer 34, mounted along the side of the of the catheter shaft. The transducer is surrounded by a membrane 580 with features and function similar to that described for FIG. 49a to aid in coupling of the ultrasound energy to the tissue. The fluid or gel in the membrane may be recirculated to keep the transducer and mucosa cool. Mounted to the opposite side of the shaft 520 from the transducer 34 is an expandable member 582 designed to force the membrane 580 surrounding the transducer 34 securely against the tissue. The expandable member 582 is preferably a balloon, but could also consist of one or more moveable splines designed to bow against the tissue. An internal pull wire mechanism (not shown) connected to a proximal actuator could also be employed to aid in deflecting the distal shaft 520 against the tissue in the region of the LES 18. Once in position against the tissue, ultrasound energy 35 is delivered from the transducer 34 to form lesions in various positions in proximity to the LES, such as 577a and 577b.

In another embodiment shown in FIG. 52a and FIG. 52b, an ablation catheter 32 is advanced to the region of the LES. Accurate positioning at the LES is accomplished by using markings on the shaft corresponding to previous use of an endoscope, or placing an endoscope alongside the shaft of the ablation catheter. Constructed on the distal end of catheter shaft 520 is a tissue chamber 590 designed to accept a portion of the muscle wall in the region of the LES 18. The tissue chamber may measure 5-25 mm long and 3-10 mm deep. Constructed proximal to the tissue chamber 590 is a transducer assembly chamber 592. Within chamber 592 a transducer assembly 594 is slideable via a piston 596 connected to an actuator on the proximal end of the catheter 32. The transducer assembly 594 consists of a transducer 34 mounted with proximal air backing and a distal coupling chamber 598 formed by a membrane 599 (similar in form and function to that described for FIG. 49). Cooling fluid 600 may be circulated in and out of the chamber 598. Using the piston 596 the assembly may be pushed down onto the tissue drawn into the tissue chamber 590. To aid in drawing the tissue into the chamber 590 and securing it there, suction from a plurality ports 601 may be employed. The use on an expandable member 602 (balloon or splines) mounted opposite to the chamber may aid in forcing the catheter into the tissue (and thus the tissue into the chamber 590).

At the distal end of the chamber is an optional chamber 604 that may also accept circulated cooling fluid 600 to keep the distal end of the mucosa from overheating. Distal to optional chamber 604 is an element 606 that can be configured to absorb ultrasound energy not absorbed by the tissue. This may consist of a highly attenuating material such as silicone or polyurethane rubber. Alternatively, element 606 could be another transducer 34 that directs energy into the tissue towards that coming from the transducer assembly 594 to increase the heating within the tissue. An atraumatic tip 608 is attached to the distal tip of the catheter 32. Once the tissue is pulled into the coupling chamber 590, the transducer assembly 594 pushed against the tissue and infused with cooling fluid 600, ultrasound energy 35 is delivered into the tissue to form a lesion 610.

An alternative embodiment of the device described in FIG. 52 would be to not require the transducer assembly 594 to be moveable, and thereby eliminate the need for the piston 596. The push force onto the tissue could be accomplished by designing the membrane 599 to be outward expandable. Also, an internal pull wire mechanism (not shown) attached to the distal tip of the catheter and connected to a proximal actuator could also be employed to aid in deflecting the distal shaft 520 against the tissue in the region of the LES 18. More specifically, the pull wire may be used to curl the distal tip 608 (and attached segments 606 and 604 under and against the LES tissue.

Figure 53A:
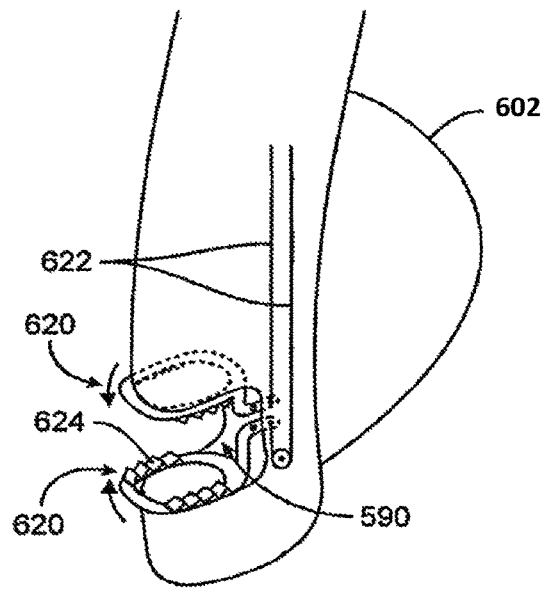
FIGS. 53a and 53b illustrate the use of mechanical swivel grips to draw tissue into and hold within an ablation chamber.
Figure 53B:
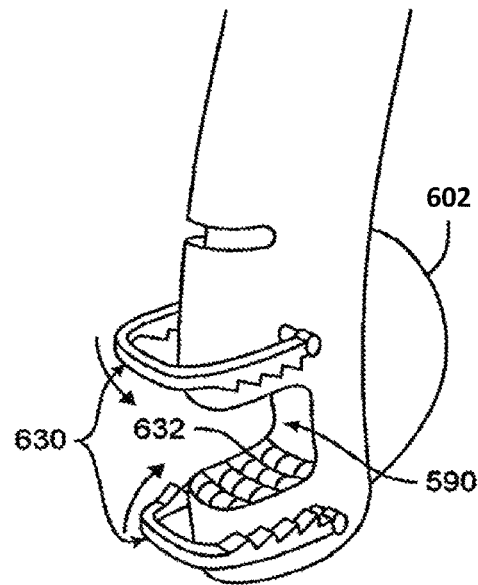
Figure 53C:
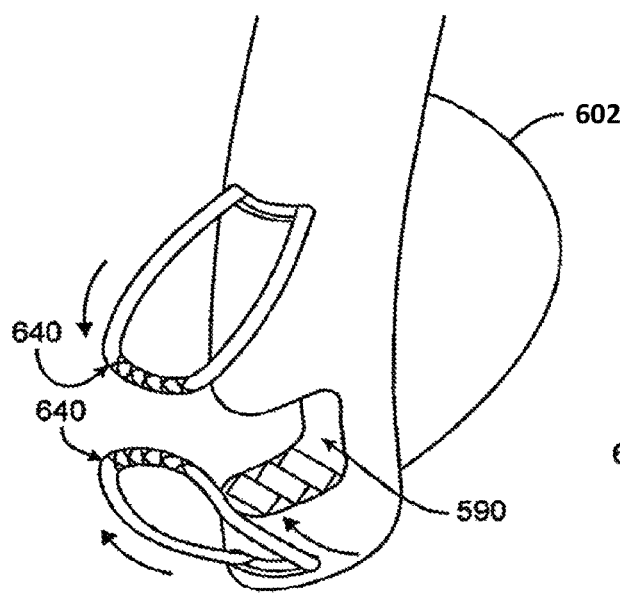
FIG. 53c illustrates the use of wire to press tissue into and hold within an ablation chamber.
Figure 53D:
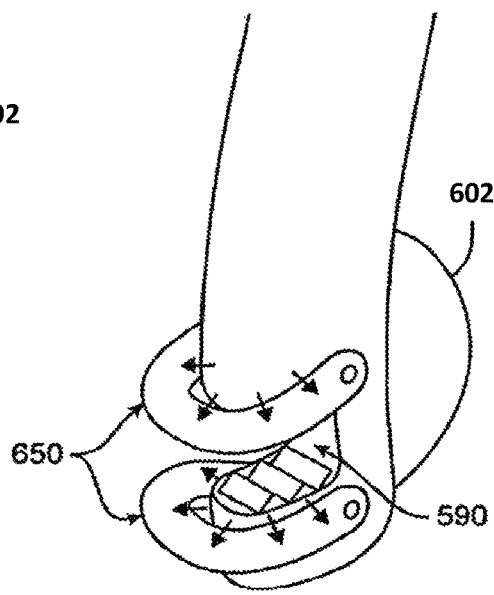
FIG. 53d illustrates the use of inflatable doughnuts to press tissue into and hold within an ablation chamber.

Other means may be used in addition to or in place of that described for FIG. 52 to draw the tissue into the tissue chamber. FIG. 53a illustrates grasping mechanisms 620 actuated by pull wires 622 connected to an actuator at the proximal end of catheter 32. The grasping mechanisms 620 are formed from a metal or hard plastic and contain frictional tread 624 to assist in holding the slippery tissue. They are also contained within the chamber 590 and hollow in the middle so as to not interfere with the ultrasound energy. The grasping mechanisms 630 illustrated in FIG. 53b are similar to FIG. 53a except that they swing out from the catheter shaft to help pull more tissue into the chamber 590. Additional tread 632 on the bottom (distal) end of the chamber would aid in holding the tissue in place. FIG. 53c shows preformed wire (i.e., stainless steel or nitenol) being advanced out of the catheter shaft to pinch the tissue and help force it into the tissue chamber 590. In FIG. 53d, two "partial doughnut" balloons are inflated to help pinch and push the tissue into the tissue chamber.

What is claimed is:
1. A method of intraluminal ablation of nerve tissue surrounding a bodily lumen of a subject, comprising:
 delivering an ablation device within a bodily lumen of a subject, the ablation device comprising a catheter hav- ing a fluid passage, a balloon and an ultrasound transducer disposed along a distal end of the catheter within the balloon, the ultrasound transducer having a resonating region with a first diameter and an integral circumferential step that forms a non-resonating region with a second diameter, the fluid passage being in fluid communication with the balloon, and wherein the integral circumferential step is at an end of the ultrasound transducer;

advancing the ablation device within the bodily lumen to position the ultrasound transducer adjacent target nerve tissue of the subject, wherein the target nerve tissue is positioned in nerve pathways that run adjacent the bodily lumen;

delivering a cooling fluid through the fluid passage to inflate the balloon to a circular cross-sectional shape, coaxial with the ultrasound transducer, to center the ultrasound transducer within the bodily lumen so as to locate the ultrasound transducer at a pre-determined position relative to a wall of the bodily lumen;

circulating the cooling fluid through an interior of the balloon via the fluid passage to remove heat from the ultrasound transducer and to reduce a likelihood of heating a lining of the bodily lumen to the point of irreversible damage; and activating the ultrasound transducer to excite the resonating region to deliver ultrasonic energy radially outwardly through the balloon and the wall of the bodily lumen while cooling fluid is circulated through the interior of the balloon, the ultrasound energy being delivered around an entire circumference of the bodily lumen to at least partially ablate the target nerve tissue in a uniform annulus of tissue at a depth of 1 mm to 10 mm from the wall of the bodily lumen, the non-resonating region reducing the transmission of ultrasonic energy to the distal end of the catheter.

2. The method of claim 1, wherein delivering the cooling fluid to the balloon comprises providing fluid within an interior of the balloon so that the balloon at least partially engages the wall of the bodily lumen.

3. The method of claim 1, wherein energizing the ultrasound transducer raises a temperature of a targeted anatomical tissue by 55° C. to 95° C.

4. The method of claim 1, wherein energizing the ultrasound transducer raises a temperature of a targeted anatomical tissue by 60° C. to 80° C.

5. The method of claim 1, wherein the balloon comprises at least one compliant material.

6. The method of claim 1, wherein the balloon comprises at least one non-compliant material.

7. A method of intraluminal ablation of nerve tissue surrounding a bodily lumen of a subject, comprising;
inserting an ablation device within a bodily lumen of a subject, the ablation device comprising a catheter, a balloon and ultrasound transducer disposed on a distal region of the catheter within the balloon, the ultrasound transducer having a resonating region of a first diameter and an integral circumferential step forming a non-resonating region of a second diameter, wherein the integral circumferential step is at an end of the ultrasound transducer;

advancing the ablation device within the bodily lumen to position the ultrasound transducer near a target anatomical location of the subject, wherein the target nerve tissue is positioned in nerve pathways that run adjacent the bodily lumen along the target anatomical location;

at least partially inflating the balloon by delivering a fluid into an interior of the balloon to reduce the likelihood of heating an inner lining of the bodily lumen to the point of irreversible damage, the balloon when inflated having a circular cross-sectional shape coaxial with the ultrasound transducer and that radially centers the ultrasound transducer within the bodily lumen at a pre-determined position relative to a wall of the bodily lumen; and activating the ultrasound transducer to excite the resonating region to emit ultrasonic energy outwardly toward and through a wall of the bodily lumen, around an entire circumference of the bodily lumen, so as to ablate nerve tissue positioned adjacent the wall of the bodily lumen within a uniform annulus of tissue.

8. The method of claim 7, further comprising circulating a fluid through an interior of the balloon during activation of the ultrasound transducer to remove heat from the ultrasound transducer.

9. The method of claim 7, wherein at least partially inflating the balloon comprises providing fluid within the interior of the balloon so that the balloon at least partially contacts the wall of the bodily lumen.

10. The method of claim 7, wherein activating the ultrasound transducer raises a temperature of a targeted anatomical tissue by 55° C. to 95° C.

11. A method of intraluminal ablation of nerve tissue surrounding a bodily lumen of a subject, comprising:
inserting an ablation device, within a bodily lumen of a subject, the ablation device comprising a catheter having a distal region, a balloon disposed on the distal region and an ultrasound transducer disposed within the balloon, the ultrasound transducer having a resonating region of a first diameter and an integral circumferential step forming a non-resonating region of a second diameter, wherein the integral circumferential step is at an end of the ultrasound transducer;

advancing the ablation device within the bodily lumen to position the ultrasound transducer near a target anatomical location of the subject, wherein the target nerve tissue is positioned in nerve pathways that run adjacent the bodily lumen along the location of the ultrasound transducer;

at least partially inflating the balloon by circulating a cooling fluid through the interior of the balloon to transfer heat away from the ultrasound transducer to reduce the likelihood of heating an inner lining of the bodily lumen to the point of irreversible damage, the balloon, when inflated, centering the ultrasound transducer within the bodily lumen at a pre-determined position relative to a wall of the bodily lumen;

activating the ultrasound transducer to excite the resonating region to deliver ultrasonic energy outwardly toward a wall of the bodily lumen, around an entire circumference of the bodily lumen, to ablate nerve tissue positioned adjacent the wall of the bodily lumen in an annulus of tissue having a depth of 1 mm to 10 mm from the wall of the bodily lumen.

12. The method of claim 11, wherein at least partially inflating the balloon comprises providing cooling fluid within the interior of the balloon so that the balloon at least partially contacts the wall of the bodily lumen.

13. The method of claim 11, wherein circulating a cooling fluid within the interior of the balloon comprises circulating the cooling fluid through at least two separate fluid passages of the catheter.

* * * * *